(12) United States Patent
Holmdahl et al.

(10) Patent No.: US 7,148,020 B2
(45) Date of Patent: Dec. 12, 2006

(54) TRIPLE POLYPEPTIDE COMPLEXES

(75) Inventors: Rikard Holmdahl, Lund (SE); Jan Ake Engstrom, Bålinge (SE); Jan Kihlberg, Sävar (SE); Harald Burkhardt, Erlangen (DE)

(73) Assignee: Arexis AB, Molndal (SE)

( * ) Notice: Subject to any disclaimer, the term of this patent is extended or adjusted under 35 U.S.C. 154(b) by 262 days.

(21) Appl. No.: 10/194,441

(22) Filed: Jul. 11, 2002

(65) Prior Publication Data

US 2003/0148944 A1 Aug. 7, 2003

Related U.S. Application Data

(60) Provisional application No. 60/305,048, filed on Jul. 12, 2001.

(51) Int. Cl.
*G01N 33/53* (2006.01)

(52) U.S. Cl. ....................................................... 435/7.1

(58) Field of Classification Search ................... 514/12; 530/350

See application file for complete search history.

(56) References Cited

U.S. PATENT DOCUMENTS

| 4,683,195 A | 7/1987 | Mullis et al. |
| 4,873,191 A | 10/1989 | Wagner et al. |
| 5,580,859 A | 12/1996 | Felgner et al. |
| 5,589,466 A | 12/1996 | Felgner et al. |
| 5,726,243 A | 3/1998 | Fields |
| 5,849,323 A | 12/1998 | Braswell et al. |

FOREIGN PATENT DOCUMENTS

| EP | 0 718 308 B1 | 12/1999 |
| WO | WO 96/20950 | 7/1996 |
| WO | WO 97/19106 | 5/1997 |
| WO | WO 98/33811 | 8/1998 |
| WO | WO 99/10381 | 3/1999 |
| WO | WO 00/12538 | 3/2000 |

OTHER PUBLICATIONS

Fields et al., "Solid-phase synthesis of triple-helical collagen-model peptides," *Letters in Peptide Science*, 1996, 3:3-16.
Altman et al., "Development of Criteria fo rthe Classification and Reporting of Osteoarthritis," *Arthritis and Rheumatism*, 1986, 29(8):1039-1049.
Altman et al., "The American College of Rheumatology Criteria for the Classification and Reporting of Osteoarthritis of the Hip," *Arthritis and Rheumatism*, 1991, 34(5):505-514.

Andersson and Holmdahl, "Analysis of type II collagen-reactive T cells in the mouse," *Eur. J. Immunol.*, 1990, 20:1061-1066.
Arnett et al., "The American Rheumatism Association 1987 Revised Criteria for the Classification of Rheumatoid Arthritis," *Arthritis and Rheumatism*, 1988, 31(3):315-324.
Assenmacher et al., "Sequential production of IL-2, IFN-γ and IL-10 by individual staphylococcal enterotoxin B-activated T helper lymphocytes," *Eur. J. Immunol.*, 1998, 28:1534-1543.
Bäcklund et al., "Reversal of tolerance induced by transplantation of skin expressing the immunodominant T cell epitope of rat type II collagen entitles development of collagen-induced arthritis but not graft rejection," *Eur. J. Immunol.*, 2002, 32:1773-1783.
Bäcklund et al., "Predominant selection of T cells specific for the glycosylated collagen type II epitope (263-270) in humanized transgenic mice and in rheumatoid arthritis," *Proc. Natl. Acad. Sci. USA*, 2002, 99(15):9611-9613.
Bengtsson et al., "Convergent synthesis of neoglycopeptides by coupling of 2-bromoethyl glycosides to cysteine and homocysteine residues in T cell stimulating peptides," *Glycoconjugate Journal*, 1998, 15:223-231.
Borgia and Fields, "Chemical synthesis of proteins," *Trends Biotechnol.*, 2000, 18(6):243-251.
Broddefalk et al., "Preparation of a Glycopeptide Analogue of Type II Collagen—Use of Acid Labile Protective Groups for Carbohydrate Moieties in Solid Phase Synthesis of O-Linked Glycopeptides," *Tetrahedron Letters*, 1996, 37(17):3011-3014.
Broddefalk et al., "T Cells Recognize a Glycopeptide Derived from Type II Collagen in a Model for Rheumatoid Arthritis," *J. Am. Chem. Soc.*, 1998, 120:7676-7683.
Broddefalk et al., "Use of Acid-labile Protective Groups for Carbohydrate Moieties in Synthesis of Glycopeptides Related to Type II Collagen," *Tetrahedron*, 1998, 54:12047-12070.
Broddefalk et al., "Preparation of a Diglycosylated Hydroxylysine Building Block Used in Solid-Phase Synthesis of a Glycopeptide from Type II Collagen," *J. Org. Chem.*, 1998, 64:8948-8953.
Cardell et al., "Manipulation of the superantigen-induced lymphokine response. Selective inductionof interleukin-10 or interferon-γ synthesis in small resting CD4+ T cells," *Eur. J. Immunol.*, 1993, 23:523-529.

(Continued)

*Primary Examiner*—Karen Cochrane Carlson
*Assistant Examiner*—Agnes Rooke
(74) *Attorney, Agent, or Firm*—Fish & Richardson P.C.

(57) ABSTRACT

The invention provides methods and materials related to treating and diagnosing autoimmune conditions. Specifically, the invention provides polypeptide compositions, nucleic acids, substantially pure polypeptides, host cells, and methods for identifying a mammal with an autoimmune condition, treating a mammal with an autoimmune condition, and enhancing tolerance in a mammal with an autoimmune condition.

6 Claims, 38 Drawing Sheets

OTHER PUBLICATIONS

Corthay et al., "Epitope glycosylation plays a critical role for T cell recognition of type II collagen in collagen-induced arthritis," *Eur. J. Immunol.*, 1998, 28:2580-2590.

Feng et al., "Acetyl-Terminated and Template-Assembled Collagen-Based Polypeptides Composed of Gly-Pro-Hyp Sequences 2. Synthesis and Conformational Analysis by Circular Dichroism, Ultraviolet Absorbance, and Optical Rotation," *J. Am. Chem. Soc.*, 1996, 118:10351-10358.

Flegel and Sheppard, "A Sensitive, General Method for Quantitative Monitoring of Continuous Flow Solid Phase Peptide Synthesis," *J. Chem. Soc. Chem. Commun.*, 1990, pp. 536-538.

Goodman et al. "A Template-Induced *Incipient* Collagen-Like Triple-Helical Structure," *J. Am. Chem. Soc.*, 1996, 118:5156-5157.

Gossler et al., "Transgenesis by means of blastocyst-derived embryonic stem cell lines," *Proc. Natl. Acad. Sci. USA*, 1986, 83:9065-9069.

Grab et al., "Promotion of Fibroblast Adhesion by Triple-helical Peptide Models of Type I Collagen-derived Sequences," *J. Biol. Chem.*, 1996, 271(21):12234-12240.

Greiche and Heidemann, "Collagen Model Peptides with Antiparallel Structure," *Biopolymers*, 1979, 18(9):2359-61.

Hansson et al. "A new animal model for relapsing polychondritis, induced by cartilage matrix protein (matrilin-1)," *J. Clin. Invest.*, 1999, 104(5):589-598.

Häuselmann et al. "Can Collagen Type II Sustain a Methotrexate-Induced Therapeutic Effect in Patients with Long-Standing Rheumatoid Arthritis? A Double-Blind, Randomized Trial," *Br. J. Rheumatol.*, 1998, 37:1110-1117.

Henkel et al., "Synthesis and Folding of Native Collagen III Model Peptides," *Biochemistry*, 1999, 38:13610-13622.

Hojo et al., "Synthesis and Structural Characterization of Triple-Helical Peptides Which Mimic the Ligand Binding Site of the Human Macrophage Scavenger Receptor," *Tetrahedron*, 1997, 53(42):14263-14274.

Holm et al., "An Improved Synthesis of a Galactosylated Hydroxylsine Building Block and its use in Solid-Phase Glycopeptide Synthesis," *Tetrahedron*, 2000, 56:1579-1586.

Kihlberg and Ahman, "Glycosylated Peptide Hormones: Pharmacological Properties and Conformational Studies of Analogues of [1-Desamino,8-D-arginine]vasopressin," *J. Med. Chem.*, 1995, 38:161-169.

Lauer-Fields et al., "Hydrolysis of Triple-helical Collagen Peptide Models by Matrix Metalloproteinases," *J. Biol. Chem.*, 2000, 275(18):13282-13290.

Lo, "Transformation by Iontophoretic Microinjection of DNA: Multiple Integrations Without Tandem Insertions," *Mol. Cell. Biol.*, 1983, 3(10):1803-1814.

Malmström et al., "Systemic versus cartilage-specific expression of a type II collagen-specific T-cell epitope determine the level of tolerance and susceptibility to arthritis," *Proc. Natl. Acad. Sci. USA*, 1996, 93:4480-4485.

Mechling and Bächinger, "The Collagen-like Peptide $(GER)_{15}GPCCG$ Forms pH-dependent Covalently Linked Triple Helical Trimers," *J. Biol. Chem.*, 2000, 275(19):14532-14536.

Michaëlsson et al., "T Cell Recognition of Carbohydrates on Type II Collagen," *J. Exp. Med.*, 1994, 180:745-749.

Michet et al., "Relapsing Polychondritis," *Annals of Internal Medicine*, 1986, 104:74-78.

Müller et al., "Heterotrimeric Collagen Peptides as Fluorogenic Collagenase Substrates: Synthesis, Conformational Properties, and Enzymatic Digestion," *Biochemistry*, 2000, 39:5111-5116.

Ottl and Moroder, "A New Strategy for Regioselective Interstrand Disulfide Bridging of Multiple Cysteine Peptides," *Tetrahedron Letters*, 1999, 40:1487-1490.

Sambrook et al., *Molecular Cloning—A Laboratory Manual*, Second Edition, 1989, Cold Spring Harbor Laboratory, Plainview, NY, pp. 7.39-7.52.

Schellekens et al., "Citrulline is an Essential Constituent of Antigenic Determinants Recognized by Rheumatoid Arthritis-specific Autoantibodies," *J. Clin. Invest.*, 1998, 101(1):273-281.

Schnieke et al., "Human Factor IX Transgenic Sheep Produced by Transfer of Nuclei from Transfected Fetal Fibroblasts," *Science*, 1997, 278:2130-2133.

Tanaka et al., "Synthesis and stabilization of amino and carboxy terminal constrained collagenous peptides," *J. Peptide Res.*, '998, 51(6):413-419.

Thompson et al., "Germ Line Transmission and Expression of a Corrected HPRT Gene Produced by Gene Targeting in Embryonic Stem Cells," *Cell*, 1989, 56:313-321.

van der Putten et al., "Efficient insertion of genes into the mouse germ line via retroviral vectors," *Proc. Natl. Acad. Sci. USA*, 1985, 82:6148-6152.

Wellner et al., "Synthesis of a *C*-Glycoside Analogue of β-D-Galactosyl Hydroxynorvaline and Its Use in Immunological Studies," *Chembiochem.*, 2000, 1:272-280.

Yan et al., "Specificity and Tcell receptor β chain usage of a human collagen type II-reactive T cell clone derived from a healthy individual," *Eur. J. Immunol.*, 1992, 22:51-56.

```
1........x.........x..........x..........x.........L........x.........x..........x
GPMGPMGPRGPPGPAGAPGPQGFQGNPGEPGEPGVSGPMGPRGPPGPAGKPGDDGEAGKPGKSGERGLPGPQGARGFPGT
.............................................P..............A....P............

.........x..........C.........x..........x..........x.........x..........L.........x
PGLPGVKGHRGYPGLDGAKGEAGAPGVKGESGSPGENGSPGPMGPRGLPGERGRTGPAGAAGARGNDGQPGPAGPPGPVG
................................................................................

.........x..........x..........x..........C.........x..........x..........x.........x
PAGGPGFPGAPGAKGEAGPTGARGPEGAQGSRGEPGNPGSPGPAGASGNPGTDGIPGAKGSAGAPGIAGAPGFPGPRGPP
............................P.....T............................................

.........L..........x..........x..........x..........x..........C..........x.........x
GPQGATGPLGPKGQAGEPGIAGFKGDQGPKGETGPAGPQGAPGPAGEEGKRGARGEPGGAGPIGPPGERGAPGNRGFPGQ
.........T..........E......P.............................V.....................

.........x..........x..........L.........x..........x..........x..........x.........C
DGLAGPKGAPGERGPSGLAGPKGANGDPGRPGEPGLPGARGLTGRPGDAGPQGKVGPSGAPGEDGRPGPPGPQGARGQPG
................................................................................

.........x..........x..........x..........x.........L..........x..........x.........x
VMGFPGPKGANGEPGKAGEKGLAGAPGLRGLPGKDGETGAAGPPGPSGPAGERGEQGAPGPSGFQGLPGPPGPPGEGGKQ
.............P....................................A..........................P

.........x..........C.........x..........x..........x..........x.........L........ x
GDQGIPGEAGAPGLVGPRGERGFPGERGSPGAQGLQGPRGLPGTPGTDGPKGAAGPDGPPGAQGPPGLQGMPGERGAAGI
....V.....................................................S..A.................

.........x..........x..........x..........C.........x..........x..........x.........x
AGPKGDRGDVGEKGPEGAPGKDGGRGLTGPIGPPGPAGANGEKGEVGPPGPSGSTGARGAPGEPGETGPPGPAGFAGPPG
........................................................A..A...................

.........L..........x..........x..........x..........x..........C..........x.........x
ADGQPGAKGDQGEAGQKGDAGAPGPQGPSGAPGPQGPTGVTGPKGARGAQGPPGATGFPGAAGRVGPPGANGNPGPAGPP
.........E..............................................................S......P...

.........x..........x.........L..........x..........x..........x..........x.........C
GPAGKDGPKGVRGDSGPPGRAGDPGLQGPAGAPGEKGEPGDDGPSGLDGPPGPQGLAGQRGIVGLPGQRGERGFPGLPGP
..S.......A..........E........P.............AE..................................

.........x..........x..........x..........x.........L..........x..........x.........x
SGEPGKQGAPGASGDRGPPGPVGPPGLTGPAGEPGREGSPGADGPPGRDGAAGVKGDRGETGALGAPGAPGPPGSPGPAG
..............................................V................................

.........x..........x..........x..........x..........x..........x.........L.........x
PTGKQGDRGEAGAQGPMGPSGPAGARGIAGPQGPRGDKGESGEQGERGLKGHRGFTGLQGLPGPPGPSGDQGASGPAGPS
.......................Q...........A..P.........................................

.........x..........x..........x..........C.........x....
GPRGPPGPVGPSGKDGSNGIPGPIGPPGPGPRGRSGETGPVGPPGSPGPPGPPGPP  (SEQ ID NO:48)
................A......................A....N..........  (SEQ ID NO:1)
```

*Fig. 1*

```
1
ATGATTCGCC TCGGGCTCC  CCAGTCGCTG GTGCTGCTGA
41
CGCTGCTCGT CGCCGCTGTC CTTCGGTGTC AGGGCCAGGA
81
TGTCCAGGAG GCTGGCAGCT GTGTGCAGGA TGGGCAGAGG
121
TATAATGATA AGGATGTGTG GAAGCCGGAG CCCTGCCGGA
161
TCTGTGTCTG TGACACTGGG ACTGTCCTCT GCGACGACAT
201
AATCTGTGAA GACGTGAAAG ACTGCCTCAG CCCTGAGATC
241
CCCTTCGGAG AGTGCTGCCC CATCTGCCCA ACTGACCTCG
281
CCACTGCCAG TGGGCAACCA GGACCAAAGG GACAGAAAGG
321
AGAACCTGGA GACATCAAGG ATATTGTAGG ACCCAAAGGA
361
CCTCCTGGGC CTCAGGGACC TGCAGGGGAA CAAGGACCCA
401
GAGGGGATCG TGGTGACAAA GGTGAAAAAG GTGCCCCTGG
441
ACCTCGTGGC AGAGATGGAG AACCTGGGAC CCCTGGAAAT
481
CCTGGCCCCC CTGGTCCTCC CGGCCCCCCT GGTCCCCCTG
521
GTCTTGGTGG AAACTTTGCT GCCCAGATGG CTGGAGGATT
561
TGATGAAAAG GCTGGTGGCG CCCAGTTGGG AGTAATGCAA
601
GGACCAATGG GCCCCATGGG ACCTCGAGGA CCTCCAGGCC
641
CTGCAGGTGC TCCTGGGCCT CAAGGATTTC AAGGCAATCC
681
TGGTGAACCT GGTGAACCTG GTGTCTCTGG TCCCATGGGT
721
CCCCGTGGTC CTCCTGGTCC CCCTGGAAAG CCTGGTGATG
761
ATGGTGAAGC TGGAAAACCT GGAAAAGCTG GTGAAAGGGG
801
TCCGCCTGGT CCTCAGGGTG CTCGTGGTTT CCCAGGAACC
841
CCAGGCCTTC CTGGTGTCAA AGGTCACAGA GGTTATCCAG
881
GCCTGGACGG TGCTAAGGGA GAGGCGGGTG CTCCTGGTGT
921
GAAGGGTGAG AGTGGTTCCC CGGGTGAGAA CGGATCTCCG
961
GGCCCAATGG GTCCTCGTGG CCTGCCTGGT GAAAGAGGAC
1001
GGACTGGCCC TGCTGGCGCT GCGGGTGCCC GAGGCAACGA
1041
TGGTCAGCCA GGCCCCGCAG GTCCTCCGG  GTCCTGTCGG
1081
TCCTGCTGGT GGTCCTGGCT TCCCTGGTGC TCCTGGAGCC
1121
AAGGGTGAAG CCGGCCCCAC TGGTGCCCGT GGTCCTGAAG
1161
GTGCTCAAGG TCCTCGCGGT GAACCTGGTA CTCCTGGGTC
1201
CCCTGGGCCT GCTGGTGCCT CCGGTAACCC TGGAACAGAT
1241
GGAATTCCTG GAGCCAAAGG ATCTGCTGGT GCTCCTGGCA
1281
TTGCTGGTGC TCCTGGCTTC CCTGGGCCAC GGGGTCCTCC
1321
TGGCCCTCAA GGTGCAACTG GTCCTCTGGG CCCGAAAGGT
1361
```

Fig. 2

```
CAGACGGGTG AACCTGGTAT TGCTGGCTTC AAAGGTGAAC
1401
AAGGCCCCAA GGGAGAACCT GGCCCTGCTG GCCCCCAGGG
1441
AGCCCCTGGA CCCGCTGGTG AAGAAGGCAA GAGAGGTGCC
1481
CGTGGAGAGC CTGGTGGCGT TGGGCCCATC GGTCCCCCTG
1521
GAGAAAGAGG TGCTCCCGGA AACCGCGGTT TCCCAGGTCA
1561
AGATGGTCTG GCAGGTCCCA AGGGAGCCCC TGGAGAGCGA
1601
GGGCCCAGTG GTCTTGCTGG CCCCAAGGGA GCCAACGGTG
1641
ACCCTGGCCG TCCTGGAGAA CCTGGCCTTC CTGGAGCCCG
1681
GGGTCTCACT GGCCGCCCTG GTGATGCTGG TCCTCAAGGC
1721
AAAGTTGGCC CTTCTGGAGC CCCTGGTGAA GATGGTCGTC
1761
CTGGACCTCC AGGTCCTCAG GGGGCTCGTG GGCAGCCTGG
1801
TGTCATGGGT TTCCCTGGCC CCAAAGGTGC CAACGGTGAG
1841
CCTGGCAAAG CTGGTGAGAA GGGACTGCCT GGTGCTCCTG
1881
GTCTGAGGGG TCTTCCTGGC AAAGATGGTG AGACAGGTGC
1921
TGCAGGACCC CCTGGCCCTG CTGGACCTGC TGGTGAACGA
1961
GGCGAGCAGG GTGCTCCTGG CCATCTGGG TTCCAGGGAC
2001
TTCCTGGCCC TCCTGGTCCC CCAGGTGAAG GTGGAAAACC
2041
AGGTGACCAG GGTGTTCCCG GTGAAGCTGG AGCCCCTGGC
2081
CTCGTGGGTC CCAGGGGTGA ACGAGGTTTC CCAGGTGAAC
2121
GTGGCTCTCC CGGTGCCCAG GGCCTCCAGG GTCCCCGTGG
2161
CCTCCCCGGC ACTCCTGGCA CTGATGGTCC CAAAGGTGCA
2201
TCTGGCCCAG CAGGCCCCCC TGGCGCACAG GGCCCTCCAG
2241
GTCTTCAGGG AATGCCTGGC GAGAGGGGAG CAGCTGGTAT
2281
CGCTGGGCCC AAAGGCGACA GGGGTGACGT TGGTGAGAAA
2321
GGCCCTGAGG GAGCCCCTGG AAAGGATGGT GGACGAGGCC
2361
TGACAGGTCC CATTGGCCCC CCTGGCCCAG CTGGTGCTAA
2401
CGGCGAGAAG GGAGAAGTTG GACCTCCTGG TCCTGCAGGA
2441
AGTGCTGGTG CTCGTGGCGC TCCGGGTGAA CGTGGAGAGA
2481
CTGGCCCCCC CGGACCAGCG GGATTTGCTG GGCCTCCTGG
2521
TGCTGATGGC CAGCCTGGGG CCAAGGGTGA GCAAGGAGAG
2561
GCCGGCCAGA AAGGCGATGC TGGTGCCCCT GGTCCTCAGG
2601
GCCCCTCTGG AGCACCTGGG CCTCAGGGTC CTACTGGAGT
2641
GACTGGTCCT AAAGGAGCCC GAGGTGCCCA AGGCCCCCCG
2681
GGAGCCACTG GATTCCCTGG AGCTGCTGGC CGCGTTGGAC
2721
CCCCAGGCTC CAATGGCAAC CCTGGACCCC CTGGTCCCCC
2761
TGGTCCTTCT GGAAAAGATG GTCCCAAAGG TGCTCGAGGA
```

```
2801
GACAGCGGCC CCCCTGGCCG AGCTGGTGAA CCCGGCCTCC
2841
AAGGTCCTGC TGGACCCCCT GGCGAGAAGG GAGAGCCTGG
2881
AGATGACGGT CCCTCTGGTG CCGAAGGTCC ACCAGGTCCC
2921
CAGGGTCTGG CTGGTCAGAG AGGCATCGTC GGTCTGCCTG
2961
GGCAACGTGG TGAGAGAGGA TTCCCTGGCT TGCCTGGCCC
3001
ATCGGGTGAG CCCGGCAAGC AGGGTGCTCC TGGAGCATCT
3041
GGAGACAGAG GTCCTCCTGG CCCCGTGGGT CCTCCTGGCC
3081
TGACGGGTCC TGCAGGTGAA CCCGGACGAG AGGGAAGCCC
3121
CGGTGCTGAT GGCCCCCCTG GCAGAGATGG CGCTGCTGGA
3161
GTCAAGGGTG ATCGTGGTGA GACTGGTGCT GTGGGAGCTC
3201
CTGGAGCCCC TGGGCCCCCT GGCTCCCCTG GCCCCGCTGG
3241
TCCAACTGGC AAGCAAGGAG ACAGAGGAGA AGCTGGTGCA
3281
CAAGGCCCCA TGGGACCCTC AGGACCAGCT GGAGCCCGGG
3321
GAATCCAGGG TCCTCAAGGC CCCAGAGGTG ACAAAGGAGA
3361
GGCTGGAGAG CCTGGCGAGA GAGGCCTGAA GGGACACCGT
3401
GGCTTCACTG GTCTGCAGGG TCTGCCCGGC CCTCCTGGTC
3441
CTTCTGGAGA CCAAGGTGCT TCTGGTCCTG CTGGTCCTTC
3481
TGGCCCTAGA GGTCCTCCTG GCCCCGTCGG TCCCTCTGGC
3521
AAAGATGGTG CTAATGGAAT CCCTGGCCCC ATTGGGCCTC
3561
CTGGTCCCCG TGGACGATCA GGCGAAACCG GTCCTGCTGG
3601
TCCTCCTGGA AATCCTGGGC CCCTGGTCC TCCAGGTCCC
3641
CCTGGCCCTG GCATCGACAT GTCCGCCTTT GCTGGCTTAG
3681
GCCCGAGAGA GAAGGGCCCC GACCCCTGC AGTACATGCG
3721
GGCCGACCAG GCAGCCGGTG GCCTGAGACA GCATGACGCC
3761
GAGGTGGATG CCACACTCAA GTCCCTCAAC AACCAGATTG
3801
AGAGCATCCG CAGCCCCGAG GGCTCCCGCA AGAACCCTGC
3841
TCGCACCTGC AGAGACCTGA AACTCTGCCA CCCTGAGTGG
3881
AAGAGTGGAG ACTACTGGAT TGACCCCAAC CAAGGCTGCA
3921
CCTTGGACGC CATGAAGGTT TTCTGCAACA TGGAGACTGG
3961
CGAGACTTGC GTCTACCCCA ATCCAGCAAA CGTTCCCAAG
4001
AAGAACTGGT GGAGCAGCAA GAGCAAGGAG AAGAAACACA
4041
TCTGGTTTGG AGAAACCATC AATGGTGGCT TCCATTTCAG
4081
CTATGGAGAT GACAATCTGG CTCCCAACAC TGCCAACGTC
4121
CAGATGACCT TCCTACGCCT GCTGTCCACG GAAGGCTCCC
4161
AGAACATCAC CTACCACTGC AAGAACAGCA TTGCCTATCT
4201
```

```
       GGACGAAGCA GCTGGCAACC TCAAGAAGGC CCTGCTCATC
       4241
       CAGGGCTCCA ATGACGTGGA GATCCGGGCA GAGGGCAATA
       4281
       GCAGGTTCAC GTACACTGCC CTGAAGGATG GCTGCACGAA
       4321
       ACATACCGGT AAGTGGGGCA AGACTGTTAT CGAGTACCGG
       4361
       TCACAGAAGA CCTCACGCCT CCCCATCATT GACATTGCAC
       4401
       CCATGGACAT AGGAGGGCCC GAGCAGGAAT TCGGTGTGGA
       4441
```

*Fig. 2* (cont'd)    `CATAGGGCCG GTCTGCTTCT TGTAA   (SEQ ID NO:2)`

Non-transgenic

■ PBS
○ CII(256-270)
◇ CII(256-264Hyl-270)
△ CII(256-264GHyl-270)

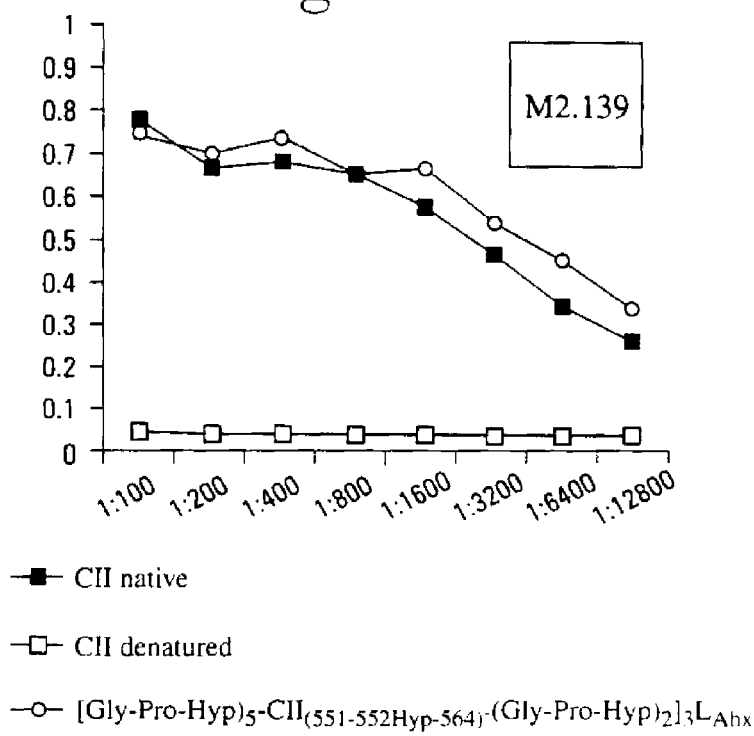
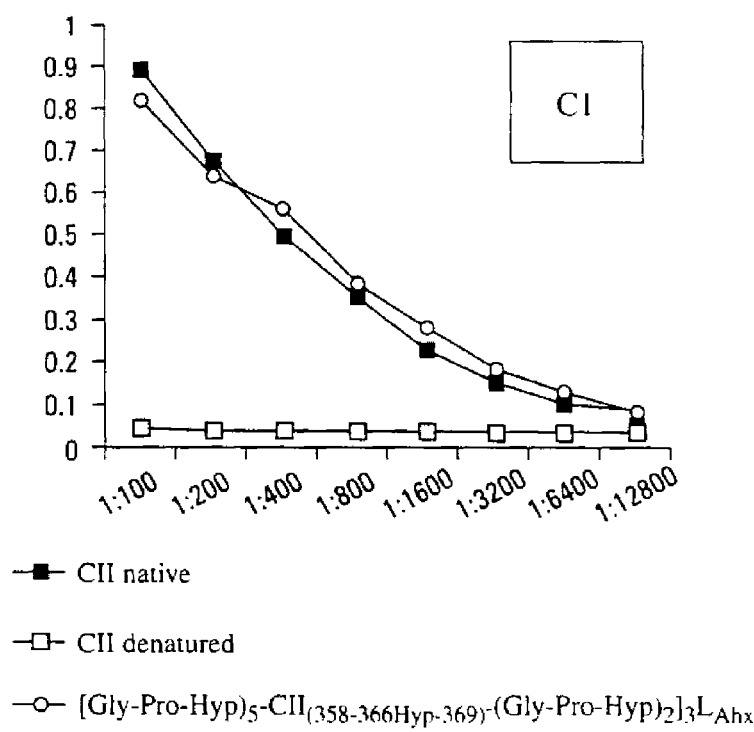
Fig. 8

Fig. 15

Arthritis statistics

| | | Day 68 | | Day 133 | | ΣInc | MMS | MDO |
|---|---|---|---|---|---|---|---|---|
| | | Inc | AUC | Inc | AUC | | | |
| a) non-Tx | CQ (7) | 6/7 (86%) | 87 ±59 | - | - | 6/7 (86%) | 5.8 ±0.8 | 49 ±12 |
| | TSC (9) | 2/9 (22%) p=0.041 | 13 ±30 p=0.007 | - | - | 2/9 (22%) p=0.041 | 5.0 ±0 p=0.144 | 52 ±15 p=0.483 |
| b) non-Tx | CQ (12) | 11/12 (92%) | 431 ±232 | - | - | 11/12 (92%) | 26.5 ±10.0 | 45 ±12 |
| | TSC (19) | 6/17 (35%) p=0.003 | 82 ±163 p=0.001 | - | - | 6/17 (35%) p=0.003 | 20.0 ±10.9 p=0.13 | 50 ±13 p=0.433 |
| c) non-Tx | CQ (7) | 7/7 (100%) | 394 ±213 | 7/7 (100%) | 1761 ±700 | 7/7 (100%) | 35.4 ±15.0 | 41 ±7 |
| | TSC (10) | 2/10 (20%) p=0.002 | 65 ±145 p=0.003 | 7/10 (70%) p=0.228 | 543 ±657 p=0.005 | 9/10 (90%) p=0.999 | 19.8 ±8.4 p=0.019 | 88 ±31 p=0.004 |
| d) Tx | CQ (14) | 10/14 (71%) | 399 ±367 | 12/14 (86%) | 1400 ±1052 | 12/14 (86%) | 33.6 ±15.4 | 52 ±24 |
| | TSC (14) | 5/14 (36%) p=0.128 | 152 ±294 p=0.053 | 10/14 (71%) p=0.648 | 936 ±831 p=0.140 | 11/14 (79%) p=0.999 | 26.5 ±10.3 p=0.135 | 74 ±30 p=0.042 |

Fig. 16
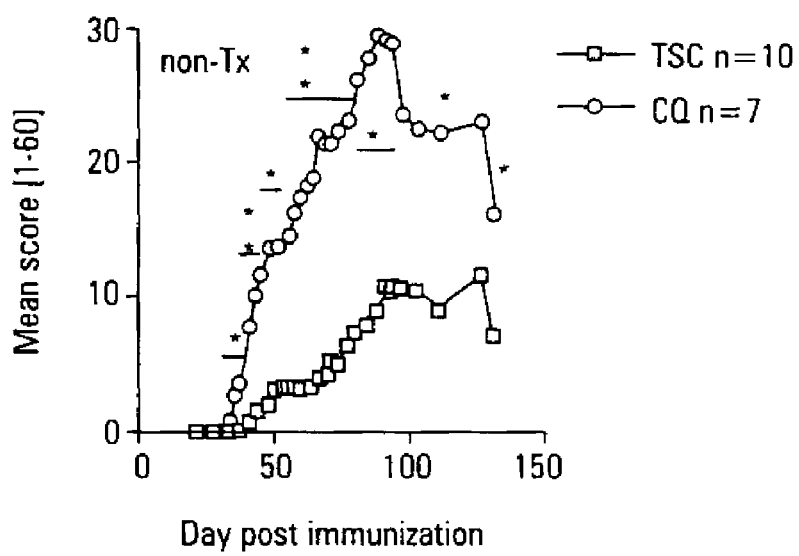
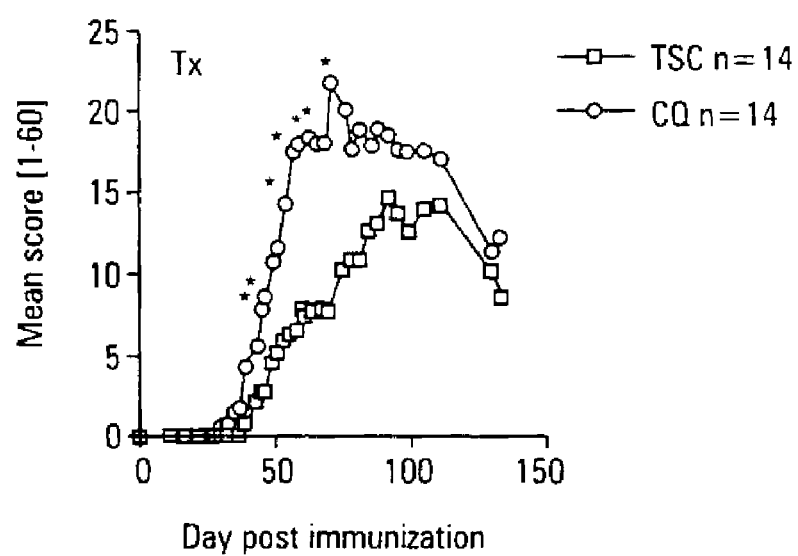

Fig. 17

TSC skin IgG-titers

|  |  | Day 35 |  |  | Day 68-72 |  |  |  | Day 133 |  |  |  |
|---|---|---|---|---|---|---|---|---|---|---|---|---|
|  |  | IgG | IgG1 | IgG2a | IgG2a/IgG1 | IgG | IgG1 | IgG2a | IgG2a/IgG1 | IgG | IgG1 | IgG2a | IgG2a/IgG1 |
| non-Tx | CQ (7) | 330 | 41 | 177 | 12 | 947 | 8 | 149 | 51 | - | - | - | - |
|  | TSC (9) | 183 $p=0.153$ | 18 $p=0.266$ | 69 $p=0.023$ | 5 $p=0.368$ | 524 $p=0.132$ | 4 $p=0.543$ | 104 $p=0.247$ | 53 $p=0.043$ | - | - | - | - |
| non-Tx | CQ (12) | 464 | 38 | 223 | 7 | 464 | 16 | 155 | 12 | - | - | - | - |
|  | TSC (17) | 169 $p<0.0001$ | 38 $p<0.352$ | 71 $p<0.0001$ | 5 $p=0.051$ | 90 $p=0.0001$ | 15 $p=0.215$ | 44 $p=0.0005$ | 4 $p=0.0005$ | - | - | - | - |
| non-Tx | CQ (7) | 354 | 12 | 93 | 10 | 501 | 12 | 142 | 11 | 501 | 10 | 60 | 6 |
|  | TSC (10) | 224 $p=0.079$ | 8 $p=0.154$ | 63 $p=0.097$ | 10 $p=0.922$ | 350 $p=0.494$ | 9 $p=0.329$ | 105 $p=0.283$ | 10 $p=0.494$ | 314 $p=0.494$ | 10 $p=0.380$ | 50 $p=0.558$ | 6 $p=0.205$ |
| Σnon-Tx | CQ (26) | 398 | 32 | 176 | 9 | 604 | 12 | 150 | 22 | 501 | 10 | 68 | 6 |
|  | TSC (36) | 185 $p<0.0001$ | 24 $p=0.055$ | 68 $p<0.0001$ | 6 $p=0.047$ | 263 $p=0.001$ | 11 $p=0.470$ | 75 $p=0.0002$ | 17 $p=0.011$ | 314 $p=0.494$ | 10 $p=0.380$ | 58 $p=0.558$ | 6 $p=0.205$ |
| ΣTx | CQ (14) | 445 | 10 | 49 | 14 | 330 | 4 | 44 | 35 | 508 | 9 | 67 | 15 |
|  | TSC (14) | 133 $p=0.001$ | 8 $p=0.783$ | 18 $p=0.0003$ | 5 $p=0.022$ | 168 $p=0.024$ | 4 $p=0.383$ | 19 $p=0.004$ | 6 $p=0.003$ | 195 $p=0.010$ | 6 $p=0.648$ | 32 $p=0.017$ | 6 $p=0.118$ |
| Control | TSC-Tg.(6) | 116 | 1 | 10 | - | 82 | 1 | 9 | - | 42 | 1 | 6 | - |

```
1.........x..........x..........x..........x..........L..........x..........x..........x
GPMGPMGPRGPPGPAGAPGPQGFQGNPGEPGEPGVSGPMGPRGPPGPAGKPGDDGEAGKPGKSGERGLPGPQGARGFPGT
.................................................P..............A....P............
                                                 "E41"
..........x.........C.........x..........x..........x..........x..........L..........x
PGLPGVKGHRGYPGLDGAKGEAGAPGVKGESGSPGENGSPGPMGPRGLPGERGRTGPAGAAGARGNDGQPGPAGPPGPVG
..................................................................................

"TD1"                            "E17"
..........x..........x..........x........C..........x..........x..........x..........x
PAGGPGFPGAPGAKGEAGPTGARGPEGAQGSRGEPGNPGSPGPAGASGNPGTDGIPGAKGSAGAPGIAGAPGFPGPRGPP
..................P.....T..........................................................

"T1"
.........L..........x..........x..........x..........x.........C..........x..........x
GPQGATGPLGPKGQAGEPGIAGFKGDQGPKGETGPAGPQGAPGPAGEEGKRGARGEPGGAGPIGPPGERGAPGNRGFPGQ
........T............E........P................................V..................

"D8"      "TD8"
..........x..........x.........L..........x..........x..........x..........x........C
DGLAGPKGAPGERGPSGLAGPKGANGDPGRPGEPGLPGARGLTGRPGDAGPQGKVGPSGAPGEDGRPGPPGPQGARGQPG
....................................................................................

..........x..........x..........x..........x.........L..........x..........x..........x
VMGFPGPKGANGEPGKAGEKGLAGAPGLRGLPGKDGETGAAGPPGPSGPAGERGEQGAPGPSGFQGLPGPPGPPGEGGKQ
..................................P....................A...........................P
          "U1"                                                                "J1"
..........x........C..........x..........x..........x..........x..........L..........x
GDQGIPGEAGAPGLVGPRGERGFPGERGSPGAQGLQGPRGLPGTPGTDGPKGAAGPDGPPGAQGPPGLQGMPGERGAAGI
....V.........................................................S..A................

..........x..........x..........x.........C..........x..........x..........x..........x
AGPKGDRGDVGEKGPEGAPGKDGGRGLTGPIGPPGPAGANGEKGEVGPPGPSGSTGARGAPGEPGETGPPGPAGFAGPPG
..............................................................A..A................

"D3"
..........L..........x..........x..........x..........x.........C..........x..........x
ADGQPGAKGDQGEAGQKGDAGAPGPQGPSGAPGPQGPTGVTGPKGARGAQGPPGATGFPGAAGRVGPPGPGANGNPGAGPP
........E............................................................S......P....

"E10"
..........x..........x.........L..........x..........x..........x..........x.........C
GPAGKDGPKGVRGDSGPPGRAGDPGLQGPAGAPGEKGEPGDDGPSGLDGPPGPQGLAGQRGIVGLPGQRGERGFPGLPGP
..S.......A.........E........P.................AE..................................

..........x..........x..........x..........x.........L..........x..........x..........x
SGEPGKQGAPGASGDRGPPGPVGPPGLTGPAGEPGREGSPGADGPPGRDGAAGVKGDRGETGALGAPGAPGPPGSPGPAG
......................................................................V...........
                                                  "F4"
..........x..........x..........x..........x..........x..........x..........L..........x
PTGKQGDRGEAGAQGPMGPSGPAGARGIAGPQGPRGDKGESGEQGERGLKGHRGFTGLQGLPGPPGPSGDQGASGPAGPS
..................................Q..........................A..P.................

..........x..........x..........x.........C..........x....
GPRGPPGPVGPSGKDGSNGIPGPIGPPGPRGRSGETGPVGPPGSPGPPGPPGPP    (SEQ ID NO:48)
..................A.................A....N..........    (SEQ ID NO:1)
                              Fig. 19
```

```
1
ATGATTCGCC TCGGGGCTCC CCAGTCGCTG GTGCTGCTGA
41
CGCTGCTCGT CGCCGCTGTC CTTCGGTGTC AGGGCCAGGA
81
TGTCCAGGAG GCTGGCAGCT GTGTGCAGGA TGGGCAGAGG
121
TATAATGATA AGGATGTGTG GAAGCCGGAG CCCTGCCGGA
161
TCTGTGTCTG TGACACTGGG ACTGTCCTCT GCGACGACAT
201
AATCTGTGAA GACGTGAAAG ACTGCCTCAG CCCTGAGATC
241
CCCTTCGGAG AGTGCTGCCC CATCTGCCCA ACTGACCTCG
281
CCACTGCCAG TGGGCAACCA GGACCAAAGG GACAGAAAGG
321
AGAACCTGGA GACATCAAGG ATATTGTAGG ACCCAAAGGA
361
CCTCCTGGGC CTCAGGGACC TGCAGGGGAA CAAGGACCCA
401
GAGGGGATCG TGGTGACAAA GGTGAAAAAG GTGCCCCTGG
441
ACCTCGTGGC AGAGATGGAG AACCTGGGAC CCCTGGAAAT
481
CCTGGCCCCC CTGGTCCTCC CGGCCCCCCT GGTCCCCCTG
521
GTCTTGGTGG AAACTTTGCT GCCCAGATGG CTGGAGGATT
561
TGATGAAAAG GCTGGTGGCG CCCAGTTGGG AGTAATGCAA
601
GGACCAATGG GCCCCATGGG ACCTCGAGGA CCTCCAGGCC
641
CTGCAGGTGC TCCTGGGCCT CAAGGATTTC AAGGCAATCC
681
TGGTGAACCT GGTGAACCTG GTGTCTCTGG TCCCATGGGT
721
CCCCGTGGTC CTCCTGGTCC CCCTGGAAAG CCTGGTGATG
761
ATGGTGAAGC TGGAAAACCT GGAAAAGCTG GTGAAGGGG
801
TCCGCCTGGT CCTCAGGGTG CTCGTGGTTT CCCAGGAACC
841
CCAGGCCTTC CTGGTGTCAA AGGTCACAGA GGTTATCCAG
881
GCCTGGACGG TGCTAAGGGA GAGGCGGGTG CTCCTGGTGT
```

*Fig.* 20

```
921
GAAGGGTGAG AGTGGTTCCC CGGGTGAGAA CGGATCTCCG
961
GGCCCAATGG GTCCTCGTGG CCTGCCTGGT GAAAGAGGAC
            G    P   R   G   L   P   G   E   R   G
1001
GGACTGGCCC TGCTGGCGCT GCGGGTGCCC GAGGCAACGA
  R  T  G  P  A  G  A   A  G
1041
TGGTCAGCCA GGCCCCGCAG GTCCTCCGG GTCCTGTCGG
1081
TCCTGCTGGT GGTCCTGGCT TCCCTGGTGC TCCTGGAGCC
1121
AAGGGTGAAG CCGGCCCAC TGGTGCCCGT GGTCCTGAAG
                        A  R   G  P   E
1161
GTGCTCAAGG TCCTCGCGGT GAACCTGGTA CTCCTGGGTC
 G A Q G  P R
1201
CCCTGGGCCT GCTGGTGCCT CCGGTAACCC TGGAACAGAT
                       G  N  P   G  T  D
1241
GGAATTCCTG GAGCCAAAGG ATCTGCTGGT GCTCCTGGCA
  G  I  P   G  A  K  G
1281
TTGCTGGTGC TCCTGGCTTC CCTGGGCCAC GGGGTCCTCC
1321
TGGCCCTCAA GGTGCAACTG GTCCTCTGGG CCCGAAAGGT
1361
CAGACGGGTG AACCTGGTAT TGCTGGCTTC AAAGGTGAAC
                   G  I  A  G  F   K  G  E
1401
AAGGCCCCAA GGGAGAACCT GGCCCTGCTG GCCCCAGGG
 Q G  P  K   G  E  P  G
1441
AGCCCCTGGA CCCGCTGGTG AAGAAGGCAA GAGAGGTGCC
1481
CGTGGAGAGC CTGGTGGCGT TGGGCCCATC GGTCCCCTG
1521
GAGAAAGAGG TGCTCCCGGA AACCGCGGTT TCCCAGGTCA
1561
AGATGGTCTG GCAGGTCCCA AGGGAGCCCC TGGAGAGCGA
1601
GGGCCCAGTG GTCTTGCTGG CCCCAAGGGA GCCAACGGTG
1641
ACCCTGGCCG TCCTGGAGAA CCTGGCCTTC CTGGAGCCCG
                                   G  A  R
```

*Fig. 20 (cont'd)*

```
1681
GGGTCTCACT GGCCGCCCTG GTGATGCTGG TCCTCAAGGC
  G   L   T    G   R   P    G   D   A    P   Q   G
1721
AAAGTTGGCC CTTCTGGAGC CCCTGGTGAA GATGGTCGTC
  K   V   G   P    S   G   A    P
1761
CTGGACCTCC AGGTCCTCAG GGGGCTCGTG GGCAGCCTGG
1801
TGTCATGGGT TTCCCTGGCC CCAAAGGTGC AACGGTGAG
1841
CCTGGCAAAG CTGGTGAGAA GGGACTGCCT GGTGCTCCTG
1881
GTCTGAGGGG TCTTCCTGGC AAAGATGGTG AGACAGGTGC
1921
TGCAGGACCC CCTGGCCCTG CTGGACCTGC TGGTGAACGA
1961
GGCGAGCAGG GTGCTCCTGG CCATCTGGG TTCCAGGGAC
2001
TTCCTGGCCC TCCTGGTCCC CCAGGTGAAG GTGGAAAACC
2041
AGGTGACCAG GGTGTTCCCG GTGAAGCTGG AGCCCCTGGC
2081
CTCGTGGGTC CCAGGGGTGA ACGAGGTTTC CCAGGTGAAC
  L   V   G   P    R   G   E    R   G   F    P
2121
GTGGCTCTCC CGGTGCCCAG GGCCTCCAGG GTCCCCGTGG
2161
CCTCCCCGGC ACTCCTGGCA CTGATGGTCC CAAAGGTGCA
2201
TCTGGCCCAG CAGGCCCCCC TGGCGCACAG GGCCCTCCAG
2241
GTCTTCAGGG AATGCCTGGC GAGAGGGGAG CAGCTGGTAT
               M   P   G   E    R   G   A    A   G   I
2281
CGCTGGGCCC AAAGGCGACA GGGGTGACGT TGGTGAGAAA
  A   G   P
2321
GGCCCTGAGG GAGCCCCTGG AAAGGATGGT GGACGAGGCC
2361
TGACAGGTCC CATTGGCCCC CCTGGCCCAG CTGGTGCTAA
2401
CGGCGAGAAG GGAGAAGTTG GACCTCCTGG TCCTGCAGGA
2441
AGTGCTGGTG CTCGTGGCGC TCCGGGTGAA CGTGGAGAGA
2481
```

*Fig. 20* (cont'd)

CTGGCCCCCC CGGACCAGCG GGATTTGCTG GGCCTCCTGG
2521
TGCTGATGGC CAGCCTGGGG CCAAGGGTGA GCAAGGAGAG
2561
GCCGGCCAGA AAGGCGATGC TGGTGCCCCT GGTCCTCAGG
2601
GCCCCTCTGG AGCACCTGGG CCTCAGGGTC CTACTGGAGT
2641
GACTGGTCCT AAAGGAGCC<u>C GAGGTGCCCA AGGCCCCCG</u>
                          R   G   A   Q    G   P   P
2681
<u>GGAGCCACTG GATTC</u>CCTGG AGCTGCTGGC CGCGTTGGAC
 G   A   T   G   F
2721
CCCCAGGCTC CAATGCAAC CCTGGACCCC CTGGTCCCCC
2761
TGGTCCTTCT GGAAAAGATG GTCCCAAAGG TGCTCGAGGA
2801
GACAGCGGCC CCCTGGCCG AGCTGGTGAA CCCGGCCTCC
2841
AAGGTCCTGC TGGACCCCCT GGCGAGAAGG GAGAGCCTGG
2881
AGATGACGGT CCCTCTGGTG CCGAAGGTCC ACCAGGTCCC
2921
CAGGGTCTGG <u>CTGGTCAGAG AGGCATCGTC</u> GGTCTGCCTG
         A   G   Q   R    G   I   V
2961
GGCAACGTGG TGAGAGAGGA TTCCCTGGCT TGCCTGGCCC
3001
ATCGGGTGAG CCCGGCAAGC AGGGTGCTCC TGGAGCATCT
3041
GGAGACAGAG GTCCTCCTGG CCCCGTGGGT CCTCCTGGCC
3081
TGACGGGTCC TGCAGGTGAA CCCGGACGAG AGGGAAGCCC
3121
CGGTGCTGAT GGCCCCCTG GCAGAGATGG CGCTGCTGGA
3161
GTCAAGGGTG ATCGTGGTGA GACTGGTGCT GTGGGAGCTC
3201
CTGGAGCCCC TGGGCCCCT GGCTCCCCTG GCCCCGCTGG
3241
TCCAACTGGC AAGCAAGGAG ACAGAGGAGA AGCTGGTGCA
3281
CAAGGCCCCA TGGGACCCTC AGGACCAGCT GGAGCCCGGG
3321
GAATCCAGGG TCCTCAAGGC CCCAGAGGTG ACAAAGGAGA
3361

*Fig. 20* *(cont'd)*

```
       GGCTGGAGAG CCTGGCGAGA GAGGCCTGAA GGGACACCGT
                                            H   R
3401
       GGCTTCACTG GTCTGCAGGG TCTGCCCGGC CCTCCTGGTC
        G   F  T
3441
       CTTCTGGAGA CCAAGGTGCT TCTGGTCCTG CTGGTCCTTC
3481
       TGGCCCTAGA GGTCCTCCTG GCCCCGTCGG TCCCTCTGGC
3521
       AAAGATGGTG CTAATGGAAT CCCTGGCCCC ATTGGGCCTC
3561
       CTGGTCCCCG TGGACGATCA GGCGAAACCG GTCCTGCTGG
3601
       TCCTCCTGGA AATCCTGGGC CCCTGGTCC TCCAGGTCCC
3641
       CCTGGCCCTG GCATCGACAT GTCCGCCTTT GCTGGCTTAG
3681
       GCCCGAGAGA GAAGGGCCCC GACCCCTGC AGTACATGCG
3721
       GGCCGACCAG GCAGCCGGTG GCCTGAGACA GCATGACGCC
3761
       GAGGTGGATG CCACACTCAA GTCCCTCAAC AACCAGATTG
3801
       AGAGCATCCG CAGCCCCGAG GGCTCCCGCA AGAACCCTGC
3841
       TCGCACCTGC AGAGACCTGA AACTCTGCCA CCCTGAGTGG
3881
       AAGAGTGGAG ACTACTGGAT TGACCCCAAC CAAGGCTGCA
3921
       CCTTGGACGC CATGAAGGTT TTCTGCAACA TGGAGACTGG
3961
       CGAGACTTGC GTCTACCCCA ATCCAGCAAA CGTTCCCAAG
4001
       AAGAACTGGT GGAGCAGCAA GAGCAAGGAG AAGAAACACA
4041
       TCTGGTTTGG AGAAACCATC AATGGTGGCT TCCATTTCAG
4081
       CTATGGAGAT GACAATCTGG CTCCCAACAC TGCCAACGTC
4121
       CAGATGACCT TCCTACGCCT GCTGTCCACG GAAGGCTCCC
4161
       AGAACATCAC CTACCACTGC AAGAACAGCA TTGCCTATCT
4201
       GGACGAAGCA GCTGGCAACC TCAAGAAGGC CCTGCTCATC
4241
       CAGGGCTCCA ATGACGTGGA GATCCGGGCA GAGGGCAATA
```

*Fig. 20 (cont'd)*

```
4281
GCAGGTTCAC GTACACTGCC CTGAAGGATG GCTGCACGAA
4321
ACATACCGGT AAGTGGGGCA AGACTGTTAT CGAGTACCGG
4361
TCACAGAAGA CCTCACGCCT CCCCATCATT GACATTGCAC
4401
CCATGGACAT AGGAGGGCCC GAGCAGGAAT TCGGTGTGGA
4441
CATAGGGCCG GTCTGCTTCT TGTAA    (SEQ ID NO:2)
```

*Fig. 20* (cont'd)

Scheme 1

Scheme 2

TRIPLE POLYPEPTIDE COMPLEXES

CROSS-REFERENCE TO RELATED APPLICATIONS

This application claims priority to U.S. application Ser. No. 60/305,048, which was filed on Jul. 12, 2001.

BACKGROUND

1. Technical Field

The invention relates to methods and materials involved in assessing and treating autoimmune conditions such as rheumatoid arthritis.

2. Background Information

Rheumatoid arthritis (RA) is an autoimmune, inflammatory disease that affects peripheral joints. The main genetic association is to the major histocompatibility complex class II region (HLA-DR), suggesting that T cell mediated autoimmune recognition of joint specific antigens is involved in the disease. In addition, B cell mediated autoimmune responses have been observed in rheumatoid joints. Specifically, B cells have been detected secreting IgG antibodies specific for type II collagen (CII). Further, mice transgenic for a particular human DR4 molecule were found to develop arthritis after immunization with CII. The T cell response in these immunized mice was predominantly directed towards one dominant epitope corresponding to the amino acid sequence at positions 261–273 of CII.

The collagens are a family of highly fibrous proteins, including fibril-forming, fibril-associated, and network-forming collagen types. CII is a fibril-forming collagen that serves as a major component of bone, cartilage, invertebral disc, notochord, and vitreous humor. Additionally, CII plays an important role in the development of RA.

SUMMARY

The invention involves methods and materials for assessing and treating autoimmune conditions such as rheumatoid arthritis. Specifically, the invention provides polypeptide compositions, nucleic acids, substantially pure polypeptides, host cells, and methods for identifying mammals with autoimmune conditions, treating mammals with autoimmune conditions, and enhancing tolerance in mammals with autoimmune conditions.

In general, the invention features a composition containing three polypeptides, wherein each polypeptide contains a triple helix formation sequence, and wherein each polypeptide contains at least two interpolypeptide linkages such that each polypeptide is covalently attached to at least one of the other two polypeptides of the three polypeptides. The triple helix formation sequence of at least one of the three polypeptides can contain (Gly-Pro-Hyp). The triple helix formation sequence of at least one of the three polypeptides can contain (Gly-Pro-Flp). At least one of the interpolypeptide linkages can include an Ahx-Lys bond. At least one of the interpolypeptide linkages can include a Cys-Cys bond. At least one of the three polypeptides can contain a (Gly-Xaa-Yaa)$_n$ sequence, the n being an integer from 1 to 100. At least one of the three polypeptides can contain a (Gly-Pro-Hyp)$_x$(Gly-Xaa-Yaa)$_y$(Gly-Pro-Hyp)$_z$ sequence, wherein the x, y, and z are independently integers from 1 to 100. At least one of the interpolypeptide linkages for each polypeptide can be located in an N-terminal region. At least one of the interpolypeptide linkages for each polypeptide can be located in a C-terminal region. At least one of the interpolypeptide linkages for each polypeptide can be located in an N-terminal region, and at least one of the interpolypeptide linkages for each polypeptide can be located in a C-terminal region. At least one of the three polypeptides can be covalently attached to the other two polypeptides of the three polypeptides. Each polypeptide can be covalently attached to the other two polypeptides of the three polypeptides. At least one of the three polypeptides can contain a modified amino acid residue (e.g., a glycosylated amino acid residue). Each polypeptide can contain a modified amino acid residue. At least one of the three polypeptides can contain an amino acid sequence at least about 80 percent identical to the sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56. Each polypeptide can contain an amino acid sequence at least about 80 percent identical to the sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56.

In another embodiment, the invention features a composition containing three polypeptides, wherein each polypeptide contains a triple helix formation sequence, wherein each polypeptide contains at least one interpolypeptide linkage such that each polypeptide is attached to at least one of the other two polypeptides of the three polypeptides, and wherein at least one of the three polypeptides contains an amino acid sequence at least about 80 percent identical to the sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56. The triple helix formation sequence of at least one of the three polypeptides can contain (Gly-Pro-Hyp). The triple helix formation sequence of at least one of the three polypeptides can contain (Gly-Pro-Flp). At least one of the interpolypeptide linkages can contain an Ahx-Lys bond. At least one of the interpolypeptide linkages can contain a Cys-Cys bond. At least one of the three polypeptides can contain a (Gly-Xaa-Yaa)$_n$ sequence, the n being an integer from 1 to 100. At least one of the three polypeptides can contain a (Gly-Pro-Hyp)$_x$(Gly-Xaa-Yaa)$_y$(Gly-Pro-Hyp)$_z$ sequence, wherein the x, y, and z are independently integers from 1 to 100. At least one of the interpolypeptide linkages for each polypeptide can be located in an N-terminal region. At least one of the interpolypeptide linkages for each polypeptide can be located in a C-terminal region. At least one of the interpolypeptide linkages for each polypeptide can be located in an N-terminal region, and at least one of the interpolypeptide linkages for each polypeptide can be located in a C-terminal region. At least one of the three polypeptides can be covalently attached to the other two polypeptides of the three polypeptides. Each polypeptide can be covalently attached to the other two polypeptides of the three polypeptides. At least one of the three polypeptides can contain a modified amino acid residue (e.g., a glycosylated amino acid residue). Each polypeptide can contain a modified amino acid residue. Each polypeptide can contain at least two interpolypeptide linkages.

Another embodiment of the invention features a composition containing three polypeptides, wherein each polypeptide contains a triple helix formation sequence, wherein each polypeptide contains at least one interpolypeptide linkage such that each polypeptide is covalently attached to at least one of the other two polypeptides of the three polypeptides, and wherein at least one of the three polypeptides contains a modified amino acid residue. The modified amino acid residue can be a glycosylated amino acid residue. The modified amino acid residue can be a modified lysine residue. The modified amino acid residue can be lysine-dinitrophenyl. At least one of the three polypeptides can contain an amino acid sequence at least about 80 percent identical to the sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56. Each polypeptide can contain an amino acid sequence at least about 80 percent identical to the sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56.

Another embodiment of the invention features a composition containing three polypeptides, wherein each polypeptide contains at least one interpolypeptide linkage such that each polypeptide is attached to at least one of the other two polypeptides of the three polypeptides, and wherein at least one polypeptide of the three polypeptides contains (Gly-Pro-Flp). Each polypeptide of the three polypeptides can contain (Gly-Pro-Flp). At least one of the three polypeptides can contain an amino acid sequence at least about 80 percent identical to the sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56. Each polypeptide can contain an amino acid sequence at least about 80 percent identical to the sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56.

In another aspect, the invention features a method for detecting an antibody in a sample from a mammal (e.g., human), wherein the antibody has specificity for a triple polypeptide complex, wherein the triple polypeptide complex contains three polypeptides, wherein each of the three polypeptides contains a triple helix formation sequence, wherein each of the three polypeptides contains at least one interpolypeptide linkage such that each polypeptide is attached to at least one of the other two polypeptides of the three polypeptides, and wherein (i) each polypeptide contains at least two interpolypeptide linkages; (ii) at least one polypeptide of the three polypeptides contains an amino acid sequence at least about 80 percent identical to the sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56; (iii) at least one polypeptide of the three polypeptides contains a modified amino acid residue; or (iv) at least one polypeptide of the three polypeptides contains (Gly-Pro-Flp); the method including: (a) contacting the sample with the triple polypeptide complex, and (b) determining the presence or absence of the antibody bound to the triple polypeptide complex, wherein the presence of bound antibody indicates that the sample contains the antibody. The sample can be serum. The antibody can be an anti-collagen antibody. The antibody can be bound to a B-cell. The antibody can be a circulating antibody.

In another embodiment, the invention features a method for detecting a T-cell in a sample from a mammal (e.g., human), wherein the T-cell is reactive to a triple polypeptide complex, wherein the triple polypeptide complex contains three polypeptides, wherein each of the three polypeptides contains a triple helix formation sequence, wherein each of the three polypeptides contains at least one interpolypeptide linkage such that each polypeptide is attached to at least one of the other two polypeptides of the three polypeptides, and wherein: (i) each polypeptide contains at least two interpolypeptide linkages; (ii) at least one polypeptide of the three polypeptides contains an amino acid sequence at least about 80 percent identical to the sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56; (iii) at least one polypeptide of the three polypeptides contains a modified amino acid residue; or (iv) at least one polypeptide of the three polypeptides contains (Gly-Pro-Flp); the method including: (a) contacting the sample with the triple polypeptide complex, and (b) determining the presence or absence of T-cell activation, wherein the presence of the T-cell activation indicates that the sample contains the T-cell. The sample can be a blood sample. The T-cell can be a CD4$^+$ T-cell.

Another aspect of the invention features a method of enhancing, in a mammal, tolerance to an endogenous polypeptide, the method including administering a composition to the mammal under conditions effective to enhance the tolerance, the composition containing three polypeptides, wherein each of the three polypeptides contains a triple helix formation sequence and at least one interpolypeptide linkage such that each of the three polypeptides is covalently attached to at least one of the other two polypeptides of the three polypeptides. The endogenous polypeptide can be a triple helical polypeptide (e.g., type II collagen). Each of the three polypeptides can contain at least two interpolypeptide linkages. At least one of the three polypeptides can contain an amino acid sequence at least about 80 percent identical to the sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56. At least one of the three polypeptides can contain a modified amino acid residue. At least one polypeptide of the three polypeptides can contain (Gly-Pro-Flp).

Another aspect of the invention features a method of forming, in a mammal, a triple helical polypeptide-antibody complex, the method including administering an antibody to the mammal under conditions effective to form the triple helical polypeptide-antibody complex with a triple helical polypeptide, the antibody having specificity for a triple polypeptide complex, wherein the triple polypeptide complex contains three polypeptides, wherein each polypeptide contains a triple helix formation sequence and at least one interpolypeptide linkage such that each polypeptide is attached to at least one of the other two polypeptides of the three polypeptides, and wherein at least one polypeptide of the three polypeptides contains an amino acid sequence at least about 80 percent identical to the sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56. The triple helical polypeptide can be type II collagen.

In another embodiment, the invention features a method of enhancing, in a mammal, tolerance to an endogenous polypeptide, the method including administering an isolated nucleic acid molecule to a somatic cell of the mammal under conditions effective to enhance the tolerance, wherein the nucleic acid molecule contains a nucleic acid sequence that encodes a polypeptide containing a triple helix formation sequence. The mammal can have arthritis. The endogenous polypeptide can be a triple helical polypeptide (e.g., type II collagen). The somatic cell can be a fibroblast or fibrocyte. The polypeptide can contain an amino acid sequence at least about 80 percent identical to the sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56.

Another embodiment of the invention features a method of enhancing, in a mammal, tolerance to an endogenous polypeptide, the method including administering cells to the mammal under conditions effective to enhance the tolerance, wherein the cells contain an isolated nucleic acid molecule encoding a polypeptide containing a triple helix formation sequence. The mammal can have arthritis. The endogenous polypeptide can be a triple helical polypeptide (e.g., type II collagen). The polypeptide can contain an amino acid sequence at least about 80 percent identical to the sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is a listing of the amino acid sequence of mouse and human CII. The mouse CII amino acid sequence is on top (SEQ ID NO:48), and the human CII amino acid sequence is on the bottom (SEQ ID NO:1). The dots in the human sequence indicate that that amino acid residue is identical to the amino acid residue listed in the mouse CII amino acid sequence.

FIG. 2 is a listing of a nucleic acid sequence that encodes human CII (SEQ ID NO:2).

FIG. 8 is a graph plotting the amount of M2.139 monoclonal antibody binding verses dilution of $[(Gly-Pro-Hyp)_5-CII_{(551-552Hyp-564)}-(Gly-Pro-Hyp)_2]_3L_{Ahx}$ and a graph plotting the amount of C1 monoclonal antibody binding verses dilution of $[(Gly-Pro-Hyp)_5-CII_{(358-366Hyp-369)}-(Gly-Pro-Hyp)_2]_3L_{Ahx}$.

FIG. 15 is a table demonstrating arthritis development in TSC-skin transplanted recipients. Normal (A–C) or thymectomized (D) mice were grafted with skin from either transgenic (TSC) or control littermates (CQ) mice and immunized with CII and adjuvant four weeks later. Five weeks later, all mice were given a boost injection of CII. A second boost was also given 10 weeks after the first immunization (C–D). Abbreviations: Inc, incidence; AUC, area under the curve (of mean arthritis index); MMS, mean maximum score (at the end of experiment); MDO, mean day of onset. Results are given as number of diseased animals and mean values StDev of AUC, MMS and MDO.

FIG. 16 is two graphs representing arthritis indexes of TSC or control grafted mice. Mice were grafted four weeks prior to immunization with CII and adjuvant. Five weeks later, mice were given a boost injection of CII (A–D). A second boost was also given 10 weeks after the first immunization (C–D). In one experiment, mice were also thymectomized 2 weeks prior to skin transplantation (D). *p≦0.05, *p≦0.01, **p<0.001.

FIG. 17 is a table presenting anti-CII antibody titers in skin transplanted mice. The indicated number of mice were either grafted with skin from transgenic (TSC) or negative littermates (CQ) mice. In three separate experiments (A–C), non-thymectomized mice and, in one experiment (E), thymectomized mice were grafted and immunized with CII as described in FIG. 15. After 5, 10, and 19 (only C, E, and F) weeks, blood samples were collected and used to determine anti-CII antibody titers. Non-grafted, euthymic TSC transgenic mice were also immunized as controls (F). The ratio of isotype IgG antibodies (IgG2a/IgG1) are given to compare different experiments separated by time and animal facilities. * Pooled results from three experiments with non-thymectomized mice. Antibody titers measured 19 weeks post immunization only includes animals from experiment C (i.e., n (CQ)=7; n (TSC)=10).

FIG. 19 is a listing of the amino acid sequence of mouse and human CII as presented in FIG. 1 with selected CII epitopes being identified via underline.

FIG. 20 is a listing of the nucleic acid sequence that encodes human CII as presented in FIG. 2 with selected CII epitopes being identified via underline. In addition, the amino acid sequence of each selected CII epitope is provided under the corresponding nucleic acid sequence.

DETAILED DESCRIPTION

Figure 3:
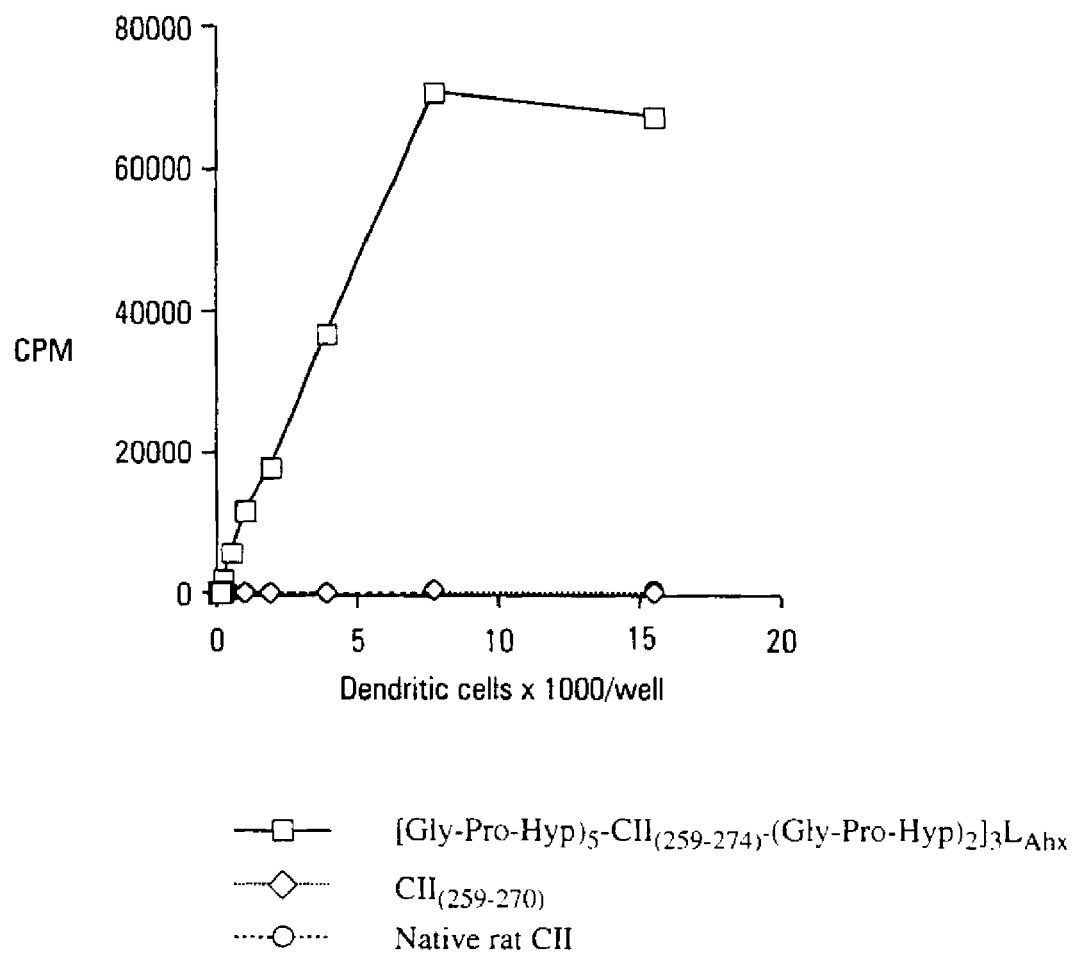
FIG. 3 is a line graph plotting radioactive counts per minute (CPM) versus number of dendritic cells per well for cells treated with 10 µg of $[(Gly-Pro-Hyp)_5-CII_{(259-274)}-(Gly-Pro-Hyp)_2]_3L_{Ahx}$ (linked polypeptide), $CII_{(259-270)}$ (unlinked polypeptides), or native rat CII. The results are given as the means of duplicates.

The invention provides methods and materials related to assessing and treating autoimmune conditions such as rheumatoid arthritis. Specifically, the invention provides polypeptide compositions, nucleic acids, substantially pure polypeptides, host cells, and methods for identifying mammals with autoimmune conditions, treating mammals with autoimmune conditions, and enhancing tolerance in mammals with autoimmune conditions. For the purpose of this invention, the term "autoimmune condition" refers to any condition resulting from a mammal's body tissue being attacked by that mammal's own immune system. For example, a patient with an autoimmune condition can have antibodies in their blood that target their own body tissues. Examples of autoimmune conditions include, without limitation, rheumatoid arthritis, relapsing polychondritis, systemic lupus erythematosus, psoriasis arthritis, anylosing spondylitis, chronic stages of asthma, Sjörgren's syndrome, and multiple sclerosis.

Polypeptide Compositions

The invention provides polypeptide compositions. A polypeptide composition can contain three polypeptides arranged in a triple helical conformation. Additionally, a polypeptide composition can contain three polypeptides with each polypeptide having at least one interpolypeptide linkage such that each polypeptide of the three polypeptides is covalently attached to at least one of the other two polypeptides. The term "interpolypeptide linkage" as used herein refers to any bond or series of bonds that covalently connects two polypeptides. An interpolypeptide linkage can be a bond or series of bonds formed between the side group of a unit from one polypeptide and the side group of a unit from the other polypeptide. Any linkage can be used to link polypeptides within a polypeptide composition. For example, adding $\epsilon$-aminohexanoic acid (Ahx) to the three available amino groups of Lys-Lys-Tyr-Gly-resin allows three distinct polypeptides of a polypeptide composition to be synthesized in parallel. In this case, each polypeptide contains at least one interpolypeptide linkage with at least one of the other two polypeptides of the polypeptide composition, and each interpolypeptide linkage is located at or near the C-terminal ends of the three polypeptides.

In addition, interpolypeptide linkages can be added at or near the last stages of polypeptide synthesis to allow the polypeptides to be linked at or near their N-terminal ends. For example, each N-terminal $\alpha$-amino group of three distinct polypeptides can be linked by an amide bond to a tricarboxylic acid such as Kemp triacid (KTA, cis,cis-1,3, 5-trimethylcyclohexane-1,3,5-tricarboxylic acid; Goodman et al., *J. Am. Chem. Soc.*, 118:5156–5157 (1996) and Feng et al., *J. Am. Chem. Soc.*, 118:10351–10358 (1996)) or 1,2,3-propanetricarboxylic acid (Greiche and Heidemann, *Biopolymers*, 18:2359–2361 (1979)). Alternatively, a glutamic acid dipeptide, in which the two side-chain carboxylic acid groups as well as the $\alpha$-carboxylic acid group are individually coupled to one of three distinct polypeptides, can be used to form a polypeptide composition where each of the three polypeptides contains at least one interpolypeptide linkage with at least one of the other two polypeptides of the polypeptide composition, and where each interpolypeptide linkage is located at or near the N-terminal ends of the three polypeptides (Hojo et al., *Tetrahedron*, 53:14263–14274 (1997)). Other examples of interpolypeptide linkages include, without limitation, disulfide knots formed between cysteine residues (Ottl and Moroder, *Tetrahedron Lett.*, 40:1487–1490 (1999)) or other thiol-containing units located, for example, at or near the N- or C-terminus of the connected polypeptides. In such disulfide knots, a single cysteine residue or thiol-containing unit can be incorporated into two distinct polypeptides, while two cysteine residues or thiol-containing units are incorporated into a third polypeptide. Oxidation of the cysteine residues or thiol-containing units can then covalently link the three polypeptide strands to each other such that each of the three polypeptides contains at least one interpolypeptide linkage with at least one of the other two polypeptides of the polypeptide composition. Cysteine residues or thiol-containing units such as 3-mercaptopropionic acid can be located at or near the N-terminus of each of polypeptides to be linked. In addition, cysteine residues or thiol-containing units can be alkylated with an alkyl tribromide or triiodide. Examples of such alkyltrihalogenides include, without limitation, 1,2,3-tribromo- or triiodomethylpropane as well as compounds obtained by coupling each of the three carboxylic acid groups of Kemp triacid to one of the amino groups of a diamine such as 1,2-diaminoethane followed by attachment of $\alpha$-bromo or $\alpha$-iodo acetic acid to the other amino group of the diamine. In addition, lysine residues can be included at or near the N-terminus of each of the polypeptides to be connected such that the amino groups of these lysine residues can be linked by treatment with glutaraldehyde. Treatment with glutaraldehyde leads to the formation of imines with the amino groups of the lysine residues.

Any unit can be incorporated into the polypeptides of a polypeptide composition. The term "unit" as used herein with reference to the sequence of a polypeptide refers to any of the twenty conventional amino acid residues as well as any other chemical structure that can be incorporated into a sequence including, without limitation, ornithine (Orn), citrulline (Cit), $\epsilon$-aminohexanoic acid (Ahx). Hydroxylated amino acids such as 3-hydroxyproline (3Hyp), 4-hydroxyproline (4Hyp or simply Hyp), (5R)-5-hydroxy-L-lysine (Hyl), allo-hydroxylysine (aHyl), and 5-hydroxy-L-norvaline (Hnv) can be incorporated into a sequence. Glycosylated amino acids such as amino acids containing monosaccharides (e.g., D-glucose, D-galactose, D-mannose, D-glucosamine, and D-galactosamine) or combinations of monosaccharides also can be incorporated into a polypeptide sequence. Other examples of modified chemical structures that can be incorporated into a sequence include, without limitation, 2-aminoadipic acid (Aad), 3-aminoadipic acid (bAad), beta-alanine or beta-aminopropionic acid (bAla), 2-aminobutyric acid (Abu), 4-aminobutyric acid or piperidinic acid (4Abu), 6-aminocaproic acid (Acp), 2-aminoheptanoic acid (Ahe), 2-aminoisobutyric acid (Aib), 3-aminoisobutyric acid (bAib), 2-aminopimelic acid (Apm), 2, 4-diaminobutyric acid (Dbu), desmosine (Des), 2,2-diaminopimelic acid (Dpm), 2,3-diaminopropionic acid (Dpr), N-ethylglycine (EtGly), N-ethylasparagine (EtAsn), isodesmosin (Ide), allo-isoleucine (alle), N-methylglycine or sarcosine (MeGly), N-methylisoleucine (MeIle), 6-N-methyllysine (MeLys), N-methylvaline (MeVal), norvaline (Nva), and norleucine (Nle). Specific modifications can include, without limitation, ornithine modifications of arginine (OrnR) or citrulline modifications of arginine (CitR). Further examples of chemical structures that can be incorporated into a sequence include, without limitation, $\beta$-D-galactopyranosyl-5-hydroxy-L-lysine with single or multiple deoxygenations and 2-O-$\alpha$-D-glucopyranosly-$\beta$-D-galactopyranosyl-5-hydroxy-L-lysine with single or multiple deoxygenations. In addition, one or more hydroxyl groups of a unit can be replaced with fluorine. For example, the hydroxy group of 3-hydroxyproline (3Hyp) can be replaced with fluorine to create 3-fluoroproline (3Flp), or the hydroxy group of 4-hydroxyproline (4Hyp) can be replaced with fluorine to create 4-fluoroproline (4Flp). Further, units having C- or S-glycosidic linkages can replace the O-glycosidic linkages. It will be appreciated that a single polypeptide can contain any combination of units. For example, a single polypeptide can contain twelve conventional amino acids, eight hydroxylated amino acids, two glycosylated amino acids, and one ornithine in any order.

Units also can be placed together to form a triple helix formation sequence. The term "triple helix formation sequence" as used herein refers to any sequence of units of a polypeptide that can form a stable triple helical conformation through non-covalent interactions with any two other polypeptides under optimal conditions. Examples of triple helix formation sequences include, without limitation, (Gly-Xaa-Yaa)$_n$, where Xaa and Yaa can be any unit and n can be any integer greater than three (e.g., any integer greater than 4, 5, 6, 7, 8, 9, 10, 15, 20, 25, 50, 100, 200, 500, or 1000). Thus, a polypeptide containing (Gly-Pro-Arg)$_8$ can be a polypeptide having a triple helix formation sequence.

A polypeptide composition within the scope of the invention can contain polypeptides having a sequence of units connected by amide bonds (—CONH—) or any other bond including, without limitation, modified amide bonds such as those modified by N-methylation (—CONMe—), N-alkylation (—CONR—), or reduction (—CH$_2$NH—) as well as isosteres bonds such as methylene ether bonds (—CH$_2$O—), methylene thioether bonds (—CH$_2$S—), vinyl group bonds (—CH=CH—), ethylene group bonds (—CH$_2$CH$_2$—), ketomethylene group bonds (—COCH$_2$—), thioamide bonds (—CSNH—), and sulfone bonds (—CH$_2$SO—). It will be appreciated that a single polypeptide can contain a sequence of units connected by any combination of bonds. For example, a single polypeptide can contain a sequence of units connected exclusively by amide bonds or by a combination of amide bonds, methylene ether bonds, and sulfone bonds.

A polypeptide composition can contain any sequence. Typically, a polypeptide composition contains an amino acid sequence corresponding to at least a portion of the amino acid sequence (e.g., at least about 5, 6, 7, 8, 9, 10, 11, 12, 13, 14, 15, 16, 17, 18, 19, 20, 21, 22, 23, 24, 25, 30, 35, 40, 50, or more amino acid residues) of CII (e.g., human, rat, or mouse CII). The amino acid sequence of human CII is set forth in SEQ ID NO:1 as well as FIG. 1. The nucleic acid sequence that encodes human CII is set forth in SEQ ID NO:2 as well as FIG. 2.

A polypeptide composition can contain a polypeptide having an epitope. The term "epitope" as used herein refers to a sequence of units (e.g., an amino acid sequence) that is recognized by a lymphocyte (e.g., a B cell or a T cell). The term "B cell epitope" as used herein refers to a sequence of units that is recognized by a B cell. For example, an amino acid sequence corresponding to a sequence from CII recognized by a B cell can be a B cell epitope. Examples of CII B cell epitopes include, without limitation, CII$_{(256-270)}$(Gly-Glu-Pro-Gly-Ile-Ala-Gly-Phe-Lys-Gly-Glu-Gln-Gly-Pro-Lys; SEQ ID NO:3), CII$_{(358-366)}$ (Gly-Ala-Arg-Gly-Leu-Thr-Gly-Arg-Pro; SEQ ID NO:4), CII$_{(358-369)}$ (Gly-Ala-Arg-Gly-Leu-Thr-Gly-Arg-Pro-Gly-Asp-Ala; SEQ ID NO:5), CII$_{(259-274)}$ (Gly-Ile-Ala-Gly-Phe-Lys-Gly-Glu-Gln-Gly-Pro-Lys-Gly-Glu-Pro-Gly; SEQ ID NO:6), CII$_{(494-504)}$ (Leu-Val-Gly-Pro-Arg-Gly-Glu-Arg-Gly-Phe-Pro; SEQ ID NO:7), CII$_{(551-564)}$ (Met-Pro-Gly-Glu-Arg-Gly-Ala-Ala-Gly-Ile-Ala-Gly-Pro-Lys; SEQ ID NO:8), CII$_{(932-936)}$ (His-Arg-Gly-Phe-Thr; SEQ ID NO:9), CII$_{(687-698)}$ (Arg-Gly-Ala-Gln-Gly-Pro-Pro-Gly-Ala-Thr-Gly-Phe; SEQ ID NO:10), CII$_{(777-783)}$ (Ala-Gly-Gln-Arg-Gly-Ile-Val; SEQ ID NO:11), CII$_{(124-142)}$ (Gly-Pro-Arg-Gly-Leu-Pro-Gly-Glu-Arg-Gly-Arg-Thr-Gly-Pro-Ala-Gly-Ala-Ala-Gly; SEQ ID NO:12), CII$_{(208-220)}$ (Gly-Asn-Pro-Gly-Thr-Asp-Gly-Ile-Pro-Gly-Ala-Lys-Gly; SEQ ID NO:13), CII$_{(182-193)}$ (Ala-Arg-Gly-Pro-Glu-Gly-Ala-Gln-Gly-Pro-Arg; SEQ ID NO:14), and CII$_{(368-381)}$ (Asp-Ala-Gly-Pro-Gln-Gly-Lys-Val-Gly-Pro-Ser-Gly-Ala-Pro; SEQ ID NO:15).

The term "T cell epitope" as used herein refers to a sequence of units that is recognized by a T cell. For example, an amino acid sequence corresponding to a sequence from CII recognized by a T cell can be a T cell epitope. Examples of CII T cell epitopes include, without limitation, CII$_{(259-274)}$ (Gly-Ile-Ala-Gly-Phe-Lys-Gly-Glu-Gln-Gly-Pro-Lys-Gly-Glu-Pro-Gly; SEQ ID NO:6), CII$_{(335-349)}$ (Pro-Ser-Gly-Leu-Ala-Gly-Pro-Lys-Gly-Ala-Asn-Gly-Asp-Pro-Gly; SEQ ID NO:16), CII$_{(374-388)}$ (Lys-Val-Gly-Pro-Ser-Gly-Ala-Pro-Gly-Glu-Asp-Gly-Arg-Pro-Gly; SEQ ID NO:17), CII$_{(404-418)}$ (Phe-Pro-Gly-Pro-Lys-Gly-Ala-Asn-Gly-Glu-Pro-Gly-Lys-Ala-Gly; SEQ ID NO:18), CII$_{(593-607)}$ (Pro-Pro-Gly-Pro-Ala-Gly-Ala-Asn-Gly-Glu-Lys-Gly-Glu-Val-Gly; SEQ ID NO:19), CII$_{(707-721)}$ (Pro-Pro-Gly-Ala-Asn-Gly-Asn-Pro-Gly-Pro-Ala-Gly-Pro-Pro-Gly; SEQ ID NO:20), CII$_{(224-238)}$ (Ala-Pro-Gly-Ile-Ala-Gly-Ala-Pro-Gly-Phe-Pro-Gly-Pro-Arg-Gly; SEQ ID NO:21), CII$_{(88-95)}$ (Gly-His-Arg-Gly-Tyr-Pro-Gly-Leu; SEQ ID NO:22), CII$_{(791-798)}$ (Gly-Glu-Arg-Gly-Phe-Pro-Gly-Leu; SEQ ID NO:23), and CII$_{(931-938)}$ (Gly-His-Arg-Gly-Phe-Thr-Gly-Leu; SEQ ID NO:24).

An epitope can be used in a native form. For example, an epitope can have an amino acid sequence identical to a sequence from CII (e.g., amino acid residues 259–274). In addition, an epitope can be a mutated version of a native sequence. For example, the fifth unit of an epitope can be replaced with a different unit. Mutated epitopes can contain any number of additions, deletions, substitutions, or combinations thereof. For example, in one embodiment a mutated epitope can be a CII T cell epitope with amino acid residues 260–270, where the glutamine residue at position 267 is substituted with a glutamic acid residue (e.g., CII$_{(260-267E-270)}$. An epitope also can be used in a modified form. For example, in one embodiment a modified epitope can be a CII B cell epitope with amino acid residues 259–274, where the proline at residue 273 is hydroxylated (e.g., CII$_{(259-273Hyp-274)}$). Any type of modification can be used. For example, a modification can include, without limitation, hydroxylation or glycosylation. Examples of modified epitopes include, without limitation, CII$_{(358-366Hyp)}$ (Gly-Ala-Arg-Gly-Leu-Thr-Gly-Arg-Hyp; SEQ ID NO:25), CII$_{(358-366Hyp-369)}$ (Gly-Ala-Arg-Gly-Leu-Thr-Gly-Arg-Hyp-Gly-Asp-Ala; SEQ ID NO:26), CII$_{(259-273Hyp-274)}$ (Gly-Ile-Ala-Gly-Phe-Lys-Gly-Glu-Gln-Gly-Pro-Lys-Gly-Glu-Hyp-Gly; SEQ ID NO:27), CII$_{(494-504Hyp)}$ (Leu-Val-Gly-Pro-Arg-Gly-Glu-Arg-Gly-Phe-Hyp; SEQ ID NO:28), CII$_{(551-552Hyp-564)}$ (Met-Hyp-Gly-Glu-Arg-Gly-Ala-Ala-Gly-Ile-Ala-Gly-Pro-Lys; SEQ ID NO:29), CII$_{(358-360CtR-365CtR-366Hyp-369)}$ (Gly-Ala-CtR-Gly-Leu-Thr-Gly-CtR-Hyp-Gly-Asp-Ala; SEQ ID NO:30), CII$_{(358-360OnR-365OnR-366Hyp-369)}$ (Gly-Ala-OnR-Gly-Leu-Thr-Gly-OnR-Hyp-Gly-Asp-Ala; SEQ ID NO:31), CII$_{(124-129Hyp-142)}$ (Gly-Pro-Arg-Gly-Leu-Hyp-Gly-Glu-Arg-Gly-Arg-Thr-Gly-Pro-Ala-Gly-Ala-Ala-Gly; SEQ ID NO:32), CII$_{(208-210Hyp-216Hyp-220)}$ (Gly-Asn-Hyp-Gly-Thr-Asp-Gly-Ile-Hyp-Gly-Ala-Lys-Gly; SEQ ID NO:33), and CII$_{(368-381Hyp)}$ (Asp-Ala-Gly-Pro-Gln-Gly-Lys-Val-Gly-Pro-Ser-Gly-Ala-Hyp; SEQ ID NO:34). Additionally, any combination of modifications can be used. For example, an epitope can have two hydroxylated units and one glycosylated unit. An epitope also can contain a unit that has more than one modification. For example, the lysine at residue 264 of the CII epitope CII$_{(256-270)}$ can be both hydroxylated and glycosylated (e.g., CII$_{(256-264Ghyl-270)}$).

A polypeptide can contain one epitope or more than one (e.g., 2, 3, 4, 5, or more) epitope. For example, a polypeptide can contain four contiguous B cell epitopes. Alternatively, a polypeptide can contain four B cell epitopes each separated by any number, type, and combination of units or linkages. A polypeptide also can contain different combinations of B cell and T cell epitopes. For example, both a B cell epitope and a T cell epitope can be incorporated into a polypeptide.

Each distinct polypeptide of a polypeptide composition can contain any sequence. For example, a single polypeptide can contain Gly-Pro-Thr-Ser-Ser-Leu (SEQ ID NO:35), the CII B cell epitope $CII_{(259-274)}$ (SEQ ID NO:6), and Met-Glu-Met-Gly-Gly-Leu-Arg-Hyp (SEQ ID NO:36). Such a polypeptide can be represented as Gly-Pro-Thr-Ser-Ser-Leu-$CII_{(259-274)\text{-}Met\text{-}Glu\text{-}Met\text{-}Gly\text{-}Gly\text{-}Leu\text{-}Arg\text{-}Hyp}$ (SEQ ID NO:37). In some cases, a polypeptide of a polypeptide composition can contain repeating units. For example, a polypeptide can contain two methionines followed by Gly-Pro-Arg-Gly-Pro-Arg-Gly-Pro-Arg (SEQ ID NO:38) followed by Glu-Ser-Phe-Leu-Glu-Ser-Phe-Leu-Glu-Ser-Phe-Leu-Glu-Ser-Phe-Leu-Glu-Ser-Phe-Leu (SEQ ID NO:39). Such a polypeptide can be represented as Met-Met-Gly-Pro-Arg-Gly-Pro-Arg-Gly-Pro-Arg-Glu-Ser-Phe-Leu-Glu-Ser-Phe-Leu-Glu-Ser-Phe-Leu-Glu-Ser-Phe-Leu-Glu-Ser-Phe-Leu (SEQ ID NO:40) or $(Met)_2(Gly\text{-}Pro\text{-}Pro)_3(Glu\text{-}Ser\text{-}Phe\text{-}Leu)_5$ (SEQ ID NO:40). A polypeptide of a polypeptide composition can contain any number of interpolypeptide linkages. Any polypeptide of a polypeptide composition can be linked to any other polypeptide of the polypeptide composition.

In one embodiment, the three polypeptides of a polypeptide composition can each contain a sequence that extends in the N-terminal direction from an Axh unit that is attached to one of the three available amino groups on the two Lys residues of a Lys-Lys-Tyr-Gly-resin. In this case, the portion containing the three Ahx residues attached to the Lys-Lys-Tyr-Gly sequence can be represented as $L_{Ahx}$. Thus, a polypeptide composition containing three $(Gly\text{-}Pro\text{-}Hyp)_6$-$CII_{(259-274)}$-$(Gly\text{-}Pro\text{-}Hyp)_2$ polypeptides each extending from one of the Ahx units of $L_{Ahx}$ can be represented as $[(Gly\text{-}Pro\text{-}Hyp)_6\text{-}CII_{(259-274)}\text{-}(Gly\text{-}Pro\text{-}Hyp)_2]_3 L_{Ahx}$.

In another embodiment, the three polypeptides of a polypeptide composition can each contain a sequence that extends in the N-terminal direction from an Axh unit that is attached to one of the three available amino groups on the two Lys residues of a Lys-Lys-Phe(F)-Tyr-Gly-resin. In this case, the portion containing the three Ahx residues attached to the Lys-Lys-Phe(F)-Tyr-Gly sequence can be represented as $L(F)_{Ahx}$. Thus, a polypeptide composition containing three $(Gly\text{-}Pro\text{-}Hyp)_6$-$CII_{(259-274)}$-$(Gly\text{-}Pro\text{-}Hyp)_2$ polypeptides each extending from one of the Ahx units of $L(F)_{Ahx}$ can be represented as $[(Gly\text{-}Pro\text{-}Hyp)_6\text{-}CII_{(259-274)}\text{-}(Gly\text{-}Pro\text{-}Hyp)_2]_3 L(F)_{Ahx}$.

In some embodiments, each polypeptide of a polypeptide composition can contain a sequence that extends in the C-terminal direction from a Gly unit that is attached to KTA. Thus, a polypeptide composition containing three $(Gly\text{-}Pro\text{-}Hyp)_6$-$CII_{(259-274)}$-$(Gly\text{-}Pro\text{-}Hyp)_2$ polypeptides each extending from one of the Ahx units of $L_{Ahx}$ to a Gly unit attached to KTA can be represented as KTA-$[Gly\text{-}(Gly\text{-}Pro\text{-}Hyp)_6\text{-}CII_{(259-274)\text{-}(Gly\text{-}Pro\text{-}Hyp)2}]_3 L_{Ahx}$. Such complexes have interpolypeptide linkages in both the N-terminal and C-terminal regions. An example of such a polypeptide complex is provided in FIG. 21.

It is noted that a polypeptide composition containing three distinct polypeptides can contain no interpolypeptide linkages. Such a polypeptide composition can be a triple helix polypeptide composition where three distinct polypeptides are associated by non-covalent bonds.

Nucleic Acids

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally occurring genome. For example, non-naturally-occurring nucleic acid such as an engineered nucleic acid is considered to be isolated nucleic acid. Engineered nucleic 10 acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

The term "exogenous" as used herein with reference to nucleic acid and a particular cell refers to any nucleic acid that does not originate from that particular cell as found in nature. Thus, all non-naturally-occurring nucleic acid is considered to be exogenous to a cell once introduced into the cell. It is important to note that non-naturally-occurring nucleic acid can contain nucleic acid sequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a cell once introduced into the cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid.

Nucleic acid that is naturally occurring can be exogenous to a particular cell. For example, an entire chromosome isolated from a cell of person X is an exogenous nucleic acid with respect to a cell of person Y once that chromosome is introduced into Y's cell.

The invention provides isolated nucleic acids that encode a polypeptide having an amino acid sequence at least about 70% identical to the sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56, or a polypeptide described herein. The percent identity between two nucleic acid sequences or two amino acid sequences is determined as follows. First, a nucleic acid sequence is compared to, for example, a portion of SEQ ID NO:2 or an amino acid sequence is compared to, for example, SEQ ID NO:6 using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site at fr.com or from the U.S. government's National Center for Biotechnology Information web site at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q−1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences. Once aligned, the number of matches is determined by counting the number of positions where an identical nucleotide or amino acid residue is presented in both sequences.

The percent identity is determined by dividing the number of matches by the length of the sequence set forth in an identified sequence (e.g., the portion of SEQ ID NO:2 or the entire SEQ ID NO:6) followed by multiplying the resulting value by 100. For example, if a sequence is compared to the sequence set forth in SEQ ID NO:6 (the length of the sequence set forth in SEQ ID NO:6 is 16) and the number of matches is 12, then the sequence has a percent identity of 75 (i.e., 12÷16*100=75) to the sequence set forth in SEQ ID NO:6. It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

The invention also provides isolated nucleic acid molecules that are at least about 5 bases in length (e.g., at least about 5, 6, 7, 8, 9, 10, 15, 20, 25, 30, 40, 50, 60, 100, 250, 500, 750, 1000, 1500, 2000, 3000, 4000, or 5000 bases in length) and hybridize, under hybridization conditions, to the sense or antisense strand of a nucleic acid that encodes an amino acid sequence as set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56. The hybridization conditions can be moderately or highly stringent hybridization conditions.

For the purpose of this invention, moderately stringent hybridization conditions mean the hybridization is performed at about 42° C. in a hybridization solution containing 25 mM $KPO_4$ (pH 7.4), 5×SSC, 5×Denhart's solution, 50 µg/mL denatured, sonicated salmon sperm DNA, 50% formamide, 10% Dextran sulfate, and 1–15 ng/mL probe (about $5×10^7$ cpm/µg), while the washes are performed at about 50° C. with a wash solution containing 2×SSC and 0.1% sodium dodecyl sulfate.

Highly stringent hybridization conditions mean the hybridization is performed at about 42° C. in a hybridization solution containing 25 mM KPO4 (pH 7.4), 5×SSC, 5×Denhart's solution, 50 µg/mL denatured, sonicated salmon sperm DNA, 50% formamide, 10% Dextran sulfate, and 1–15 ng/mL probe (about $5×10^7$ cpM/µg), while the washes are performed at about 65° C. with a wash solution containing 0.2×SSC and 0.1% sodium dodecyl sulfate.

Isolated nucleic acid molecules within the scope of the invention can be obtained using any method including, without limitation, common molecular cloning and chemical nucleic acid synthesis techniques. For example, PCR can be used to obtain an isolated nucleic acid molecule containing a nucleic acid sequence sharing similarity to a nucleic acid sequence that encodes an amino acid sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

Isolated nucleic acid molecules within the scope of the invention also can be obtained by mutagenesis. For example, an isolated nucleic acid containing a portion of the sequence set forth in SEQ ID NO:2 can be mutated using common molecular cloning techniques (e.g., site-directed mutagenesis). Possible mutations include, without limitation, deletions, insertions, and substitutions, as well as combinations of deletions, insertions, and substitutions.

In addition, nucleic acid and amino acid databases (e.g., GenBank®) can be used to obtain an isolated nucleic acid molecule within the scope of the invention. For example, any nucleic acid sequence having some homology to a nucleic acid sequence that encodes an amino acid sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56 can be used as a query to search GenBank®.

Further, nucleic acid hybridization techniques can be used to obtain an isolated nucleic acid molecule within the scope of the invention. Briefly, any nucleic acid molecule having some homology to a nucleic acid sequence that encodes a sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56 can be used as a probe to identify a similar nucleic acid by hybridization under conditions of moderate to high stringency. Once identified, the nucleic acid molecule then can be purified, sequenced, and analyzed to determine whether it is within the scope of the invention as described herein.

Hybridization can be done by Southern or Northern analysis to identify a DNA or RNA sequence, respectively, which hybridizes to a probe. The probe can be labeled with a biotin, digoxygenin, an enzyme, or a radioisotope such as $^{32}P$. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39–7.52 of Sambrook et al., (1989) Molecular Cloning, second edition, Cold Spring harbor Laboratory, Plainview, N.Y. Typically, a probe is at least about 20 nucleotides in length. For example, a probe corresponding to a 20-nucleotide sequence set forth in SEQ ID NO:2 can be used to identify an identical or similar nucleic acid. In addition, probes longer or shorter than 20 nucleotides can be used.

Substantially Pure Polypeptides

The invention provides substantially pure polypeptides. The term "substantially pure" as used herein with reference to a polypeptide means the polypeptide is substantially free of other polypeptides, lipids, carbohydrates, and nucleic acid with which it is naturally associated. Thus, a substantially pure polypeptide is any polypeptide that is removed from its natural environment and is at least 60 percent pure. The term "substantially pure" as used herein with reference to a polypeptide also includes chemically synthesized polypeptides and polypeptide compositions. A substantially pure polypeptide can be at least about 65, 70, 75, 80, 85, 90, 95, or 99 percent pure. Typically, a substantially pure polypeptide will yield a single major band on a non-reducing polyacrylamide gel.

Any substantially pure polypeptide having an amino acid sequence encoded by a nucleic acid within the scope of the invention is itself within the scope of the invention. In addition, any substantially pure polypeptide containing an amino acid sequence having a 70% identity to the sequence set forth in SEQ ID NO:3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 54, 55, or 56 as determined herein is within the scope of the invention.

Any method can be used to obtain a substantially pure polypeptide. For example, common polypeptide purification techniques such as affinity chromatography and HPLC as well as polypeptide synthesis techniques can be used. In addition, any material can be used as a source to obtain a substantially pure polypeptide. For example, tissue from wild type or transgenic animals can be used as a source material. In addition, tissue culture cells engineered to over-express a particular polypeptide of interest can be used to obtain substantially pure polypeptide. Further, a polypeptide within the scope of the invention can be "engineered" to contain an amino acid sequence that allows the polypeptide to be captured onto an affinity matrix. For example, a tag such as c-myc, hemagglutinin, polyhistidine, or Flag™ tag (Kodak) can be used to aid polypeptide purification. Such tags can be inserted anywhere within the polypeptide including at either the carboxyl or amino termini. Other fusions that could be useful include enzymes that aid in the detection of the polypeptide, such as alkaline phosphatase.

Host Cells

A host cell within the scope of the invention is any cell containing at least one isolated nucleic acid molecule described herein. Such cells can be prokaryotic cells or eukaryotic cells. It is noted that cells containing an isolated nucleic acid molecule within the scope of the invention are not required to express a polypeptide. In addition, the isolated nucleic acid molecule can be integrated into the genome of the cell or maintained in an episomal state. Thus, host cells can be stably or transiently transfected with a construct containing an isolated nucleic acid molecule of the invention.

Host cells within the scope of the invention can contain an exogenous nucleic acid molecule that encodes a polypeptide containing an epitope. The epitope can be related to an autoimmune condition. For example, cells can contain a nucleic acid molecule encoding the $CII_{(256-270)}$ epitope. Other examples include cells containing a nucleic acid molecule encoding other epitopes described herein such as the $CII_{(259-274)}$ epitope. Such epitopes can contain any sequence. For example, the $CII_{(259-274)}$ epitope can contain a glutamic acid residue at position 266 and/or a threonine or proline residue at position 273. In addition, the host cells can express the encoded polypeptide.

Any methods can be used to introduce an isolated nucleic acid molecule into a cell in vivo or in vitro. For example, calcium phosphate precipitation, electroporation, heat shock, lipofection, microinjection, and viral-mediated nucleic acid transfer are common methods that can be used to introduce an isolated nucleic acid molecule into a cell. In addition, naked DNA can be delivered directly to cells in vivo as describe elsewhere (U.S. Pat. Nos. 5,580,859 and 5,589,466 including continuations thereof). Further, isolated nucleic acid molecules can be introduced into cells by generating transgenic animals.

Transgenic animals can be aquatic animals (such as fish, sharks, dolphin, and the like), farm animals (such as pigs, goats, sheep, cows, horses, rabbits, and the like), rodents (such as rats, guinea pigs, and mice), non-human primates (such as baboon, monkeys, and chimpanzees), and domestic animals (such as dogs and cats). Several techniques known in the art can be used to introduce isolated nucleic acid molecules into animals to produce the founder lines of transgenic animals. Such techniques include, without limitation, pronuclear microinjection (U.S. Pat. No. 4,873,191); retrovirus mediated gene transfer into germ lines (Van der Putten et al., *Proc. Natl. Acad. Sci., USA,* 82:6148 (1985)); gene transfection into embryonic stem cells (Gossler A et al., *Proc Natl Acad Sci USA* 83:9065–9069 (1986)); gene targeting into embryonic stem cells (Thompson et al., *Cell,* 56:313 (1989)); nuclear transfer of somatic nuclei (Schnieke A E et al., *Science* 278:2130–2133 (1997)); and electroporation of embryos (Lo C W, *Mol. Cell. Biol.,* 3:1803–1814 (1983)). Once obtained, transgenic animals can be replicated using traditional breeding or animal cloning.

Any method can be used to identify cells containing an isolated nucleic acid molecule of the invention. Such methods include, without limitation, PCR and nucleic acid hybridization techniques such as Northern and Southern analysis. In some cases, immunohistochemistry and biochemical techniques can be used to determine if a cell contains a particular isolated nucleic acid molecule by detecting the expression of a polypeptide encoded by that particular nucleic acid molecule.

Identifying, Treating, and Enhancing Tolerance in Mammals with Autoimmune Conditions The invention provides methods and materials related to identifying a mammal with an autoimmune condition. For example, a polypeptide composition provided herein can be used to determine whether or not a sample from a mammal contains antibodies specific for an epitope or combination of epitopes within the polypeptide composition. Any method can be used to detect antibodies including, without limitation, affinity column or ELISA techniques. For example, a polypeptide composition containing a particular CII epitope can be immobilized on a column matrix, and an antibody-containing fluid (e.g., patient serum) can be screened for the presence or absence of antibodies that have affinity for that particular CII epitope. Alternatively, each well on a microtiter plate can be coated with a polypeptide composition containing a different CII epitope, and an antibody-containing fluid (e.g., patient serum) can be screened by ELISA techniques for the presence or absence of antibodies that recognize a specific CII epitope or combination of CII epitopes. In addition, a polypeptide composition provided herein can be used in a radioimmunoassay to determine whether or not a sample from a mammal contains antibodies specific for an epitope or combination of epitopes within the polypeptide composition.

The polypeptide compositions provided herein also can be used to determine whether or not a sample from a mammal contains B cells that recognize an epitope. B cell activity in response to epitope recognition (e.g., proliferation or antibody production) can be measured using a polypeptide composition provided herein. For example, the rate of $^3$H-labeled thymidine incorporation into proliferating B cell DNA in a population of B cells from a patient can be measured in response to treatment with a polypeptide composition containing a CII epitope. In another example, each well on a microtiter plate can be coated with a polypeptide composition containing a different CII epitope, and a patient sample containing B cells can be screened for the presence or absence of B cell-secreted antibodies that recognize a CII epitope of a combination of CII epitopes.

The polypeptide compositions provided herein also can be used to determine whether or not a sample from a mammal contains T cells that recognize an epitope. T cell activity in response to epitope recognition (e.g., proliferation or cytokine secretion) can be measured using a polypeptide composition provided herein. For example, the rate of $^3$H-labeled thymidine incorporation into proliferating T cell DNA in a population of T cells from a patient can be measured in response to treatment with a polypeptide composition containing a CII epitope. In another example, each well on a microtiter plate can be coated with a polypeptide composition containing a different CII epitope, and a mixture containing T cells from a mammal and purified dendritic cells can be screened by ELISA techniques for secreted IL-2. Other types of assays that can be used to assess T cell activity include ELISPOT assays and staining with peptide-tetramer complexes.

Any type of sample can be used to identify an autoimmune condition including, without limitation, serum, synovial fluid, blood, saliva, urine, and sputum. In addition, any method can be used to obtain a sample. For example, a syringe can be used to obtain peripheral blood from a mammal. Once obtained, a sample can be manipulated prior to determining whether or not it contains B cells or T cells that recognize epitopes. For example, serum can be separated from the other blood components in a peripheral blood sample by centrifugation.

The invention also provides methods for determining the severity of an autoimmune condition in a mammal. For example, a polypeptide composition provided herein can be used to determine the number of antibodies specific for an epitope or combination of epitopes in the polypeptide composition within a sample from a mammal. Any method can be used to detect the number of antibodies, including, without limitation, affinity column or ELISA techniques. For example, a polypeptide composition containing a particular CII epitope can be immobilized on a column matrix, and the concentration of antibodies that have affinity for that particular CII epitope in a sample (e.g., patient serum) can be compared to a standard containing a known concentration of antibodies that have affinity for the same particular CII epitope. Alternatively, each well on a microtiter plate can be coated with a polypeptide composition containing a different CII epitope, and the concentration of antibodies that have affinity for a particular CII epitope or combination of CII epitopes in a sample (e.g., patient serum) can be compared to standards containing known concentrations of antibodies that have affinity for each particular CII epitope. The polypeptide compositions provided herein also can be used to determine the level of B cell activity in response to epitope recognition (e.g., proliferation or antibody production) in a sample from a mammal containing B cells. For example, the rate of $^3$H-labeled thymidine incorporation into proliferating B cell DNA in a population of B cells from a patient can be measured in response to treatment with a polypeptide composition containing a CII epitope, and the resulting rate can be compared to the rates measured from B cell samples from patients with autoimmune conditions ranging from mild to severe. In another example, each well on a microtiter plate can be coated with a polypeptide composition containing a different CII epitope, and the concentration of antibodies that have affinity for a particular CII epitope or combination of CII epitopes in a sample (e.g., patient serum) can be compared to samples from patients with autoimmune conditions ranging from mild to severe containing known concentrations of antibodies that have affinity for each particular CII epitope. The polypeptide compositions provided herein also can be used to determine the level of T cell activity in response to epitope recognition (e.g., proliferation or cytokine secretion) in a sample from a mammal containing T cells. For example, the rate of $^3$H-labeled thymidine incorporation into proliferating T cell DNA in a population of T cells from a patient can be measured in response to treatment with a polypeptide composition containing a CII epitope, and the resulting rate can be compared to the rates measured from T cell samples from patients with autoimmune conditions ranging from mild to severe. In another example, each well on a microtiter plate can be coated with a polypeptide composition containing a different CII epitope, and the concentration of secreted IL-2 in a mixture of T cells from a mammal and purified dendritic cells can be measured and compared to samples from patients with autoimmune conditions ranging from mild to severe containing known concentrations of secreted IL-2.

Any type of sample can be used to determine the severity of an autoimmune condition including, without limitation, serum, synovial fluid, blood, saliva, urine, and sputum. In addition, any method can be used to obtain a sample. For example, a syringe can be used to obtain peripheral blood from a mammal. Once obtained, a sample can be manipulated prior to determining the level of B cell or T cell activity in response to epitope recognition. For example, serum can be separated from the other blood components in a peripheral blood sample by centrifugation.

The invention also provides methods and materials related to treating an autoimmune condition. Any method can be used to treat an autoimmune condition. For example, a polypeptide composition provided herein can be administered to a mammal having a rheumatoid arthritis condition. In such a case, the administered polypeptide composition can have several therapeutic effects. In one embodiment, an administered polypeptide composition containing a CII epitope can serve to compete for anti-CII antibody binding with the corresponding endogenous CII epitope. In another example, an administered polypeptide composition containing a CII epitope can serve to enhance tolerance for that particular CII antigen. The term "enhanced" as used herein with respect to tolerance in a mammal refers to any increase in that mammal's tolerance for a particular antigen. Enhancing tolerance, therefore, decreases a mammal's immune response to a particular antigen. If a particular antigen is a self-antigen related to an autoimmune condition, the severity of the symptoms of that condition can be reduced by enhancing tolerance to that specific self-antigen. Although not limited to any particular mode of action, tolerance can be enhanced by deleting reactive B cells, deleting reactive T cells, deleting both reactive B and T cells, or anergizing T cells.

Any method can be used to enhance tolerance in a mammal. For example, a polypeptide composition containing one or more self-antigen epitopes can be administered to a mammal in a dosage or series of dosages sufficient to enhance that mammal's tolerance for that antigen. Such dosages can be determined using methods that assess immune function or immune responsiveness. Any method can be used to administer an antigen including, without limitation, oral delivery, nasal delivery, intradermal injection, intravenous injection, or topical application. Further, the antigen can be administered in conjunction with a carrier. Such carriers include without limitation, proteins, alum, oils such as mineral oil, pristane, and bacterial or viral products. For example, a mixture of mineral oil and a polypeptide composition containing $CII_{(259-274)}$ can be intradermally injected into a mammal.

In some embodiments, a polypeptide composition containing a CII epitope is administered to a mammal to enhance tolerance. Some individuals' immune systems may recognize and react to wild type CII epitopes, while other individuals' immune systems may recognize wild type CII and CII epitopes in which glutamine (Q) is substituted with a glutamic acid (E). This may be due to the action of transglutaminase (coagulation factor XIII), which is present in inflamed and lymphoid infiltrate containing tissues such as the inflamed joints and intestine. Transglutaminase can change Q to E in contexts where Q is positioned in proximity to glycine (G) and P (proline) (e.g., in GQXP motifs). The Q at position 267 in the CII polypeptide resides in such a context and could be changed by transglutaminase to E in some individuals. In fact, MHC class II-restricted T cell hybridomas recognize the $CII_{(260-270)}$ epitope and not the $CII_{(260-267E-270)}$ epitope, while other MHC class II-restricted T cell hybridomas recognize both the $CII_{(260-270)}$ epitope and the $CII_{(260-267E-270)}$ epitope (Example 14, FIGS. 27–30). Thus, if an individual's immune system recognizes a wild type CII epitope (e.g., $CII_{(260-270)}$), then a polypeptide complex containing the wild type epitope can be used to enhance tolerance. If an individual's immune system recognizes a wild type CII epitope and a CII epitope containing an E instead of a Q (e.g., $CII_{(260-267E-270)}$), then each epitope can be used to enhance tolerance either alone or in combination. For example, in some embodiments, tolerance can be enhanced using an epitope containing E in place of a Q as the sole active ingredient of a treatment agent.

Any method can be used to assess a mammal's tolerance. Such methods can be subjective or objective. An example of a subjective method includes assessing whether or not a mammal with a rheumatoid arthritis condition experiences pain, swelling, and loss of joint function to a lesser extent following treatments to enhance tolerance. Alternatively, such methods can be objective. For example, the concentration of secreted IL-2 from a mixture of T cells and purified dendritic cells from a mammal after treatment can be measured and compared to the concentration of secreted IL-2 from a mixture of T cells and purified dendritic cells from the same mammal before treatment. If the level of secreted IL-2 after treatment is reduced compared to the level of secreted IL-2 before treatment, then tolerance for that antigen has been enhanced in that mammal.

In general, the polypeptide compositions described herein can be used to detect specific autoantibody binding as well as T cell reactivity leading to the identification of patients with autoimmune responses directed against specific polypeptides such as cartilage specific collagen type II. In addition, the polypeptide compositions described herein can be used (1) to diagnose an erosive arthritic disease, for example, rheumatoid arthritis, and (2) to identify subgroups of patients who may differ from others with respect to disease severity, prognosis, (immuno)genetic background, and/or responsiveness to treatment. Further, the materials and methods described herein can be used (1) to identify potential responders to CII-specific tolerization protocols in the treatment of arthritis, and (2) to monitor such immunomodulatory procedures. For example, the ELISA examples for the detection of conformation dependent CII-specific IgG autoantibodies in patient sera using triple helical synthetic polypeptide compositions demonstrate the principle feasibility and the specificity of the assay procedures.

The invention will be further described in the following examples, which do not limit the scope of the invention described in the claims.

EXAMPLES

Example 1

Synthesis of polypeptide complexes having interpolypeptide linkages in the C-Terminal region A Fmoc-Gly-TentaGel-R-PHB resin (substitution level: ~0.2 mmol/g, Rapp Polymere, Tüibingen, Germany) was used for the synthesis. $N^\alpha$-Fmoc-amino acids (Bachem, Switzerland) with the following protective groups were used: triphenylmethyl (Trt) for glutamine; tert-butyl for glutamic acid, hydroxyproline, and tyrosine; and tert-butoxycarbonyl (Boc) or allyloxycarbonyl (Aloc) for lysine.

1. Synthesis of a (Fmoc-Ahx)$_3$-Lys$_2$-Tyr-Gly-TentaGel-R-PHB Resin.

$N^\alpha$-Fmoc deprotection of the Fmoc-Gly-TentaGel-R-PHB resin, and all other Fmoc-deprotections, were affected by treatment with 20% piperidine in DMF during 10 to 20 minutes. Then, Fmoc-Tyr(tBu)-OH was activated as a 1-benzotriazolyl ester and added to the resin. Activation was performed by reaction of Fmoc-Tyr(tBu)-OH (4 equivalents as compared to the substitution level of the resin), 1-hydroxybenzotriazole (HOBt, 6 equivalents as compared to the substitution level of the resin) and 1,3-diisopropylcarbodiimide (DIC, 5.9 equivalents as compared to the substitution level of the resin) in DMF for 30 minutes. After addition of the solution of the HOBt ester of Fmoc-Tyr(tBu)-OH to the resin, the acylation was monitored by addition of a solution of bromophenol blue (0.1% as compared to the substitution level of the resin) in DMF to the reactor containing the resin. After incorporation of Fmoc-Tyr(tBu)-OH and Fmoc deprotection with piperidine, two residues of Fmoc-Lys(Aloc)-OH were coupled sequentially to the peptide resin in the same manner as Fmoc-Tyr(tBu)-OH. The conditions for coupling and Fmoc deprotection described in this example should not be limiting, and any state of the art procedures can be applied. The allyloxycarbonyl groups were removed by treatment with (Ph$_3$P)$_4$Pd(0), acetic acid, and N-methyl morpholine in CHCl$_3$ followed by removal of the N-terminal Fmoc group with piperidine. Fmoc-6-aminohexanoic acid (Fmoc-Ahx-OH, 9 equivalents as compared to the substitution level of the resin) was then coupled to the peptide resin using the same procedure as for Fmoc-Tyr(tBu)-OH to give a (Fmoc-Ahx)$_3$-Lys$_2$-Tyr-Gly-TentaGel-R-PHB resin.

2. Synthesis of a Triple Helical Polypeptide Composition Containing the CII$_{(259-274)}$ Epitope Using the (Fmoc-Ahx)$_3$-Lys$_2$-Tyr-Gly-TentaGel-R-PHB Resin.

After removal of the N-terminal Fmoc groups from the (Fmoc-Ahx)$_3$-Lys$_2$-Tyr-Gly-TentaGel-R-PHB resin, the CII$_{(259-274)}$ epitope was assembled onto the Ahx$_3$-Lys$_2$-Tyr-Gly-TentaGel-R-PHB resin using an automatic peptide synthesizer. The synthesizer used essentially the same conditions for activation of Fmoc protected amino acids and removal of Fmoc protective groups as described in the above manual synthesis. A sample of the triple helical polypeptide composition was Fmoc-deprotected, cleaved from the resin with simultaneous removal of protective groups using TFA-thioanisole-water-ethanedithiol (87.5-5-5-2.5) for 3 to 3.5 hours followed by filtration. Acetic acid was added to the filtrate, which was then concentrated. The residue was co-concentrated several times with acetic acid until it formed a thin film. It was washed with diethyl ether (3 times), dissolved in a mixture of water and acetic acid, and freeze dried. After purification by reversed-phase HPLC on a Kromasil C-8 column (250×20 mm, 5 μm, 100 Å) using a gradient of 0 to 100% CH$_3$CN in H$_2$O (both containing 0.1% TFA) during 60 minutes (flow rate: 11 mL/minute and detection at 214 nm), the [CII$_{(259-274)}$-Ahx]$_3$-Lys$_2$-Tyr-Gly polypeptide composition was subjected to electrospray mass spectrometry were it displayed the expected molecular weight.

Other polypeptide complexes were synthesized using methods similar to those described above. Briefly, the three strands of each triple polypeptide complex were synthesized in parallel from the three amino groups of Lys-Lys-Tyr-Gly-resin. In each case, ε-aminohexanoic acid (Ahx) was the first amino acid added to the Lys-Lys-Tyr-Gly-resin.

After adding the final amino acid, the polypeptide complex was treated with trifluoroacetic acid as well as water, phenol, ethanedithiol, and thioanisole to deprotect and release the polypeptide complex from the resin. The polypeptide complex was precipitated and washed in diethylether. To confirm synthesis, each polypeptide complex was digested with trypsin at 37° C., and the digestion products analyzed using MALDI-MS. In each case, the major peaks in the MS spectra corresponded to expected fragments, and all expected fragments were detected.

Example 2

Synthesis of polypeptide complexes having interpolypeptide linkages in the N-terminal regions using Kemp triacid or 1,2,3-propanetricarboxylic acid Kemp triacid (KTA) or 1,2,3-propanetricarboxylic acid (PTA) is linked to glycine to give KTA-(Gly-OH)$_3$ or PTA-(Gly-OH)$_3$ conjugates as described elsewhere (Feng et al., J. Am. Chem. Soc., 118:10351–10358 (1996)). After removing the N-terminal Fmoc protective groups from a protected [polypeptide-Ahx]$_3$-Lys$_2$-Tyr-Gly-TentaGel-R-PHB resin produced as described in Example 1, the solution of KTA-(Gly-OH)$_3$ or PTA-(Gly-OH)$_3$ along with HOBt or HOAt (4.5 equivalents as compared to KTA-(Gly-OH)$_3$ or PTA-(Gly-OH)$_3$) as well as DIC (3 equivalents as compared to KTA-(Gly-OH)$_3$ or PTA-(Gly-OH)$_3$) in DMF or a mixture of DMF and CH$_2$Cl$_2$, which may contain a small amount of water (<5%), is added slowly during five to ten hours to the [polypeptide-Ahx]$_3$-Lys$_2$-Tyr-Gly-TentaGel-R-PHB resin at temperatures ranging from 0° C. to 40° C. In total, 1 equivalent of KTA-(Gly-OH)$_3$ or PTA-(Gly-OH)$_3$ as compared to the amount of polypeptide resin is added. The coupling of KTA or PTA to the polypeptide resin is monitored by the Kaiser ninhydrin test and may require several days to reach completion. When the reaction had reached completion, deprotection, cleavage, and purification is performed as described in Example 1.

Example 3

Synthesis of polypeptide complexes having interpolypeptide linkages in the N-terminal regions using disulfide bonds The N-terminal Fmoc protective groups are removed from the protected [polypeptide-Ahx]$_3$-Lys$_2$-Tyr-Gly-TentaGel-R-PHB resin produced as described in Example 1. Cysteine residues or other thiol-containing units are then added to each of the three polypeptide strands using the conditions described in Example 1. After deprotection and cleavage as described in Example 1, oxidation to form a disulfide bond is performed as described elsewhere (Kihlberg et al., J. Med. Chem., 38:161–169 (1995)). Briefly, the oxidation is performed by alternating additions of portions of the crude polypeptide in acetic acid, and 0.1 M I$_2$ in methanol, to 10% acetic acid in methanol (1–4 mL/mg cleaved resin). After the final addition of $I_2$, a light brown solution is obtained which is neutralized and decolorized by stirring with Dowex 2×8 anion exchange resin (converted into acetate form by washing with 1 M aqueous NaOH, water, acetic acid, water, and methanol) and then filtered and concentrated. The residue is then dissolved in water and freeze-dried. Purification is performed using reversed phase HPLC as described in Example 1.

Example 4

Synthesis of polypeptide complexes having interpolypeptide linkages in the N-terminal regions using alkylation The N-terminal Fmoc protective groups are removed from the protected [polypeptide-Ahx]$_3$-Lys$_2$-Tyr-Gly-TentaGel-R-PHB resin produced as described in Example 1. Cysteine residues or other thiol-containing units are then added to each of the three polypeptides using the conditions described in Example 1. After deprotection and cleavage as described in Example 1, alkylation of the mercapto groups with alkyltrihalogenides is performed as described elsewhere (Bengtsson et al., *Glycoconj. J.*, 15:223–231 (1998)). Alkylation is performed by slow addition of the alkyltrihalogenide to a solution of the polypeptide and cesium carbonate in a dilute solution of DMF under argon during five to ten hours. The mixture is sonicated during the addition and then stirred at room temperature until analytical reversed phase HPLC indicates that polypeptide was consumed. Then, 0.1% aqueous trifluoroacetic acid is added so that the cesium carbonate is neutralized, after which the mixture is freeze-dried. Purification is performed using reversed phase HPLC as described in Example 1.

Example 5

Additional methods for synthesis of polypeptide complexes having interpolypeptide linkages in the N-terminal regions N-terminal capping of a triple polypeptide composition is accomplished by (1) introducing lysine residues or other units with a suitable spacing of the amino groups from the alpha carbon, and (2) crosslinking the amino groups at the amino end of the three polypeptides with one or more crosslinking agents. With a lysine attached to the amino end of the polypeptides, there will be 6 amino groups available for reactions. If the peptides do not contain any other amino groups in the amino acid sequence, the reaction can be performed on polypeptide composition without side change protecting groups and completed product liberated from the synthetic resin. Triple helical polypeptide compositions liberated from the synthetic resin can be crosslinked at the amino terminus in a water environment. In this case, the triple helical structure can be obtained before capping at the amino end.

Examples of crosslinking agents are glutardialdehyde, bis imido esters, p-amino phenyl acetic acids, and Kemp triacid. Glutardialdehyde can used to form triple helical polypeptide complexes as well as aggregates containing multiple covalently linked triple helical polypeptide complexes. If desired, the aggregates or the non-aggregated triple helical polypeptide complexes can be purified. Bisimido esters can couple one amino group to another amino group and are commercially available having different spacer lengths between their imindo groups.

Example 6

Synthesis of polypeptide complexes containing a modified amino acid residue

Seven polypeptide complexes were synthesized to contain modified amino acid residues (Table 1). Briefly, each polypeptide was synthesized as described in Example 1 with the exception that a modified amino acid residue was incorporated into the synthesized polypeptide strand as opposed to an unmodified amino acid residue.

TABLE 1

Polypeptide complexes containing a modified amino acid residue.

| Polypeptide complex | Sequence of the polypeptide chains up to the $L_{Ahx}$ group | |
|---|---|---|
| [(Gly-Pro-Hyp)$_5$-CII$_{(358-366Hyp-369)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Ala-Arg-Gly-Leu-Thr-Gly-Arg-Hyp-Gly-Asp-Ala-Gly-Pro-Hyp-Gly-Pro-Hyp | (SEQ ID NO:41) |
| [(Gly-Pro-Hyp)$_5$-CII$_{(259-273Hyp-274)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Ile-Ala-Gly-Phe-Lys-Gly-Glu-Gln-Gly-Pro-Lys-Gly-Glu-Hyp-Gly-Gly-Pro-Hyp-Gly-Pro-Hyp | (SEQ ID NO:42) |
| [(Gly-Pro-Hyp)$_5$-CII$_{(259-273Hyp-274)}$-CII$_{(359-366Hyp)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Ile-Ala-Gly-Phe-Lys-Gly-Glu-Gln-Gly-Pro-Lys-Gly-Glu-Hyp-Gly-Ala-Arg-Gly-Leu-Thr-Gly-Arg-Hyp-Gly-Pro-Hyp-Gly-Pro-Hyp | (SEQ ID NO:43) |
| [(Gly-Pro-Hyp)$_5$-CII$_{(551-552Hyp-564)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-Met-Hyp-Gly-Glu-Arg-Gly-Ala-Ala-Gly-Ile-Ala-Gly-Pro-Lys-Gly-Pro-Hyp-Gly-Pro-Hyp | (SEQ ID NO:44) |
| [(Gly-Pro-Hyp)$_5$-CII$_{(358-360CitR-365CitR-366Hyp-369)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Ala-CitR-Gly-Leu-Thr-Gly-CitR-Hyp-Gly-Asp-Ala-Gly-Pro-Hyp-Gly-Pro-Hyp | (SEQ ID NO:45) |
| [(Gly-Pro-Hyp)$_5$-CII$_{(494-504Hyp)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-Leu-Val-Gly-Pro-Arg-Gly-Glu-Arg-Gly-Phe-Hyp-Gly-Pro-Hyp-Gly-Pro-Hyp | (SEQ ID NO:46) |

TABLE 1-continued

Polypeptide complexes containing a modified amino acid residue.

| Polypeptide complex | Sequence of the polypeptide chains up to the $L_{Ahx}$ group | |
|---|---|---|
| [(Gly-Pro-Hyp)$_5$-CII$_{(358-366Hyp)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Ala-Arg-Gly-Leu-Thr-Gly-Arg-Hyp-Gly-Pro-Hyp-Gly-Pro-Hyp | (SEQ ID NO:47) |

In addition, the polypeptide complexes listed in Table 2 are synthesized as described in Example 1 with the exception that a modified amino acid residue are incorporated into the synthesized polypeptide strand as opposed to an unmodified amino acid residue.

TABLE 2

Polypeptide complexes containing a modified amino acid residue.

| Polypeptide complex | Sequence of the polypeptide chains up to the $L_{Ahx}$ group | |
|---|---|---|
| [(Gly-Pro-Hyp)$_6$-CII$_{(358-366Hyp-369)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-Gly-Ala-Arg-Gly-Leu-Thr-Gly-Arg-Hyp-Gly-Asp-Ala-Gly-Pro-Hyp-Gly-Pro-Hyp | (SEQ ID NO:61) |
| [(Gly-Pro-Hyp)$_6$-CII$_{(259-273Hyp-274)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-Gly-Ile-Ala-Gly-Phe-Lys-Gly-Glu-Gln-Gly-Pro-Lys-Gly-Glu-Hyp-Gly-Gly-Pro-Hyp-Gly-Pro-Hyp | (SEQ ID NO:62) |
| [(Gly-Pro-Hyp)$_6$-CII$_{(259-273Hyp-274)}$-CII$_{(359-366Hyp)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-Gly-Ile-Ala-Gly-Phe-Lys-Gly-Glu-Gln-Gly-Pro-Lys-Gly-Glu-Hyp-Gly-Ala-Arg-Gly-Leu-Thr-Gly-Arg-Hyp-Gly-Pro-Hyp-Gly-Pro-Hyp | (SEQ ID NO:63) |
| [(Gly-Pro-Hyp)$_6$-CII$_{(551-552Hyp-564)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-Met-Hyp-Gly-Glu-Arg-Gly-Ala-Ala-Gly-Ile-Ala-Gly-Pro-Lys-Gly-Pro-Hyp-Gly-Pro-Hyp | (SEQ ID NO:64) |
| [(Gly-Pro-Hyp)$_6$-CII$_{(358-360CitR-365CitR-366Hyp-369)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-Gly-Ala-CitR-Gly-Leu-Thr-Gly-CitR-Hyp-Gly-Asp-Ala-Gly-Pro-Hyp-Gly-Pro-Hyp | (SEQ ID NO:65) |
| [(Gly-Pro-Hyp)$_6$-CII$_{(494-504Hyp)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-Leu-Val-Gly-Pro-Arg-Gly-Glu-Arg-Gly-Phe-Hyp-Gly-Pro-Hyp-Gly-Pro-Hyp | (SEQ ID NO:66) |
| [(Gly-Pro-Hyp)$_6$-CII$_{(358-366Hyp)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-Gly-Ala-Arg-Gly-Leu-Thr-Gly-Arg-Hyp-Gly-Pro-Hyp-Gly-Pro-Hyp | (SEQ ID NO:67) |
| [(Gly-Pro-Hyp)$_6$-CII$_{(932-936)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-His-Arg-Gly-Phe-Thr-Gly-Pro-Hyp-Gly-Pro-Hyp | (SEQ ID NO:49) |
| [(Gly-Pro-Hyp)$_6$-CII$_{(687-698)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-Arg-Gly-Ala-Gln-Gly-Pro-Pro-Gly-Ala-Thr-Gly-Phe-Gly-Pro-Hyp-Gly-Pro-Hyp | (SEQ ID NO:50) |
| [(Gly-Pro-Hyp)$_6$-CII$_{(777-783)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-Ala-Gly-Gln-Arg-Gly-Ile-Val-Gly-Pro-Hyp-Gly-Pro-Hyp | (SEQ ID NO:51) |
| [(Gly-Pro-Hyp)$_6$-CII$_{(124-129Hyp-142)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-Gly-Pro-Arg-Gly-Leu-Hyp-Gly-Glu-Arg-Gly-Arg-Thr-Gly-Pro-Ala-Gly-Ala-Ala-Gly-Gly-Pro-Hyp-Gly-Pro-Hyp | (SEQ ID NO:52) |
| [(Gly-Pro-Hyp)$_6$-CII$_{(208-210Hyp-216Hyp-220)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-Gly-Asn-Hyp-Gly-Thr-Asp-Gly-Ile-Hyp-Gly-Ala-Lys-Gly-Gly-Pro-Hyp-Gly-Pro-Hyp | (SEQ ID NO:53) |
| [(Gly-Pro-Hyp)$_6$-CII$_{(182-193)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-Ala-Arg-Gly-Pro-Glu-Gly-Ala-Gln-Gly-Pro-Arg-Gly-Pro-Hyp-Gly-Pro-Hyp | (SEQ ID NO:54) |
| [(Gly-Pro-Hyp)$_6$-CII$_{(368-381Hyp)}$- | Gly-Pro-Hyp-Gly-Pro-Hyp-Gly-Pro-Hyp-Gly-Pro-Hyp- | (SEQ ID NO:55) |

TABLE 2-continued

Polypeptide complexes containing a modified amino acid residue.

| Polypeptide complex | Sequence of the polypeptide chains up to the $L_{Ahx}$ group | |
|---|---|---|
| (Gly-Pro-Hyp)$_2$]$_3$L$_{Ahx}$ | Gly-Pro-Hyp-Gly-Pro-Hyp-Asp-Ala-Gly-Pro-Gln-Gly-Lys-Val-Gly-Pro-Ser-Gly-Ala-Hyp-Gly-Pro-Hyp-Gly-Pro-Hyp | |
| [(Gly-Pro-Hyp)$_6$-CII$_{(358-360OrnR-365OrnR-366Hyp-369)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Hyp-Gly-Ala-OrnR-Gly-Leu-Thr-Gly-OrnR-Hyp-Gly-Asp-Ala-Gly-Pro-Hyp-Gly-Pro-Hyp | (SEQ ID NO:56) |
| [(Gly-Pro-Hyp)$_5$-CII$_{(932-936)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-His-Arg-Gly-Phe-Thr-Gly-Pro-Hyp-Gly-Pro-Hyp | (SEQ ID NO:68) |
| [(Gly-Pro-Hyp)$_5$-CII$_{(687-698)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Arg-Gly-Ala-Gln-Gly-Pro-Pro-Gly-Ala-Thr-Gly-Phe-Gly-Pro-Hyp-Gly-Pro-Hyp | (SEQ ID NO:69) |
| [(Gly-Pro-Hyp)$_5$-CII$_{(777-783)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Ala-Gly-Gln-Arg-Gly-Ile-Val-Gly-Pro-Hyp-Gly-Pro-Hyp | (SEQ ID NO:70) |
| [(Gly-Pro-Hyp)$_5$-CII$_{(124-129Hyp-142)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Pro-Arg-Gly-Leu-Hyp-Gly-Glu-Arg-Gly-Arg-Thr-Gly-Pro-Ala-Gly-Ala-Ala-Gly-Gly-Pro-Hyp-Gly-Pro-Hyp | (SEQ ID NO:71) |
| [(Gly-Pro-Hyp)$_5$-CII$_{(208-210Hyp-216Hyp-220)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Asn-Hyp-Gly-Thr-Asp-Gly-Ile-Hyp-Gly-Ala-Lys-Gly-Gly-Pro-Hyp-Gly-Pro-Hyp | (SEQ ID NO:72) |
| [(Gly-Pro-Hyp)$_5$-CII$_{(182-193)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Ala-Arg-Gly-Pro-Glu-Gly-Ala-Gln-Gly-Pro-Arg-Gly-Pro-Hyp-Gly-Pro-Hyp | (SEQ ID NO:73) |
| [(Gly-Pro-Hyp)$_5$-CII$_{(368-381Hyp)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Asp-Ala-Gly-Pro-Gln-Gly-Lys-Val-Gly-Pro-Ser-Gly-Ala-Hyp-Gly-Pro-Hyp-Gly-Pro-Hyp | (SEQ ID NO:74) |
| [(Gly-Pro-Hyp)$_5$-CII$_{(358-360OrnR-365OrnR-366Hyp-369)}$-(Gly-Pro-Hyp)$_2$]$_3$L$_{Ahx}$ | Gly-Pro-Hyp-Gly-Pro-Hyp-Gly-Pro-Hyp-Gly-Pro-Hyp-Gly-Pro-Hyp-Gly-Ala-OrnR-Gly-Leu-Thr-Gly-OrnR-Hyp-Gly-Asp-Ala-Gly-Pro-Hyp-Gly-Pro-Hyp | (SEQ ID NO:75) |

Example 8

Capturing Antibodies

Triple helical polypeptide complexes [(Gly-Pro-Hyp)$_5$-CII$_{(358-366Hyp-369)}$-(Gly-Pro-Hyp)$_2$]$_3$L$_{Ahx}$, [(Gly-Pro-Hyp)$_5$-CII$_{(259-273Hyp-274)}$-(Gly-Pro-Hyp)$_2$]$_3$L$_{Ahx}$, [(Gly-Pro-Hyp)$_5$-CII$_{(259-273Hyp-274)}$-CII$_{(359-366Hyp)}$-(Gly-Pro-Hyp)$_2$]$_3$L$_{Ahx}$, [(Gly-Pro-Hyp)$_5$-CII$_{(494-504Hyp)}$-(Gly-Pro-Hyp)$_2$]$_3$L$_{Ahx}$, and [(Gly-Pro-Hyp)$_5$-CII$_{(551-552Hyp-564)}$-(Gly-Pro-Hyp)$_2$]$_3$L$_{Ahx}$ were used in an ELISA to detect anti-CII-antibodies. Specifically, Immulon2 HB (Dynex/Technologies Inc., USA) plates were coated with [(Gly-Pro-Hyp)$_5$-CII$_{(358-366Hyp-369)}$-(Gly-Pro-Hyp)$_2$]$_3$L$_{Ahx}$, [(Gly-Pro-Hyp)5-CII$_{(259-273Hyp-274)}$-(Gly-Pro-Hyp)$_2$]$_3$L$_{Ahx}$, [(Gly-Pro-Hyp)$_5$-CII$_{(259-273Hyp-274)}$-CII$_{(359-366Hyp)}$-(Gly-Pro-Hyp)$_2$]$_3$L$_{Ahx}$, [(Gly-Pro-Hyp)$_5$-CII$_{(494-504Hyp)}$-(Gly-Pro-Hyp)$_2$]$_3$L$_{Ahx}$, and [(Gly-Pro-Hyp)$_5$-CII$_{(551-552Hyp-564)}$-(Gly-Pro-Hyp)$_2$]$_3$L$_{Ahx}$ in a volume of 50 µL/well and at a concentration of 5 µg/mL. Wells coated with native rat CII (rCII; 10 µg/mL) were used as a positive control, while negative controls included wells coated with native rat type I collagen (rCI; 10 µg/mL) and wells coated with phosphate-buffered saline (PBS; pH 7.4).

After coating, the plates were incubated for at least one hour in a humid chamber at 4° C. After incubation, the plates were washed three times with PBS using an automatic microtiter plate-washing device (Skan Washer 300, Skatron instruments) and incubated with 50 µL/well of bovine serum albumin (BSA; Sigma, St. Louis, Mo.; 10 mg/mL in PBS) for two hours at 20° C. The wells were washed five times with PBS using ELISA washing equipment (Skatron, Norway) and incubated with a monoclonal anti-CII antibody (50 µL/well in titrated concentrations) for two hours at 20° C. After this two hour incubation, the plates were washed with PBS-Tween and incubated with a secondary enzyme-labeled antibody for two hours at 20° C. For detection of mouse antibodies, peroxidase labeled goat anti-mouse IgG (H+L) (Jackson ImmunoResearch Laboratories, Inc., USA) were used. For detection of rat antibodies, peroxidase labeled goat anti-rat IgG (H+L) (Jackson ImmunoResearch Laboratories, Inc. USA) were used.

After washing the wells with PBS, the assay was developed using the ABTS system (Boehringer-Mannheim, Mannheim, Germany), and the absorbance levels determined at 405 nm (ELISA reader, Titertek). Titers and concentrations of the monoclonal antibodies were calculated using limiting dilution (ELISA software: HyperELISA 3.0).

Each tested polypeptide complex captured a distinct subset of the anti-CII antibodies (Table 3). In some cases, the polypeptide complex and the native rCII polypeptide captured equivalent amounts of an anti-CII antibody. In other cases, the polypeptide complex captured more of an anti-CII antibody than the native rCII polypeptide. These results indicate that the polypeptide complexes described herein can detect various CII epitopes within the context of a triple helical polypeptide composition.

TABLE 3

Polypeptide complexes capture anti-CII antibodies.

| Monoclonal antibody | Species origin | B cell epitope (end point titer value in ng antibody/mL) | | | | | |
|---|---|---|---|---|---|---|---|
| | | A | B | C | D | E | rCII |
| 122.9 | Rat | — | <10 | <10 | — | — | 10 |
| 125.5 | Rat | 10 | — | — | — | — | 10 |
| 126.35 | Rat | 10 | — | — | — | — | 10 |
| 145.322 | Rat | 10 | — | — | — | — | 100 |
| 146.50 | Rat | 10 | — | — | — | — | 100 |
| 126.30 | Rat | — | — | — | 10 | — | 10 |
| M2 87 | Mouse | — | — | — | — | <10 | 10 |
| M2 84 | Mouse | — | — | — | — | <10 | 10 |
| M2 88 | Mouse | — | — | — | — | 100 | 10 |
| M2 76 | Mouse | — | — | — | — | <10 | 10 |
| M2 139 | Mouse | — | — | — | — | <10 | 10 |
| EB63 | Mouse | <10 | — | 100 | — | — | 100 |
| EB2 | Mouse | 1000 | — | 100 | — | — | <10 |

A = [(Gly-Pro-Hyp)$_5$-CII$_{(358-366Hyp-369)}$-(Gly-Pro-Hyp)$_2$]$_3$L$_{Ahx}$
B = [(Gly-Pro-Hyp)$_5$-CII$_{(259-273Hyp-274)}$-(Gly-Pro-Hyp)$_2$]$_3$L$_{Ahx}$
C = [(Gly-Pro-Hyp)$_5$-CII$_{(259-273Hyp-274)}$-CII$_{(359-366Hyp)}$-(Gly-Pro-Hyp)$_2$]$_3$L$_{Ahx}$
D = [(Gly-Pro-Hyp)$_5$-CII$_{(494-504Hyp)}$-(Gly-Pro-Hyp)$_2$]$_3$L$_{Ahx}$
E = [(Gly-Pro-Hyp)$_5$-CII$_{(551-552Hyp-564)}$-(Gly-Pro-Hyp)$_2$]$_3$LAhx

Figure 7:
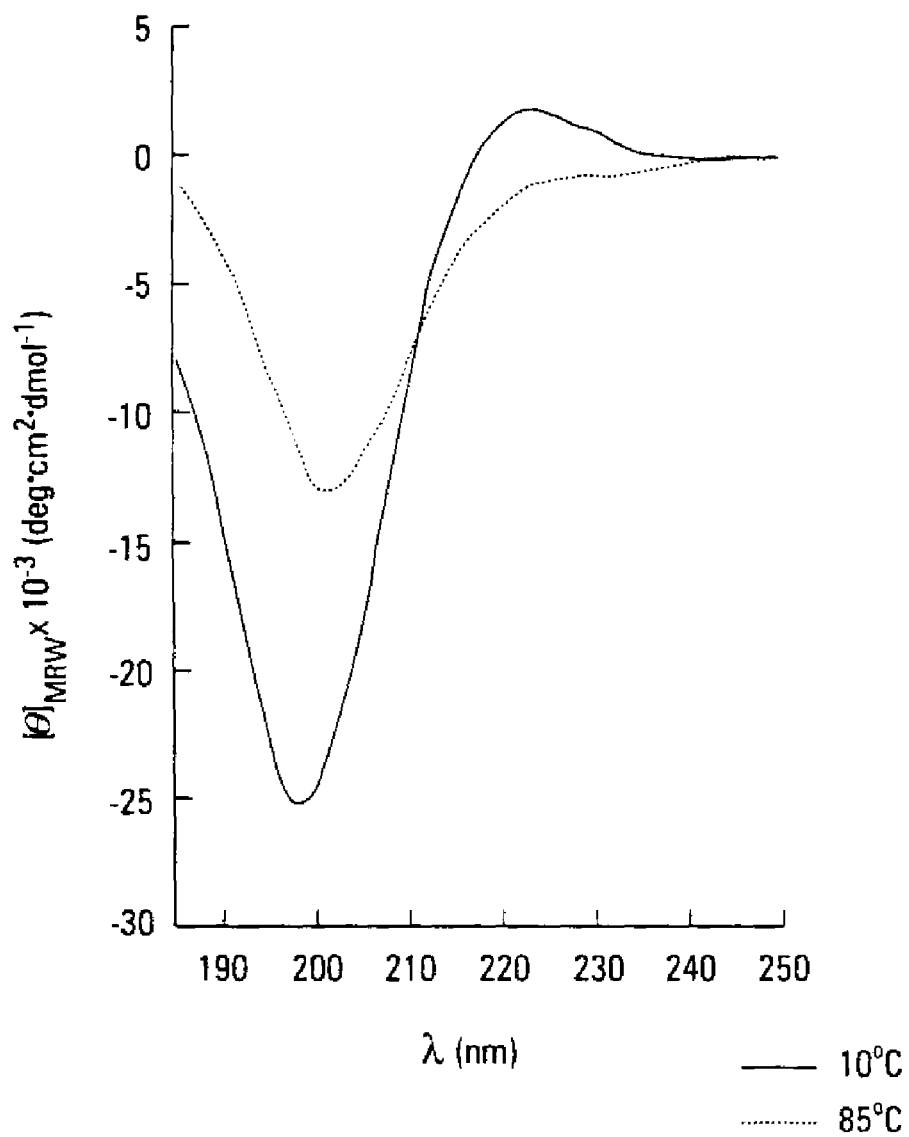
FIG. 7 is a graph plotting molar elipticity ($[\theta]$) verses X for $[(Gly-Pro-Hyp)_5-CII_{(358-366Hyp-369)}-(Gly-Pro-Hyp)_2]3L_{Ahx}$ as assessed by circular dichroism spectroscopy.

Circular dichroism (CD) spectroscopy was used to assess the triple helical conformation of the [(Gly-Pro-Hyp)5-CII$_{(358-366Hyp-369)}$-(Gly-Pro-Hyp)$_2$]$_3$L$_{Ahx}$ and [(Gly-Pro-Hyp)$_5$-CII$_{(551-552Hyp-564)}$-(Gly-Pro-Hyp)$_2$]$_3$L$_{Ahx}$ polypeptide compositions. At low temperatures, [(Gly-Pro-Hyp)$_5$-CII$_{(358-366Hyp-369)}$-(Gly-Pro-Hyp)$_2$]$_3$L$_{Ahx}$ exhibited typical features of a collagen-like conformation. Specifically, [(Gly-Pro-Hyp)$_5$-CII$_{(358-366Hyp-369)}$ (Gly-Pro-Hyp)$_2$]$_3$L$_{Ahx}$ exhibited a large negative molar elipticity ([θ]) at λ=200 nm and a positive [θ] at λ=225 nm (FIG. 7). The CD-characteristics of a triple helical molecule were lost upon heat denaturation (FIG. 7). [(Gly-Pro-Hyp)$_5$-CII$_{(551-552Hyp-564)}$-(Gly-Pro-Hyp)$_2$]$_3$L$_{Ahx}$ exhibited similar CD-characteristics as those exhibited for [(Gly-Pro-Hyp)$_5$-CII$_{(358-366Hyp-369)}$-(Gly-Pro-Hyp)$_2$]$_3$L$_{Ahx}$.

Microtiter plates (Nunc, Wiesbaden, Germany) were coated overnight with [(Gly-Pro-Hyp)$_5$-CII$_{(358-366Hyp-369)}$-(Gly-Pro-Hyp)$_2$]$_3$L$_{Ahx}$ or [(Gly-Pro-Hyp)$_5$-CII$_{(551-552Hyp-564)}$-(Gly-Pro-Hyp)$_2$]$_3$L$_{Ahx}$ at 4° C. and blocked with 2% BSA in phosphate buffered saline (PBS, pH 7.4) for one hour. The presentation of a native collagen conformation on the plastic surface of the microtiter well was controlled by the immunoreactivity of two mouse monoclonal antibodies (C1 mAb having specificity for the CII$_{(358-369)}$ region and M2.139 mAb having specificity for the CII$_{(551-564)}$ region) that recognize the CII epitopes in a conformation dependent manner as confirmed in FIG. 8. Identical titration curves for the native CII and the synthetic polypeptides indicate that the synthetic polypeptides have a perfect image of the conformational epitope. In contrast, the mAB does not bind to heat denatured CII. Heat denaturation was achieved by heating the CII polypeptide to greater than 50° C. for two hours prior to the coating of the microtiter wells.

Human IgG autoantibodies to epitopes on the synthetic collagens were determined by adding serum samples diluted in phosphate buffered saline (PBS) to microtiter wells coated with [(Gly-Pro-Hyp)$_5$-CII$_{(358-366Hyp-369)}$-(Gly-Pro-Hyp)$_2$]$_3$L$_{Ahx}$ for one hour at room temperature. Antibody binding was detected using horseradish peroxidase-conjugated rabbit anti-human IgG (Dianova, Hamburg, Germany) and 2,2-azino-di-[3-ethylbenzthiazoline sulfonate] diamonium salt as substrate (ABTS tablets, Boehringer, Mannheim, Gemany).

Figure 9:
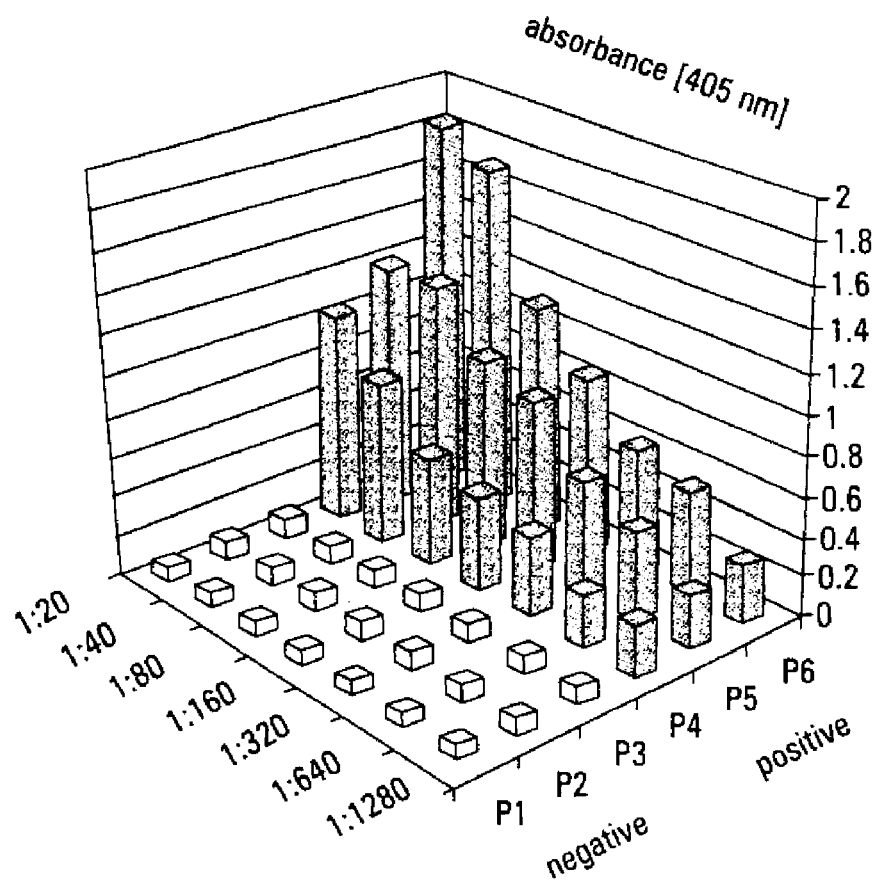
FIG. 9 is a three-dimensional graph plotting ELISA reactivity (absorbance at 405 nm) for diluted serum binding to $[(Gly-Pro-Hyp)_5-CII_{(358-366Hyp-369)}-(Gly-Pro-Hyp)_2]_3 L_{Ahx}$.

The titration curves of sera obtained from three RA patients (P4, P5, and P6) contained IgG autoantibodies having specificity for CII$_{(358-366)}$ as evidenced by binding to [(Gly-Pro-Hyp)$_5$-CII$_{(358-366Hyp-369)}$-(Gly-Pro-Hyp)$_2$]L$_{Ahx}$ in a concentration dependant manner. In contrast, titration curves of sera obtained from three RA patients (P1, P2, and P3) did not contain IgG autoantibodies having specificity for CII$_{(358-366)}$ as evidenced by the lack of binding to [(Gly-Pro-Hyp)$_5$-CII$_{(358-366Hyp-369)}$-(Gly-Pro-Hyp)$_2$]$_3$L$_{Ahx}$ regardless of concentration (FIG. 9). These results demonstrate that RA patients contain autoantibodies that recognize CII epitopes. In addition, these results demonstrate that the polypeptide complexes described herein have the appropriate conformation and can be used to detect autoantibodies present within RA patients.

Sera derived from different cohorts of patients were analyzed at a standard dilution of 1:100 PBS for the presence of CII$_{(358-369)}$- or CII$_{(551-564)}$-specific IgG autoantibodies. The sera were derived from rheumatoid arthritis patients (n=48) and from control cohorts of patients with osteoarthritis (OA; n=22), systemic lupus erythematosus (SLE; n=38), relapsing polychondritis (RP; n=26), and patients diagnosed with no rheumatic disease (NHD, n=19). All patents in the RA- and SLE-cohort fulfilled the classification criteria of the American College of Rheumatology (ACR) in their updated versions (Arnett et al., *Arthritis Rheum.*, 31:315 (1988) and Altman et al., *Arthritis Rheum.*, 34:505 (1991)). All OA-patients met the ACR-criteria for OA in the hip or the knee joint (Altman et al., *Arthritis Rheum.*, 29:1039 (1986)), and the diagnosis of RP based on the criteria of Michet et al. (*Ann. Intern. Med.*, 104:74–78 (1986)). For the evaluation of statistical differences in immunoreactivity and clinical parameters between the different cohorts (RA, OA, RP, SLE, and NHD), the Mann-Whitney-U-test was applied.

Figure 10:
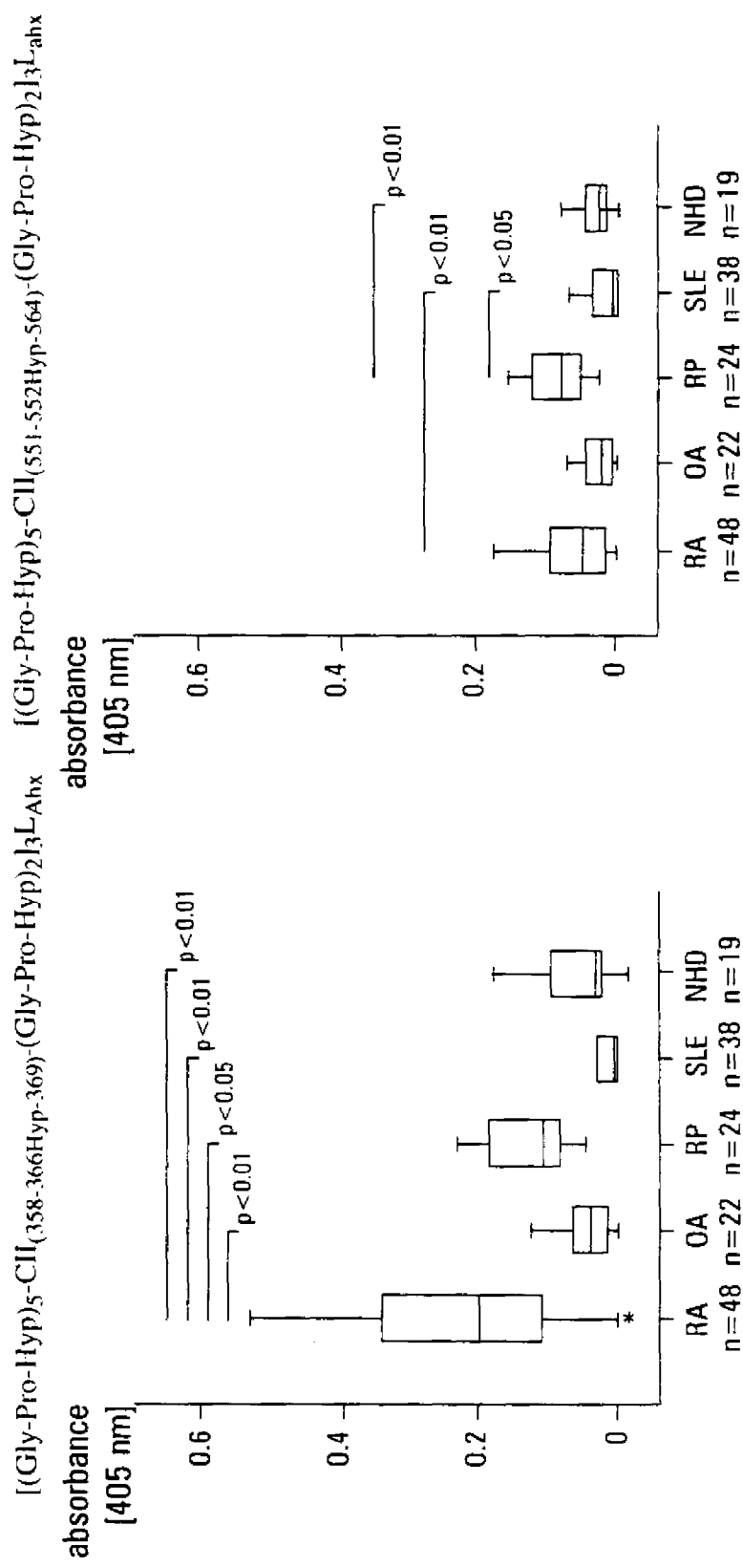
FIG. 10 is a bar graph plotting ELISA reactivity (absorbance at 405 nm) detected in the indicated patient cohorts using either $[(Gly-Pro-Hyp)_5-CII_{(358-366Hyp-369)}-(Gly-Pro-Hyp)_2]_3L_{Ahx}$- or $[(Gly-Pro-Hyp)_5-CII_{(551-552Hyp-564)}-(Gly-Pro-Hyp)_2]_3L_{Ahx}$-coated plates. $95^{th}$ and $75^{th}$ percentiles are shown, and the bold horizontal lines indicate the median values. Significant differences in absorbance at 405 nm are indicated. The p-values were calculated according to the Mann-Whitney u-test; (n.s.=not significant).
Figure 11:
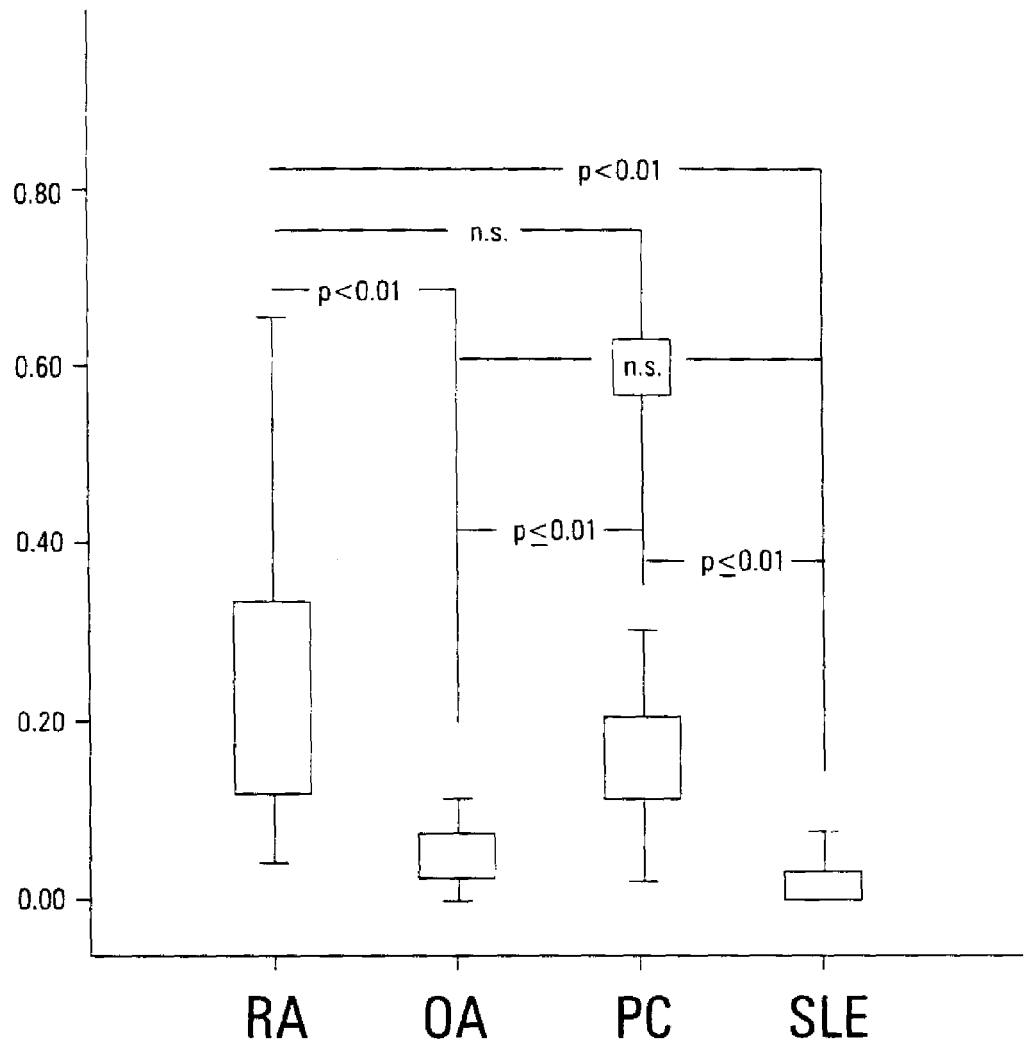
FIG. 11 is a bar graph plotting ELISA reactivity (absorbance at 405 nm) detected in the indicated patient cohorts using $[(Gly-Pro-Hyp)_5-CII_{(494-504Hyp)}-(Gly-Pro-Hyp)_2]_3 L_{Ahx}$-coated plates. $95^{th}$ and $75^{th}$ percentiles are shown, and the bold horizontal lines indicate the median values. Significant differences in absorbance at 405 nm are indicated. The p-values were calculated according to the Mann-Whitney u-test; (n.s.=not significant).

An enhanced binding of IgG autoantibodies to the CII$_{(358-369)}$ epitope containing polypeptide complex ([(Gly-Pro-Hyp)$_5$-CII$_{(358-366Hyp-369)}$-(Gly-Pro-Hyp)$_2$]$_3$L$_{Ahx}$ was detectable in the RA sera (FIG. 10). This result on the preferential recognition of the CII$_{(358-369)}$ epitope by RA-derived autoantibodies was highly significant compared to data obtained with serum samples from all other cohorts. However, a slight increase in IgG binding to [(Gly-Pro-Hyp)$_5$-CII$_{(358-366Hyp-369)}$-(Gly-Pro-Hyp)$_2$]$_3$L$_{Ahx}$ coated microtiter wells above the level measured in the OA, SLE, and NHD sera was detectable in the RP-derived samples. In contrast to the results for immunorecognition of the [(Gly-Pro-Hyp)$_5$-CII$_{(358-366Hyp-369)}$-(Gly-Pro-Hyp)2]$_3$L$_{Ahx}$ polypeptide composition, IgG binding to [(Gly-Pro-Hyp)$_5$-CII$_{(551-552Hyp-564)}$-(Gly-Pro-Hyp)$_2$]$_3$L$_{Ahx}$ was hardly detectable in any of the serum samples investigated. Despite a tendency of slightly increased absorbance values obtained with RA and RP sera, the absolute measures and the quantitative differences to the respective OA, SLE, and NHD controls remained rather low indicating that the CII$_{(551-564)}$ sequence was not a major target of CII-directed autoantibody responses in all samples analyzed. Thus, a comparison of all ELISA data obtained with the two synthetic polypeptide complexes in different cohorts of patients revealed a selective association of CII$_{(358-369)}$-specific IgG autoantibodies with RA. Analogous ELISA results of a preferential recognition by RA-derived serum IgG were also shown for [(Gly-Pro-Hyp)$_5$-CII$_{(494-504Hyp)}$-(Gly-Pro-Hyp)$_2$]$_3$L$_{Ahx}$, a synthetic triple helical collagen peptide containing the $CII_{(494-504)}$ epitope (FIG. 11). Absorbance values for binding of circulating IgG to $[(Gly-Pro-Hyp)_5-CII_{(494-504Hyp)}-(Gly-Pro-Hyp)_2]_3L_{Ahx}$ were elevated in RA-patients although the quantitative differences did not reach the level of significance for comparison with the results obtained in the RP-cohort.

Example 9

Identifying T cells clones

Langerhans cells (dendritic cells) were prepared from ear skin of B10Q×DBA/1 mice and purified with selection on N418 marker. Once purified, Langerhans cells were mixed with HCQ.4 T cell hybridoma cells ($1\times10^5$ cell/well), and the mixture incubated with media containing 10 µg/mL of $[(Gly-Pro-Hyp)_5-CII_{(259-274)}-(Gly-Pro-Hyp)_2]_3L_{Ahx}$ (a linked polypeptide), $CII_{(259-270)}$ (an unlinked polypeptide), or native rat CII for 24 hours. After the 24-hour incubation, 0.5 µCi $^3H$-thymidine/well (Radiochemical Centre, Amersham, UK) was added, and the cells incubated for an additional 18 hours. After this incubation, the supernatants were assayed for IL-2 content using a CTLL assay. Results were presented as means of duplicates.

The linked polypeptide composition stimulated T cells, while the unlinked polypeptide composition and native rat CII polypeptides did not (FIG. 3). In addition, the amount of stimulation increased with the number of dendritic cells until saturated at about 7500 cells. These results indicate that the polypeptide compositions described herein can be used to detect T cell clones. In addition, these results indicate that linked polypeptide compositions are more efficacious in detecting T cell clones than the same unlinked polypeptide compositions.

In a separate experiment, peripheral blood monocytes (PBMC) from RA patients were separated using Histoprep (BAG, Lich, Germany) and cultured overnight at 37° C. and 5% $CO_2$ in RPMI 1640 (Life Technologies GmbH, Karlsruhe, Germany) supplemented with 1% L-glutamine (Life Technologies GmbH), 100 U/mL penicillin, 0.1 mg/mL streptomycin (Life Technologies GmbH), and 10% autologous serum. For antigenic stimulation of $1\times10^6$ PBMC, 10 µg of $CII_{(259-273)}$, $CII_{(259-264GHyl-273)}$, $CII_{(259-270GHyl-273)}$, and $CII_{(259-264GHyl-270GHyl-273)}$ as well as 1 µg anti-human CD28 (Becton Dickinson GmbH Heidelberg, Germany) were added per mL of culture medium. The $CII_{(259-264GHyl-273)}$ polypeptide composition contained a glycosylated hydroxylysine residue at position 264, the $CII_{(259-270GHyl-273)}$ polypeptide composition contained a glycosylated hydroxylysine residue at position 270, and the $CII_{(259-264GHyl-270GHyl-273)}$ polypeptide composition contained a glycosylated hydroxylysine residues at positions 264 and 270. In each case, the carbohydrate moiety was a single D-galactose residue.

T cell receptor specific responses were controlled in parallel using culture conditions that either omitted any stimulation or only exposed the cells to the costimulatory anti—CD28 antibody overnight in the absence of a polypeptide composition. T-cell responsiveness to a common recall antigen was tested in parallel cultures of PBMC using 10 µg/mL tetanus toxoid (TT; Calbiochem-Novabiochem GmbH, Schwalbach, Germany) and anti-CD28 for stimulation. Monensin (2.5 mM; Sigma-Aldrich, Wimborne, U.K.) was added to the overnight cultures, and the cells were incubated for additional four hours before harvesting. Subsequently, the cells were washed twice in PBS and fixed in 4% paraformaldehyde/PBS solution for seven minutes at 37° C. followed by a repeated washing procedure in PBS. A permeabilisation step was performed for 10 minutes with 0.5% Saponin/1% BSA/0.1% $NaN_3$ in PBS. Afterwards, the cells were washed twice with PBS/1% BSA. The cells were stained with 0.2 µg rat anti-human IL2-PE (Becton Dickinson) and 3 µL CD4-FITC or CD3-FITC (Beckman Coulter, Krefeld, Germany) for 20 minutes at 4° C. Fluorescence intensities were determined using a Coluter Epics XL-MCL™ flow cytometer and System-II™ software. Large activated lymphocytes (blasts) were gated according to forward and side scatter as described previously (Assenmacher et al., *Eur. J. Immunology*, 23:523–529 (1993) and Assenmacher et al., *Eur. J. Immunology* 28:1534–1543 (1998)). Cells not treated with saponin, thus not permeabilized, were used to exclude background staining of anti-IL2 antibody.

Figure 12:
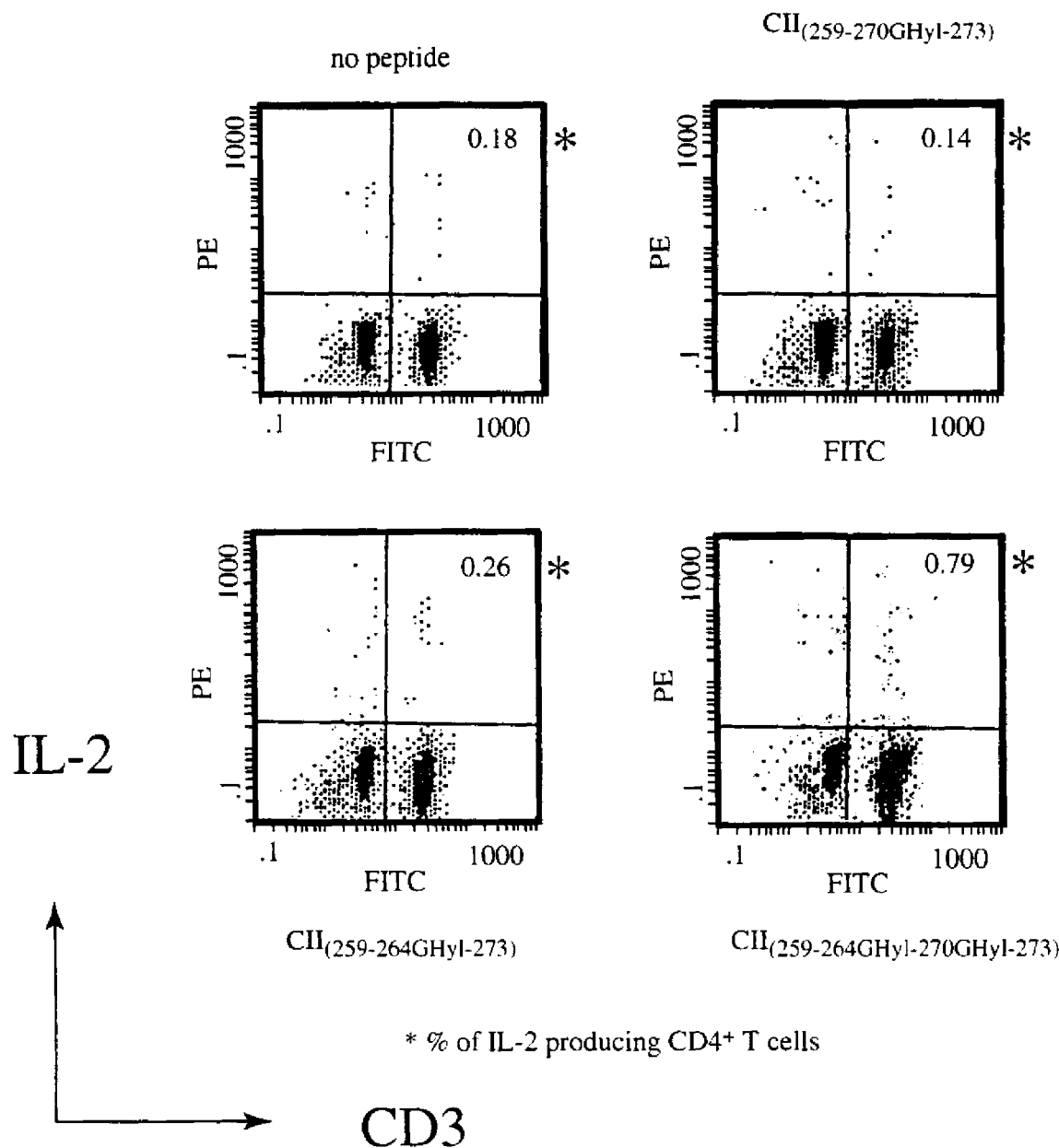
FIG. 12 is a series of plots of two-color flow cytometry of in vitro stimulated T cells from RA patients. The X-axis represents fluorescence intensities for binding of a FITC-labelled anti-CD3 antibody, whereas the y-axis represents signal intensities for binding of a PE-labelled anti-IL-2 antibody. The cells were gated on the population large lymphoblasts according to the forward side scatter. The upper right quadrant of the different panels (indicated by *) represents the percentage of double positive cells.

The cell sample incubated with the $CII_{(259-264GHyl-270GHyl-273)}$ polypeptide composition contained more IL-2-producing T cells than the samples incubated with either the $CII_{(259-264GHyl-273)}$ polypeptide composition or the $CII_{(259-270GHyl-273)}$ polypeptide composition (FIG. 12). These results indicate that RA patients have more T cells that recognize the polypeptide composition containing two glycosylated residues as compared to T-cells that recognize the polypeptide compositions containing only one glycosylated residue.

Figure 13:
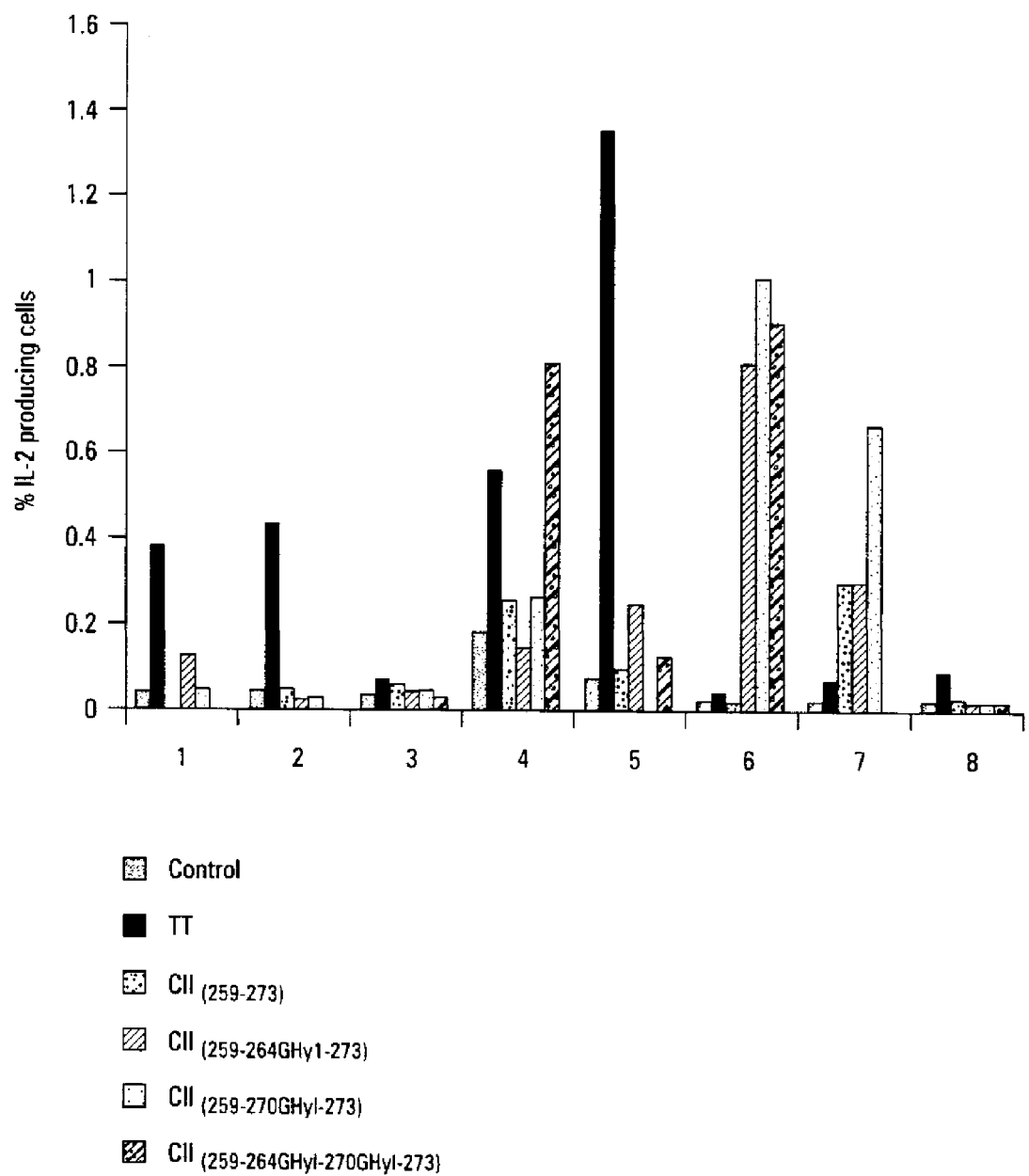
FIG. 13 is a bar graph plotting the percent IL-2-producing CD3[+] T cells present within samples obtained from RA patients. Each sample was treated with either no polypeptide composition (control), tetanus toxoid (TT), or the indicated polypeptide composition.

The percent of IL-2-producing T-cell present within samples (1) obtained from eight different RA patients and (2) stimulated with either $CII_{(259-273)}$, $CII_{(259-264GHyl-273)}$, $CII_{(259-270GHyl-273)}$, and $CII_{(259-264GHyl-270GHyl-273)}$ was determined by two color flow cytometry (FIG. 13). The control was T cells cultured in the presence of the costimulatory anti-CD28 antibody without a polypeptide composition. The recall response to tetanus toxoid (TT) was shown for comparison. Whereas the T cells from patients 2, 3, and 8 did not respond to any of the polypeptide compositions, there was a clear recognition of the $CII_{(259-264GHyl-270GHyl-273)}$ polypeptide composition by the T-cells from patient 4 (FIG. 13). In addition, the T cells from patient 6 recognized the three polypeptide compositions containing at least one glycosylated residue but not the unglycosylated $CII_{(259-273)}$ polypeptide composition (FIG. 13). The T cells from patient 7 preferentially recognized the $CII_{(259-270GHyl-273)}$ polypeptide composition, while the T cells from patient 1 moderately recognized the $CII_{(259-264GHyl-273)}$ polypeptide composition (FIG. 13).

In another experiment, the percent of IL-2-producing $CD4^+$ T cells was determined by two-color flow cytometry for samples obtained from three RA patients (A, B, and C) as well as one normal healthy donor (NHD). The experimental conditions were the same as described above with the exception that the T cells were stained for the CD4 marker. RA patient 1 had T cells that preferentially recognized the $CII_{(259-273)}$ polypeptide composition, while RA patient 2 had T cells that recognized both the $CII_{(259-264GHyl-273)}$ polypeptide composition and the $CII_{(259-270GHyl-273)}$ polypeptide composition (Table 4). The T cells from the normal healthy donor were stimulated by the TT but not the four tested polypeptide compositions.

TABLE 4

IL-2 response of CD4+ T cells upon in vitro stimulation with different polypeptide compositions.

| patient | Control (no peptide) | TT | A | B | C | D |
|---|---|---|---|---|---|---|
| RA 1 | 0.01 | 0.38 | 0.31 | 0.17 | 0.18 | 0.14 |
| RA 2 | 0.05 | 0.61 | 0.07 | 0.41 | 0.48 | 0.07 |
| RA 3 | 0.04 | 0.20 | 0.02 | 0.03 | 0.01 | 0.03 |
| NHD | 0.03 | 0.15 | 0.02 | 0.04 | 0.03 | 0.03 |

A = $CII_{(259-273)}$ polypeptide composition
B = $CII_{(259-264GHyl-273)}$ polypeptide composition
C = $CII_{(259-270GHyl-273)}$ polypeptide composition
D = $CII_{(259-264GHyl-270GHyl-273)}$ polypeptide composition Taken together, these results demonstrate that specific T cell responses are directed to CII epitopes in a manner influenced by the carbohydrate modification of positions 264 and 270. In addition, these results demonstrate that T cell responses vary in quality and quantity between individual RA patients. These results also indicate that human T cells can be detected with glycosylated single chain polypeptides and that increased detection can be accomplished using triple helical polypeptide compositions of glycosylated polypeptides that are linked via one or more interpolypeptide linkages.

Example 10

Enhancing Protection Against Arthritis in Newborns

MMC transgenic newborn C3H.Q mice were vaccinated with an unlinked polypeptide composition or unlinked polypeptide composition containing either a hydroxylated amino acid residue or a glycosylated hydroxylated amino acid residue. MMC transgenic mice express a mutated mouse CII that has position 266 mutated to contain glutamic acid instead of aspartic acid. In addition, non-transgenic newborn C3H.Q mice were vaccinated with unlinked polypeptides, unlinked polypeptides containing a hydroxylated amino acid residue, or unlinked polypeptides containing a glycosylated hydroxylated amino acid residue. In each experiment, mice treated with PBS were used as negative controls. Specifically, the mice were injected intraperitoneally with 100 µL of an emulsion containing the polypeptide or PBS with incomplete Freund's adjuvant within 48 hours of birth. The polypeptides used for vaccination were (1) $CII_{(256-270)}$, a non-glycosylated, unlinked polypeptide that contains $CII_{(256-270)}$; (2) $CII_{(256-264Hyl-270)}$, a hydroxylated, unlinked polypeptide that contains $CII_{(256-270)}$ with a hydroxylysine (Hyl) residue at position 264; and (3) $CII_{(256-264GHyl-270)}$, a glycosylated, unlinked polypeptide that contains $CII_{(256-270)}$ with a glycosylated hydroxylysine (GHyl) residue at position 264. The glycosylation moiety of 264 GHyl was a single D-galactose residue.

Eight weeks after vaccination, the mice were treated with rat CII emulsified in complete Freund's adjuvant to induce arthritis. Specifically, each mouse received 100 µL containing 100 µg of rat CII injected intradermally around the base of the tail. After treatment, the mice were observed for the development of arthritis. In addition, five weeks after treating the mice with rat CII, blood samples were collected to determine the antibody response.

Figure 4:
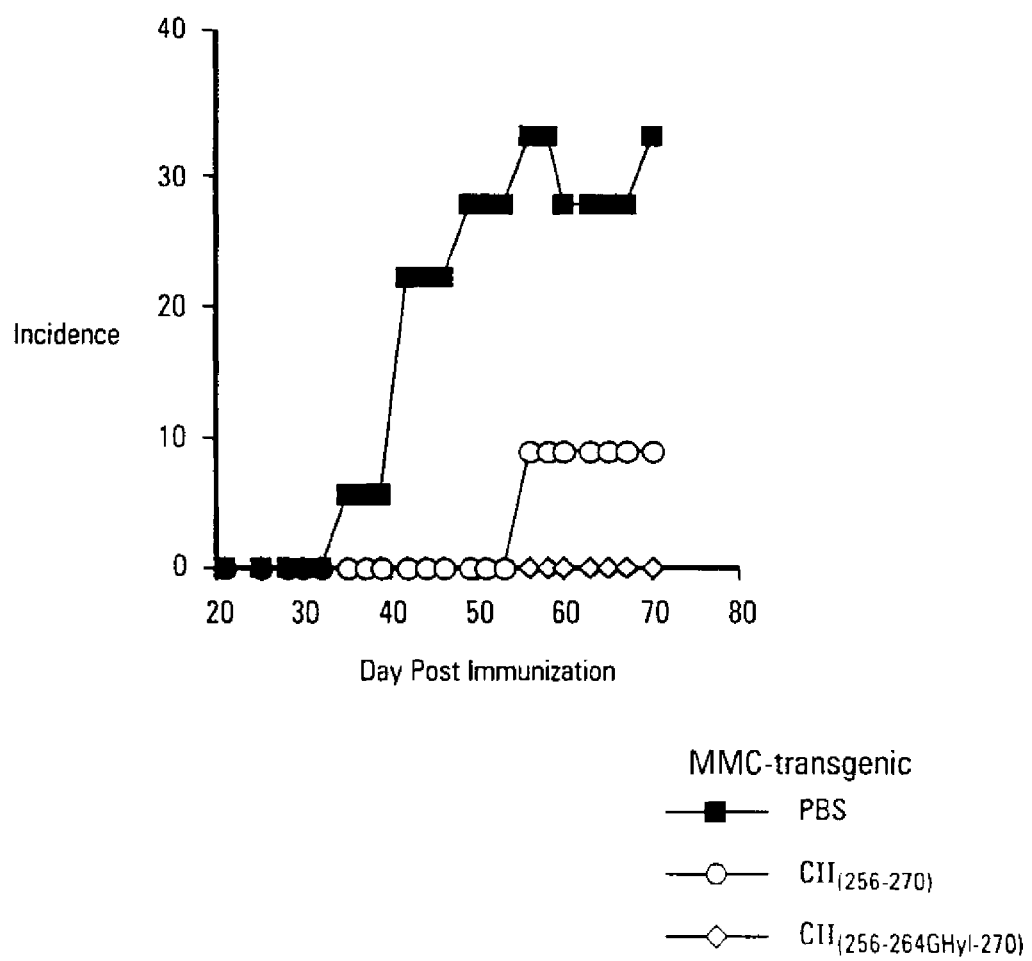
FIG. 4 is a line graph plotting percent incidence (frequency of arthritis) versus days post immunization for neonatal transgenic mice vaccinated with PBS, $CII_{(256-270)}$, or $CII_{(256-264GHyl-270)}$.
Figure 5:
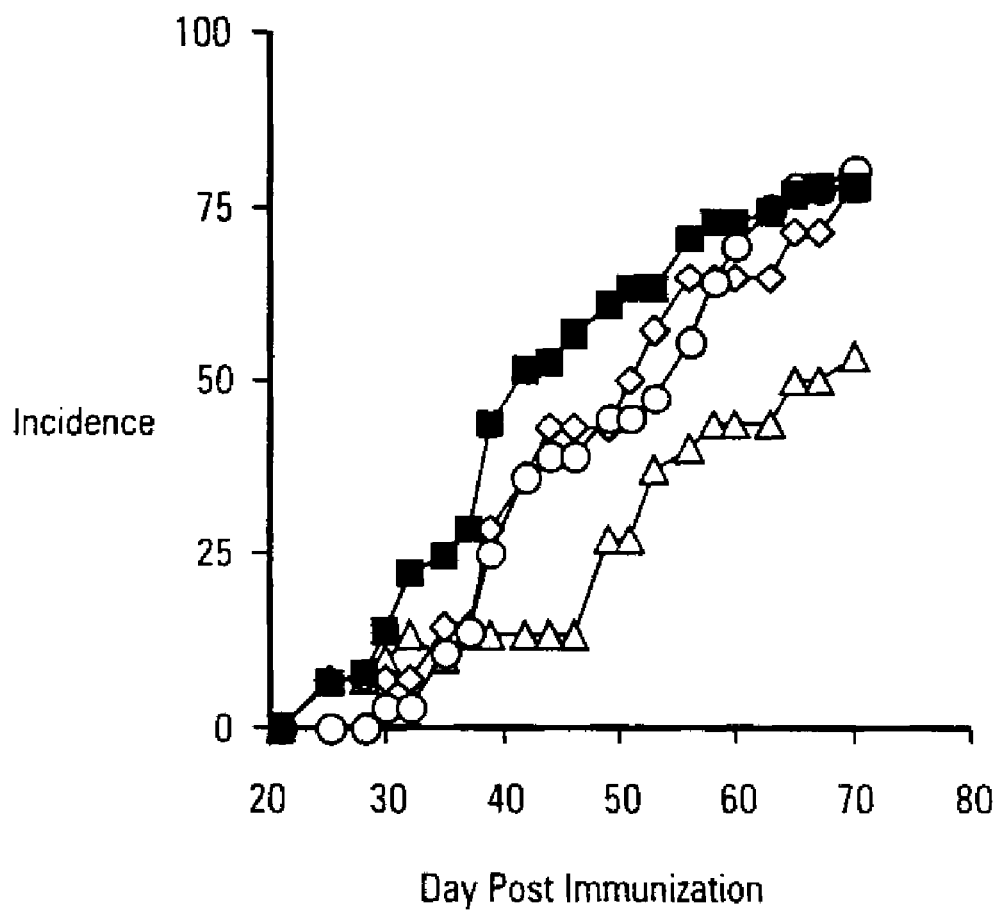
FIG. 5 is a line graph plotting percent incidence (frequency of arthritis) versus days post immunization for neonatal non-transgenic mice vaccinated with PBS, $CII_{(256-270)}$, $CII_{(256-264Hyl-270)}$, or $CII_{(256-264GHyl-270)}$.

The $CII_{(256-264GHyl-270)}$ polypeptide was the most effective vaccine in both MMC transgenic and non-transgenic mice (FIGS. 4 and 5). Thus, glycosylated hydroxylated amino acid residues can enhance the level of protection induced by a polypeptide vaccine. In addition, animals vaccinated with $CII_{(256-264GHyl-270)}$ had a reduced level of anti-CII specific antibody response five weeks after inducing arthritis with the rat CII.

Example 11

Enhancing Protection Against Arthritis in Adults

Male and female C3H.Q mice were used in two separate experiments. In each experiment, adult mice 8–12 weeks old were injected intradermally at the base of the tail with $CII_{(256-270)}$ (unlinked polypeptides), $[(Gly-Pro-Hyp)_5-CII_{(259-274)}-(Gly-Pro-Hyp)_2]_3L_{Ahx}$ (linked polypeptides), or PBS. Specifically, each mouse received 100 µL of PBS or 100 µL of polypeptide (100 µg) emulsified in incomplete Freund's adjuvant.

After three weeks, the mice were treated with rat CII emulsified in complete Freund's adjuvant. Specifically, each mouse received 100 µL containing 100 µg of rat CII injected intradermally around the base of the tail. After treatment, the mice were observed for the development of arthritis. In addition, five weeks after treating the mice with rat CII, blood samples were collected to determine the antibody response.

Figure 6:
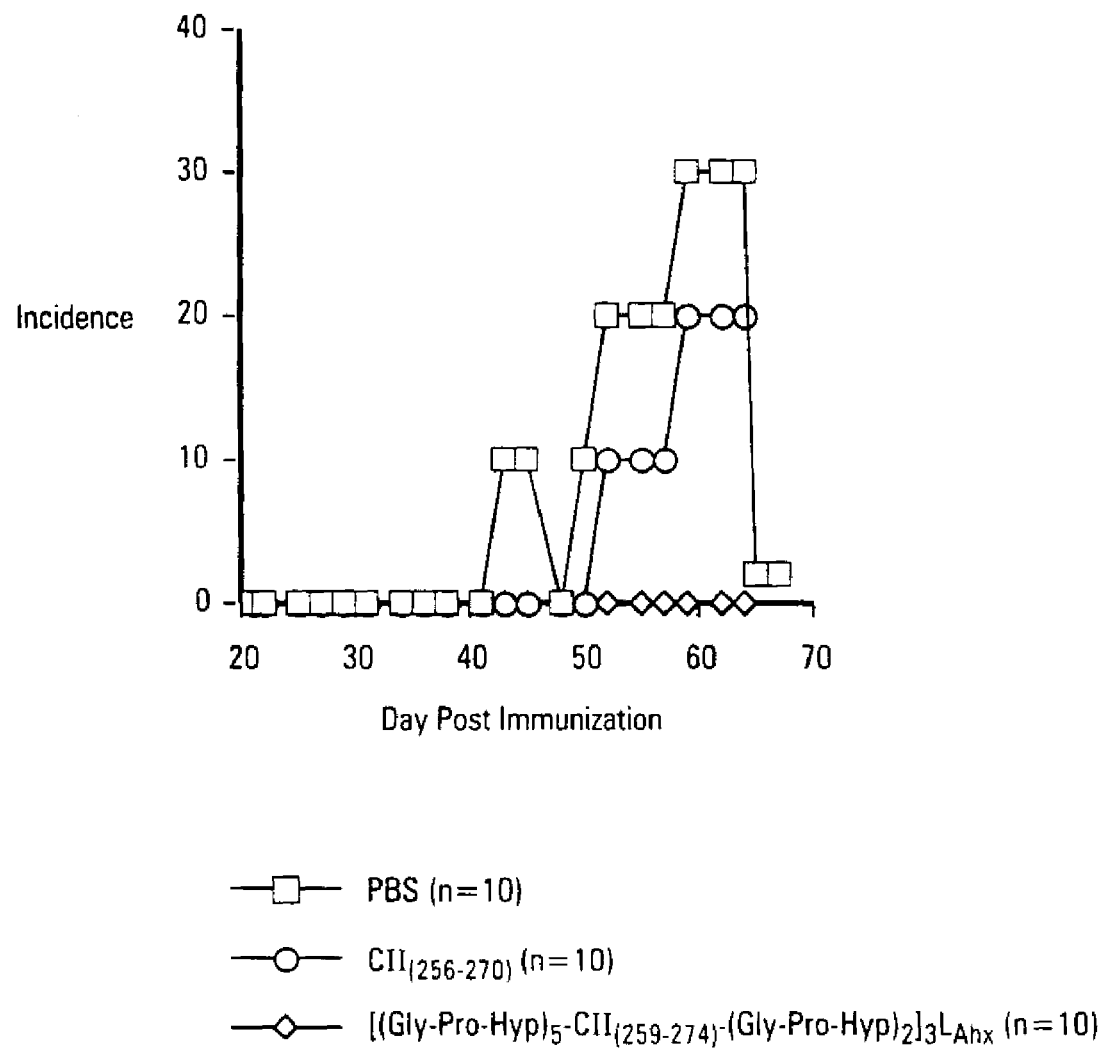
FIG. 6 is a line graph plotting percent incidence (frequency of arthritis) versus days post immunization for adult female mice vaccinated with PBS, $CII_{(256-270)}$, or $[(Gly-Pro-Hyp)_5-CII_{(259-274)-(Gly-Pro-Hyp)_2}]_3L_{Ahx}$.

Vaccination with the linked polypeptide composition abrogated development of arthritis, while the unlinked polypeptide composition had no significant effect (FIG. 6). In addition, the antibody response was lower in mice vaccinated with the linked polypeptide composition.

Example 12

Treatment of Arthritis

Collagen induced arthritis (CIA) is an experimental model for rheumatoid arthritis. Mice of the H2q haplotype develop CIA after immunization with rat type II collagen (CII). An immunodominant T cell epitope is located at amino acid position $CII_{(256-270)}$. This epitope can also become post-translational modified by hydroxylation of lysine residues and further glycosylated with mono- or di-saccharides. The H2q mice that have a transgenic expression of the immunodominant epitope were used. The epitope was expressed in type I collagen (CI) and therefore systemically spread. By this, the epitope specific T cells were inactivated, and the transgenic mice resistant to CIA.

By transplanting skin from transgenic mice to non-transgenic, CIA susceptible littermates were introduced to the immunodominant T cell epitope peripherally. By grafting either normal or thymectomized wild type mice with transgenic skin that contained the heterologous $CII_{(256-270)}$ epitope, experiments were performed to sort out how this partial tolerance towards CII can be induced, maintained, and eventually broken. Changes in CIA susceptibility as well as the in vitro responses were studied.

By introducing this immunodominant T cell epitope to the peripheral part of the immune system, epitope specific T-cells become tolerized. The tolerance induced by transplantation of TSC-skin was mainly directed towards the non-glycosylated variant of the epitope. Furthermore, introduction of the heterologous T cell epitope by skin transplantation protected the recipients from arthritis. Transgenic CII extracted from grafts was only found to contain the non-glycosylated from the $CII_{(256-270)}$-epitope, which correlated well with the preferential tolerance towards this peptide in the T cell response to TSC recipients.

These results indicate that T cells, specific for other, glycosylated, variants of the $CII_{(256-270)}$ epitope, are responsible for disease induction in TSC recipients. If T cells specific for the non-glycosylated epitope participate in disease, CII tolerance induction can be of different levels since grafts were not affected by arthritis onset.

Materials and Methods

C3H.Q mice (H-2q) were originally a obtained from Dr. Shreffler, St. Louis, USA. The transgenic mouse, TSC (T cell epitope in Systemic Collagen), was described earlier (Malmstrom et al., *PNAS* 93(9):4480–4485 (1996)). Briefly, TSC mice express the $CII_{(256-270)}$ rat sequence on type I collagen and thereby systemic expression of the immunodominant rat CII T cell epitope. The transgene was bred as a heterozygote on C3H.Q background.

Rat CII was prepared from the SWARM chondrosarcoma by pepsin digestion or from lathyritic chondrosarcoma and further purified as described earlier [Andersson and Holmdahl, *Eur. J. Immunol.*, 20(5):1061–1066 (1990)). The peptides were synthesized. The glycosylated $CII_{(256-270)}$ peptide had a b-D-galactopyranose residue on L-hydroxylysine at position 264. Both collagen and collagen peptides were dissolved and stored in 0.1 M acetic acid. Crude preparation of type I collagen from skin grafts was performed by pepsin digestion followed by pepsin inactivation but with no further purification.

For arthritis experiments, mice were immunized intradermally in the tail base with 100 μg rat CII emulsified 1:1 in complete Freund's adjuvant (CFA; Difco, Detroit). They were also boosted with 50 μg rat CII emulsified 1:1 in incomplete Freund's adjuvant (IFA; Difco) 5 weeks later. For long-term arthritis experiments, mice were also given a second boost injection as above about 10 weeks after the first immunization. For in vitro experiments, mice were immunized in the hind footpads with each 50 μg of rat CII in CFA.

Four weeks prior to immunization, mice were engrafted with (3–4 cm²) skin from either TSC transgenic mice or littermate controls onto the back of non-transgenic recipients. The grafts were covered with gauze that was removed one week later. In some experiments, recipient mice were also thymectomized two weeks prior to skin transplantation. Thymectomy and skin grafting was performed under anesthesia from chloral hydrate and barbiturate. Graft survival was followed visually during the experiment. At the end of experiment, grafts were removed and used for transgenic CII preparation, as described above, to ensure graft acceptance.

Development of clinical arthritis was followed through visual scoring of the mice starting two weeks after immunization and continuing until the end of the experiment. The arthritis was scored using a scale for 1–3, where 1 means one affected joint, 2 means two or more arthritic joints, and 3 means a severe arthritis involving the entire paw. Alternatively, arthritis was scored using an extended scoring protocol ranging from 1–15 for each paw with a maximum score of 60 per mouse. Each arthritic toe and knuckle was scored as 1, with a maximum of 10 per paw. An arthritic ankle or midpaw was given a score of 5. For example, ankle+midpaw+(1–5) toes were given a score of 11–15.

For arthritis experiments, blood samples were taken at the time of boost immunization(s) as well as at the termination of experiment for analyzes of CII antibody response. The amounts of total anti CII IgG as well as the IgG2a isotypes were determined through quantitative ELSA.

To assay T cell effector functions, the draining popliteal lymph nodes were taken 10 days post immunization. The lymph node cells (LNC) were used for (a) a proliferation assay, where $10^6$ cells were put in triplicate cultures in microtiter wells together with antigen and incubated for 72 hours before thymidine-labeling and harvesting 15–18 hours later; and (b) IFN-γ-ELISA, where supernatant from the proliferation plates was removed prior to harvesting and used in an ELISA to quantitate the amount of IFN-γ produced. In all experiments, the LNC were assayed from individual mice and statistics calculated from the biological variation.

T cell hybridomas HCQ.4 and HCQ.10, specific for $CII_{(256-270)}$ without posttranslational modification and with glucose on hydroxylysin at position K264 respectively, were used to detect transgenic type I collagen prepared from TSC or recipients grafts at the end of arthritis experiments as described earlier (Michaelsson et al., *J. Exp. Med.*, 180: 745–749 (1994) and Corthay et al., *Eur. J. Immunol.*, 28:2580–2590 (1998)). Briefly, syngeneic spleen cells were incubated with titrated amount of antigen at $5\times10^5$/mL together with the hybridoma cells at $5\times10^4$/mL. The interleukin-2 production was detected after 24 hours by transferring 100 μL of the supernatant to new plates. Plates were snap-frozen to avoid any contamination of living cells before addition of $10^4$ CTLL/well. CTLL were incubated for 24 hours before thymidine-labeling and harvesting 15–18 hours later.

Incidence of arthritis was analyzed by the chi-squared test or Fisher's Exact Test, while antibody levels, proliferative responses, and arthritis severity were analyzed by the Mann-Whitney U test.

Induction of Thymic Independent Tolerance by Transplantation

Figure 14:
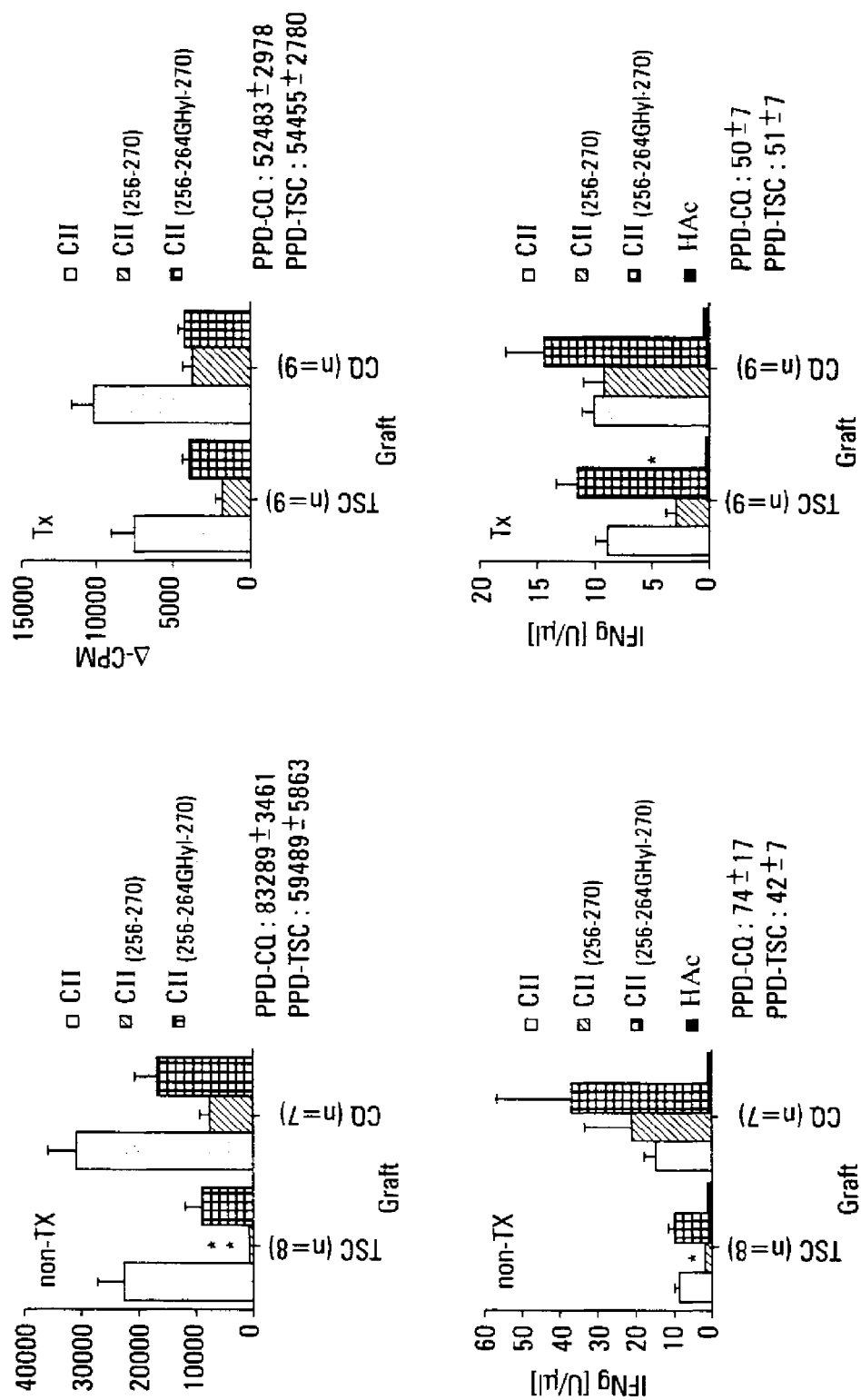
FIG. 14 is a series of bar graphs demonstrating recall responses in vitro towards CII antigens in skin transplanted mice after CII immunization. The indicated number of mice were either grafted with skin from transgenic mice (TSC) or from control littermates (CQ) four weeks before immunization with CII in adjuvant. Ten days later, draining lymph-node cells were restimulated with different antigens (50 mg/mL) for four days, and the proliferation was measured. After in vitro restimulation, supernatants were collected for determination of IFN-γ content. Some mice were also thymectomized (Tx) two weeks before transplantation (b). Cell proliferation is presented as ΔCPM (proliferation with antigen-proliferation without antigen)* $p \leq 0.05$, ** $p \leq 0.01$.

Skin grafts from TSC were accepted when transplanted to wild type recipients. The TSC mouse expressed the immunodominant T cell epitope found in heterologous CII in the skin. Immunization of TSC-graft recipients with rat CII in adjuvant did not induce graft rejection. Thus, the immune response in graft recipients after antigen challenge with CII was investigated to see how the transgenic epitope was recognized in these mice. After immunization of grafter mice with CII, lymphnode cells were rechallanged in vitro with intact CII as well as with two forms of the $CII_{(256-270)}$ epitope, with or without galactosylation (FIG. 14). Proliferation as well as IFN-γ production was reduced against the non-glycosylated version of $CII_{(256-270)}$ (FIG. 14, panels a and c), whereas the response towards the glycosylated form or intact CII did not show of any significant difference. Mice were also thymectomized, prior to transplantation, to investigate if the tolerance described above was dependent or if CII instead can be presented in the periphery in a way that induce tolerance of specific T cells. Indeed, thymectomy of graft recipients did not alter the results as compared to non-thymectomized recipients as specific tolerance towards the non-glycosylated $CII_{(256-270)}$ was found (FIG. 14, panels b and d).

Protection from Arthritis Induced by Skin Transplantation

Graft recipients were immunized for arthritis to see if the specific tolerance observed in vitro towards the $CII_{(256-270)}$ epitope would protect the mice from arthritis. In a first set of experiments, mice were either grafted with skin from TSC or control littermates before immunized with CII and arthritis development was followed for around 10 week. As can be seen in FIG. 15 (experiment a and b), TSC grafted recipients were clearly protected from arthritis with an incidence of around 30% compared to 90% for control mice. This protection was very similar to what was earlier observed for MMC transgenic mice that express the same T cell epitope as TSC. In MMC mice, however, the transgenic expression is limited to joint cartilage. In these skin transplantation experiments, a slight increase of arthritis was noted for TSC recipients at the end of the experiment. It was therefore interesting to see if the protection seen in TSC recipients was stable. Accordingly, the experiment was repeated giving the mice a second boost injection of CII at around 10 weeks after the first immunization and following the mice for an additional 9 weeks. Also, to investigate if the increase of disease at around 10 weeks after immunization was due to newly thymic emigrant that had not yet acquired tolerance towards the $CII_{(256-270)}$ epitope, the mice were thymectomized prior to transplantation and disease induction. As showed in FIG. 15 (experiment c and d) as well as FIG. 16, disease picture during the first 10 weeks was quite similar to the results obtained from the earlier experiments. After a second boost immunization, however, TCS recipients developed arthritis reaching a disease incidence that was comparable to control mice. Disease severity of affected animals, at the end of experiments, was however lower for TSC recipients. This was especially true for non-thymectomized mice (FIG. 15; experiment c and d). As control, naïve TSC transgenic mice were also investigated for arthritis development. As expected, TSC mice did not develop arthritis.

Reduced Anti-CII Antibody Response in TSC Skin Recipients

The IgG response against CII was determined at different time points after immunization and the results are summarized in FIG. 17. There was some variability in specific anti-CII antibody levels between the different experiments. This was not surprising since experiments were performed at three different animal facilities. Throughout all experiments, however, and irrespective of thymectomy, TSC recipients had reduced levels of IgG response compared to controls during the first 10 weeks after immunization. This was due to a significant reduction of the anti-CII IgG2a isotype whereas the IgGI isotype was relatively low and did not differ compared to control mice. Thymectomized TSC recipients also had lower levels of anti-CII antibodies at 19 weeks post immunization although the arthritis index did not differ at this point. In the long-term experiment with non-thymectomized mice, however, the antibody levels did not differ significantly even though the protection against arthritis was more pronounced than for thymectomized TSC recipients. Lastly, control immunized TSC mice also had significant anti-CII IgG antibody titers that were quite comparable to those of TSC-skin grafted recipients at 5 weeks post immunization. At later time points, however, antibody levels were reduced while being similar or elevated for TSC-grafted mice.

Epitope-Specific Tolerance Correlates with Transgenic Expression

Figure 18:
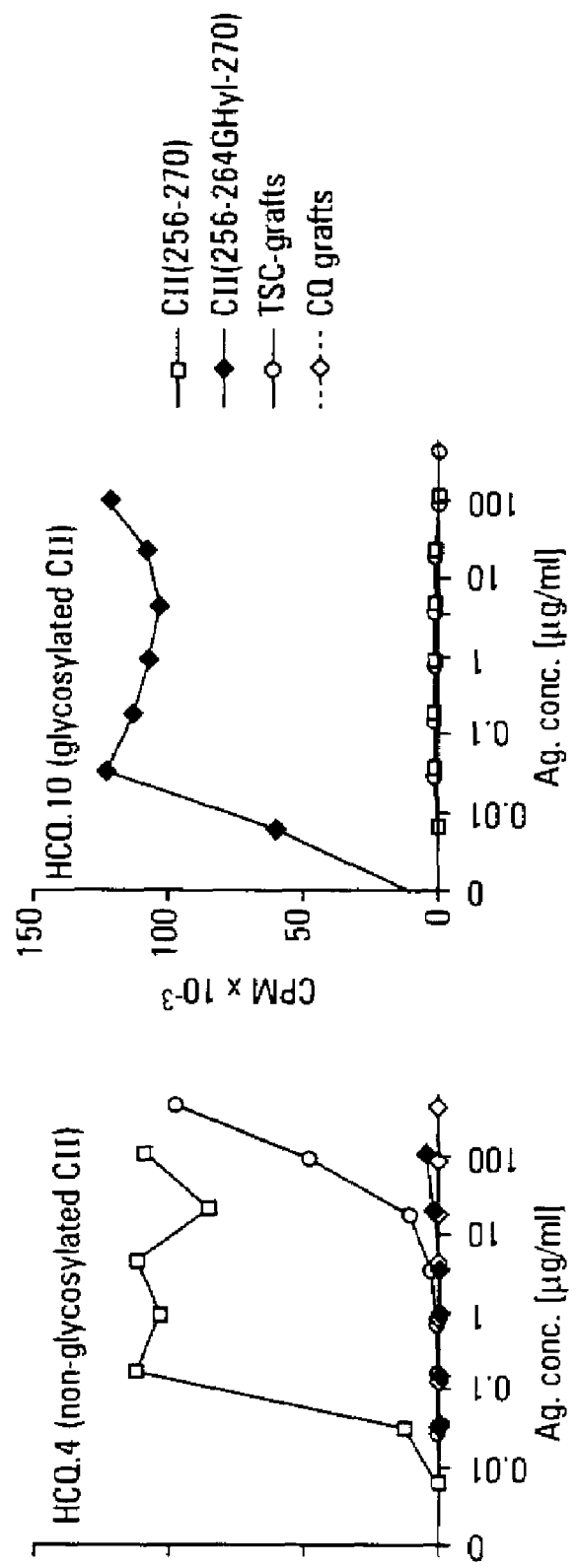
FIG. 18 is two graphs reporting the detection of transgenic CII from skin grafts. Hybridomas HCQ.4 and HCQ.10, specific for non-glycosylated and glycosylated $CII_{(256-270)}$ respectively, were tested for recognition of transgenic CII from skin grafts removed from non-thymectomized recipient mice 19 weeks after immunization by a CTLL assay. Glycosylated ($CII_{(256-264GHyl-270)}$) or non-glycosylated ($CII_{(256-270)}$) polypeptides were used as positive and negative controls. Both hybridomas respond to whole CII protein. The same results were also found from preparations made from grafts from thymectomized animals.

Since most of the TSC recipients eventually developed arthritis, experiments were performed to ensure that it was not a consequent of late time graft refection or by elimination of transgenic expression in TSC grafts. Thus, at the end of the long-term experiments, grafts were removed and used to make crude preparation of collagen. Collagen from TSC grafts were able to stimulate the HCQ.4 hybridoma (specific for the non-glycosylated $CII_{(256-270)}$ sequence) providing that the grafts had not been rejected (FIG. 18). Interestingly, the TCS-graft collagen was not recognized by the HCQ.10 hybridoma (specific for the glycosylated $CII_{(256-270)}$ variant). Collagen from 7 weeks old TSC transgenic mice used as TSC skin donors as well as from 26 week old TSC mice were also prepared and tested for specific $CII_{(256-270)}$ recognition by the hybridomas. HCQ.4, but not HCQ.10 hybridomas, responded to these preparations, indicating that the glycosylated form of $CII_{(256-270)}$ was not present in TSC skin in adult mice and therefore not on the grafts used for tolerance induction in wild type mice. This also correlates with the in vitro experiments showing a unique tolerance towards the non-glycosylated CII epitope (FIG. 14). Since it was earlier reported that TSC skin express the glycosylated CII epitope, collagen was prepared from newborn TSC mice. Preparations made from newborn TSC mice were able to stimulate both the HCQ.4 as well as HCQ.10 hybridoma, indicating that the glycosylation level of transgenic collagen is age dependent in these mice.

By comparing the in vitro data with the arthritis experiments, it is concluded that T cells specific for non-glycosylated $CII_{(256-270)}$ become tolerized in the periphery and that this protects the animals from arthritis development. The protection is only partial in the sense that it is not indefinite. It is also concluded that newly thymic emigrants are not responsible for the disease development observed at late stages after challenge with CII. Instead, disease development in TSC recipients seems to be due to tolerized T cells becoming able to mediate arthritis. Alternatively, T cells with other specificities for $CII_{(256-270)}$ (or CII) may be responsible for disease development.

Example 13

Synthesis and characterization of triple helical polypeptide complexes containing a CII T-cell epitope This example describes the synthesis and characterization of triple helical polypeptide complexes containing a T-cell epitope. The complexes are either double-bound, having interpolypeptide linkages in both the C-terminal and N-terminal regions (e.g., THP 2), or are single-bound, having interpolypeptide linkages in C-terminal region (e.g., THP 4).

General Methods and Materials

Dry DMF was obtained by distillation under reduced pressure followed by storage over 3 A molecular sieves. Protected amino acids were purchased from Bachem (Bubendorf, Switzerland), Neosystem (Strasbourg, France) or Fluka (Buchs, Switzerland). O-(7-Aza-benzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU), and diisopropyl ethyl amine were obtained from Perseptive Biosystems. The Kemp's triacid triglycine conjugate $[KTA(Gly-OH)_3]$ was synthesized as described in Feng, Y., et al. (1996) *J. Am. Chem. Soc.* 118:10351–10358. Yields were not corrected for peptide content (typical value: 70–85%). Gel phase $^{19}F$ NMR spectra were recorded on a Bruker DRX400 spectrometer at 375 MHz in DMSO-$d_6$. Chemical shifts were referenced to $CFCl_3$ at 0 ppm. Preparative reversed phase HPLC was performed on a Kromasil C-8 column (25×20 mm, 5 μm, 100 A) with a linear gradient of MeCN (0 to 100% over 60 minutes) in $H_2O$, both containing 0.1% trifluoroacetic acid. A flow rate of 11 mL/min was used and detection was at 214 nm. Analytical reversed phase HPLC was performed on a Kromasil C-8 column (25×4.6 mm, 5 μm, 100 Å) with the same eluents. A flowrate of 1.5 mL/min was used and detection was at 214 nm.

Synthesis of Fmoc-Ahx-Lys(Fmoc-Ahx)-Lys(Fmoc-Ahx)-4F-Phe-Tyr(tBu)-Gly-PHB-Tentagel™-R (1, Scheme 1)

Figure 21:
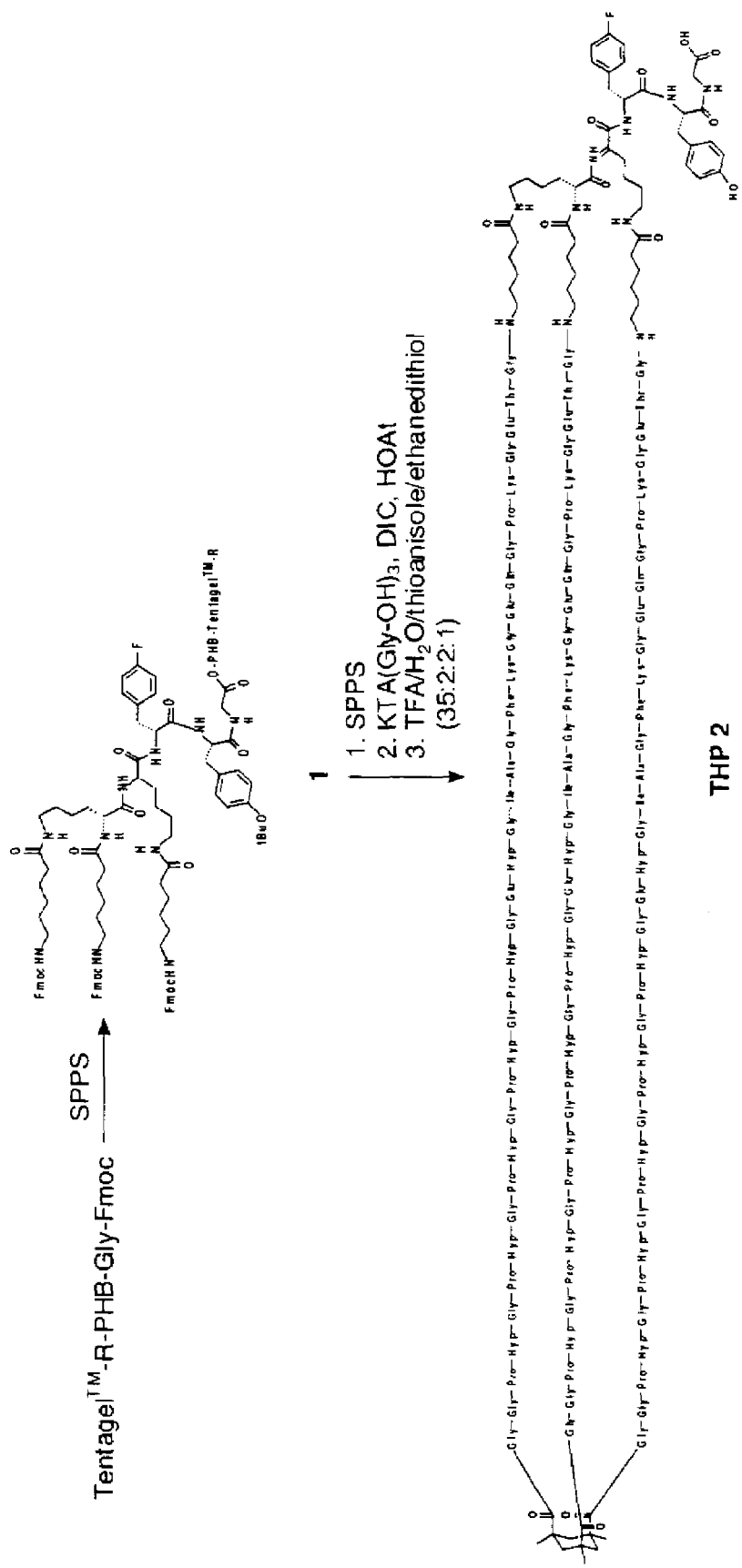
FIG. 21 is a scheme depicting the synthesis of a polypeptide complex having interpolypeptide linkages in the C-terminal and N-terminal regions.

The following description refers to FIG. 21 and the synthesis of KTA-[Gly-(Gly-Pro-Hyp)$_5$-Gly-$CII_{(257-258Hyp-}$ $_{273T-274})]_3$-L(F)$_{Ahx}$. Resin 1 was synthesized in a manually agitated reactor on Tentagel™-R-PHB-Gly-Fmoc resin (492 mg, 0.10 mmol). Peptide couplings were performed in freshly distilled DMF with amino acids (4 eq.) activated as 1-hydroxybenzotriazole esters using diisopropyl carbodiimide (DIC, 3.9 eq) and 1-hydroxybenzotriazole (6 eq.), unless stated otherwise. The reactions were monitored by observing the color change of bromophenol blue (BFB, 0.75 meq) during the reaction, as described in Flegel, M. and Sheppard, R. C. (1990) *J. Chem. Soc., Chem. Commun.* Fmoc protective groups were removed by a slow flow of 20% piperidine in DMF for 3 minutes followed by 7 minutes of agitation and the resin was washed 6 times with DMF between couplings and deprotections. Fmoc-Tyr(tBu)-OH, Fmoc-4F-Phe-OH, Fmoc-Lys(Alloc)-OH and Fmoc-Lys(Fmoc)-OH were incorporated as described above and the resin was then washed 6 times with DMF and 10 times with $CH_2Cl_2$. Gel phase $^{19}$F NMR showed one single peak at −116.7 ppm originating from the 4F-Phe residue. The resin was filtered and dried at high-vacuum for 2 hours at 40° C., and was then treated with a solution of$(PPh_3)_4Pd(0)$ in $CHCl_3$/N-methylmorpholine/acetic acid (37:2:1, 7 mL) for 2 hours at room temperature under nitrogen with protection from light under gentle agitation. The resin was washed with 0.5% v/v diisopropylethylamine (DIPEA, 20 mL) in DMF and 0.5% w/v sodium diethyldithiocarbamate (100 mL) in DMF followed by DMF (6×5 mL). Gel phase $^{19}$F NMR spectroscopy showed complete conversion (one single peak at −116.8 ppm). The resin was washed with DMF, 0.5% HOBt in DMF (50 mL) and DMF (3×). The Fmoc protective groups on the α- and ε-amino groups of the N-terminal Lys were removed by treatment with 20% piperidine in DMF (3 minutes slow flow +7 minutes agitation). The resin was washed 6 times with DMF and Fmoc-Ahx (1.2 mmol, 4 eq./resin-bound amino group) was coupled as described above. Gel phase $^{19}$F NMR spectroscopy showed one major (−116.7 ppm, >95%) and one minor (−116.2 ppm) peak. The resin was washed with DMF (6×) and $CH_2Cl_2$ (10×) and dried overnight under high vacuum giving 515 mg of dry resin.

A small amount of resin 1 (53 mg) was allowed to swell in DMF, the Fmoc protective groups were removed (as above) and the resin was washed 6 times with DMF and 10 times with $CH_2Cl_2$ and then dried under high-vacuum for 1.5 hours. The resin was then treated with TFA/$H_2O$/thioanisole/ethanedithiol (4 mL, 35:2:2:1) for 4 hours at room temperature. The resin was filtered off and washed with acetic acid (10 mL) and the combined filtrates were concentrated and then co-concentrated with glacial acetic acid to dryness. The solid residue was triturated with diethyl ether, dissolved in 50% aqueous acetic acid, diluted with water (5 mL) and freeze-dried. Analytical reversed phase HPLC verified the homogeneity of the crude product. HRMS (FAB) of the main compound obtained by preparative reversed phase HPLC: calcd for $C_{50}H_{80}FN_{10}O_{10}$ (M+H$^+$) 999.6043, found 999.6018.

Residues corresponding to the $CII_{(257-258Hyp-273T-274)}$ T cell epitope (Glu-Hyp-Gly-Ile-Ala-Gly-Phe-Lys-Gly-Glu-Gln-Gly-Pro-Lys-Gly-Glu-Thr-Gly; SEQ ID NO:57) were attached to 1 (462 mg, 90 µmol based on resin capacity or 270 µmol amino groups) using a Perceptive Biosystems Pioneer™ peptide synthesizer. Fmoc amino acids with standard side chain protective groups (4 eq.) were activated using HATU (4 eq.) and DIPEA (8 eq.), were coupled for 3 hours. Removal of Fmoc groups was performed using 20% piperidine in DMF. After completion of incorporation of the $CII_{(257-274)}$ epitope (the Fmoc group of Glu257 was not removed) the resin was washed 10 times with $CH_2Cl_2$ and dried under high-vacuum for 4 hours giving 891 mg of peptide-resin. 198 mg of the resin (corresponding to 20 µmol based on resin capacity or 60 µmol amino groups) was transferred to a manually agitated reactor, treated with 20% piperidine in DMF (3 minutes slow flow followed by 7 minutes of agitation), and washed 6 times with DMF. Fmoc-Pro-Hyp(tBu)-Gly-OH was coupled (51 mg, 90 µmol, 1.5 eq.) using DIC (14 µL, 90 µmol, 1.5 eq.) and 1-hydroxy-7-aza-benzotriazole (HOAt, 18 mg, 140 µmol, 2.25 eq.). The reaction was monitored by BFB (0.75 meq.) and was washed 6 times with DMF when the reaction was complete. Four additional Fmoc-Pro-Hyp(tBu)-Gly units were coupled under the same conditions. After Fmoc removal (as described above), Fmoc-Gly-OH (71 mg, 4 eq.) was coupled using DIC (37 µL, 3.9 eq.) and HOBt (55 mg, 6.0 eq.) with monitoring by BFB. The Fmoc group was removed (as described above) and the resin was washed 6 times with DMF and 10 times with $CH_2Cl_2$, and then was dried under high-vacuum for 2.5 hours. The resin was allowed to swell in dry DMF (2 mL), and activated KTA(Gly-OH)$_3$ (6.8 mg, 16 µmol) was added in 4 portions over a period of 43 hours with agitation. Each portion of KTA(Gly-OH)$_3$ was activated for 15 minutes prior to addition using DIC (1.8 µL, 11.5 µmol, 0.95 eq./COOH) and HOAt (18 µmol, 1.5 eq./COOH). After completion, the resin was washed twice with dry DMF and suspended in dry DMF (ca. 2 mL). HOAt (18 µmol) and then DIC (11.5 µmol) were added, and the resin was agitated for 1 hour. The resin was then washed twice with dry DMF, suspended in dry DMF (2 mL), agitated for an additional 3.5 hours and washed three times with dry DMF. pF-benzoic acid (33 mg, 0.24 mmol) was activated for 10 minutes with DIC (37 µL) and HOBt (49 mg, 0.36 mmol) in dry DMF, and then was added to the resin together with BFB (23 µL of a 2 mM solution in DMF). After agitating for 18 hours, the resin was washed 6 times with DMF and 10 times with $CH_2Cl_2$, and was dried under high-vacuum overnight. The resin was treated with TFA/$H_2O$/thioanisole/ethane dithiol (35:2:2:1, 8 mL) for 3.5 hours at room temperature. The resin was filtered off and washed with HOAc (2×2 mL) and the combined filtrates were concentrated and coconcentrated from acetic acid until dryness. The solid was triturated with diethyl ether (ca 2 mL), dissolved in 50% aqueous acetic acid (1 mL), diluted with water (6 mL) and freeze-dried. Preparative reversed phase HPLC of the residue gave 2 (8.9 mg, 4.1% yield).

THP 2 can be represented as follows: KTA-[Gly-(Gly-Pro-Hyp)$_5$-Gly-CII$_{(257-258Hyp-273T-274)}$]$_3$-L(F)$_{Ahx}$. The sequence of the polypeptide chain between the L(F)$_{Ahx}$ group and the KTA group is: Gly-Gly-Pro-Hyp-Gly-Pro-Hyp-Gly-Pro-Hyp-Gly-Pro-Hyp-Gly-Pro-Hyp-Gly-Glu-Hyp-Gly-Ile-Ala-Gly-Phe-Lys-Gly-Glu-Gln-Gly-Pro-Lys-Gly-Glu-Thr-Gly (SEQ ID NO:58).

Synthesis of triple helical polypeptide complexes having interpolypeptide linkages in the C-terminal region (THP 4, Scheme 2)

Figure 22:
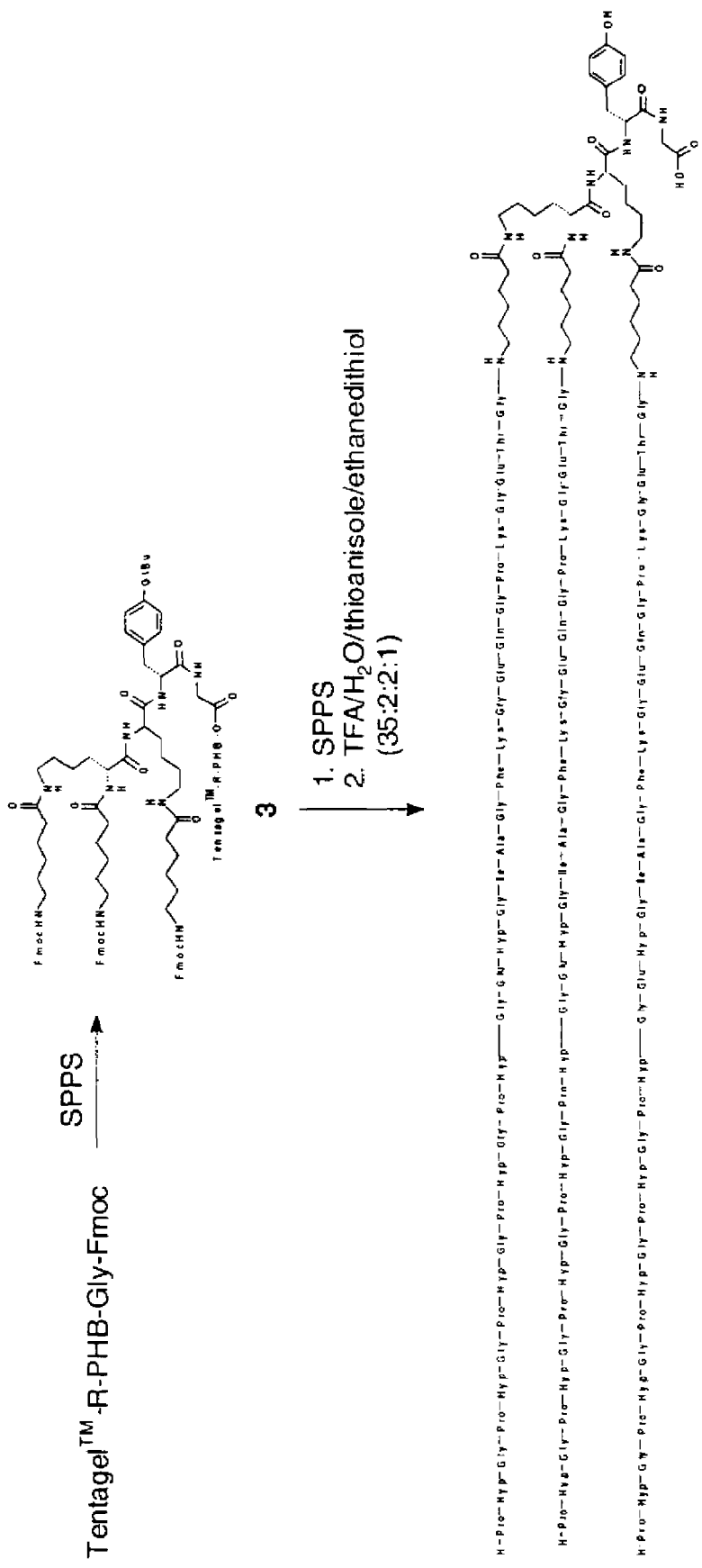
FIG. 22 is a scheme depicting the synthesis of a polypeptide complex having interpolypeptide linkages in the C-terminal region.

The following description refers to FIG. 22 and the synthesis of [(Pro-Hyp-Gly)$_5$-CII$_{(257-258Hyp-273T-274)}$]$_3$-L$_{Ahx}$. Synthesis was performed essentially as described for THP 2 from branching structure 3, which is similar to 1 but lacks the 4F-Phe moiety. Branch 3 was synthesized essentially as described for 1 but with an Fmoc-Lys(Alloc)-OH instead of the Fmoc-Lys(Fmoc)-OH. Coupling of CII residues 257–274 was performed using 5 equivalents of Fmoc-amino acids activated by HBTU (5 eq) and DIPEA (5 eq). Fmoc-Pro-Hyp(tBu)-Gly-OH units were coupled in 2-fold excess using DIC and HOAt. The 5th Pro-Hyp-Gly unit was coupled as individual Fmoc-amino acids in 4 equivalents excess using DIC (3.9 eq.) and HOBt (6 eq.) with monitoring by BFB. Cleavage of 88 mg resin (corresponding to 10 µmol) from the solid phase (as for THP 2) and purification by preparative reversed phase HPLC gave THP 4 (5.2 mg, 0.52 µmol, 5.2% yield): ES-MS: calcd m/z 10107 found 10110.

THP 4 can be represented as follows: [(Pro-Hyp-Gly)$_5$-CII$_{(257\text{-}258Hyp\text{-}273T\text{-}274)}$]$_3$-L$_{Ahx}$. The sequence of the polypeptide chain up to the L$_{Ahx}$ group is: Pro-Hyp-Gly-Pro-Hyp-Gly-Pro-Hyp-Gly-Pro-Hyp-Gly-Pro-Hyp-Gly-Glu-Hyp-Gly-Ile-Ala-Gly-Phe-Lys-Gly-Glu-Gln-Gly-Pro-Lys-Gly-Glu-Thr-Gly (SEQ ID NO:59).

CD Spectroscopy

Figure 23:
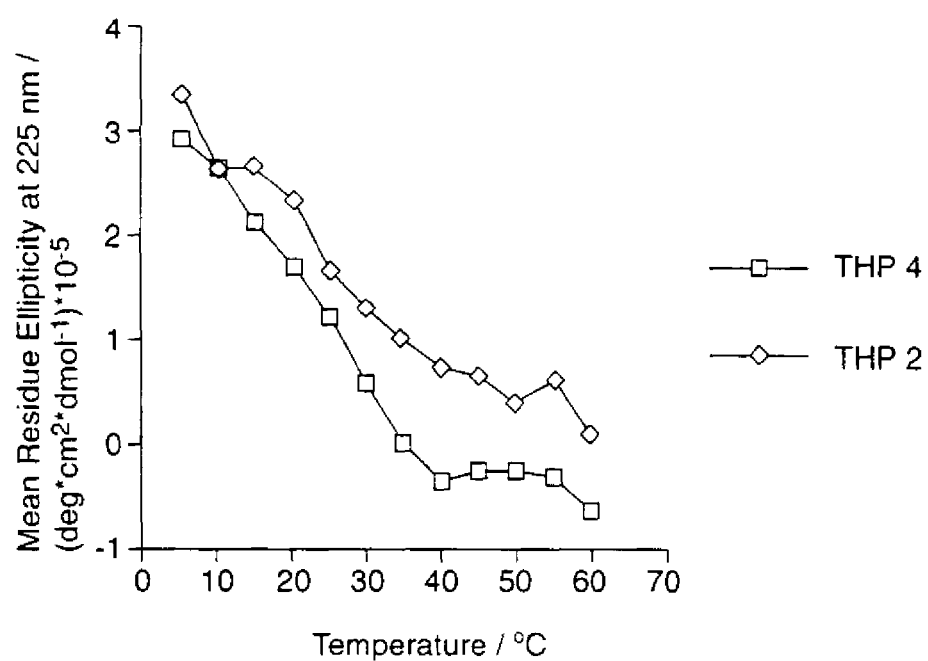
FIG. 23 is a graph plotting mean residue elipticity at 225 nm as a function of temperature for THP 2 and THP 4.

Circular dichroism (CD) spectra for THP 2 and THP 4 were recorded on a JASCO J750 spectropolarimeter as 0.1 mg/mL solutions in 20 mM phosphate buffer at pH 7.0±0.1 with an optical path length of 1 mm. Samples were stored at 5° C. for at least 24 hours prior to measurement. Spectra were recorded from 185–250 nm at a scan speed of 0.5 nm/s averaging 2 or 4 scans for each spectra. The temperature was increased in steps of 5° C. and the samples were allowed to equilibrate until the measurements were time-independent. The mean residue elipticity at 225 nm as a function of temperature for THP 2 and THP 4 is shown in FIG. 23.

Immunization of Mice with THP 2

Five C57/BL6×DBA1/J F1 mice (QD), 12 weeks of age were immunized with 20 micrograms of THP 2 in 100 µL 1:1 PBS:complete Freund's adjuvant. After 16 days, the mice were bled in the tail vein.

Three triple helical polypeptide complexes were analyzed by ELISA. The first contained a T-cell epitope and can be represented as follows: [(Gly-Pro-Hyp)$_5$-CII$_{(259\text{-}273T)}$-(Gly-Pro-HYP)$_2$]$_3$-L$_{Ahx}$. The second contained a B-cell epitope and can be represented as follows: [(Gly-Pro-Hyp)$_5$-CII$_{(358\text{-}366Hyp)}$-(Gly-Pro-Hyp)$_2$]$_3$-L$_{Ahx}$. The third contained both a T-cell and a B-cell epitope and can be represented as follows: [(Gly-Pro-Hyp)$_5$-CII$_{(259\text{-}273T)}$-(Gly-Pro-Hyp)$_1$-CII$_{(358\text{-}366Hyp)}$-(Gly-Pro-Hyp)$_2$]$_3$-L$_{Ahx}$. Briefly, wells were coated independently with each of the polypeptide complexes by incubation with 50 µL of 4 µg/mL polypeptide complex solution overnight at 4° C. After an overnight blocking, sera were added from each of the five mice and in 1:100, 1:1000, and 1:10000 dilutions in PBS in duplicates. After addition of a secondary goat anti-mouse IgG (H+L) peroxidase conjugated antibody (Jackson ImmunoResearch, West Grove, Pa., USA), the plates were developed with the ABTS substrate system (Roche Diagnostics, Mannheim, Germany). Intermediate washes involved 7 washes.

Figure 24:
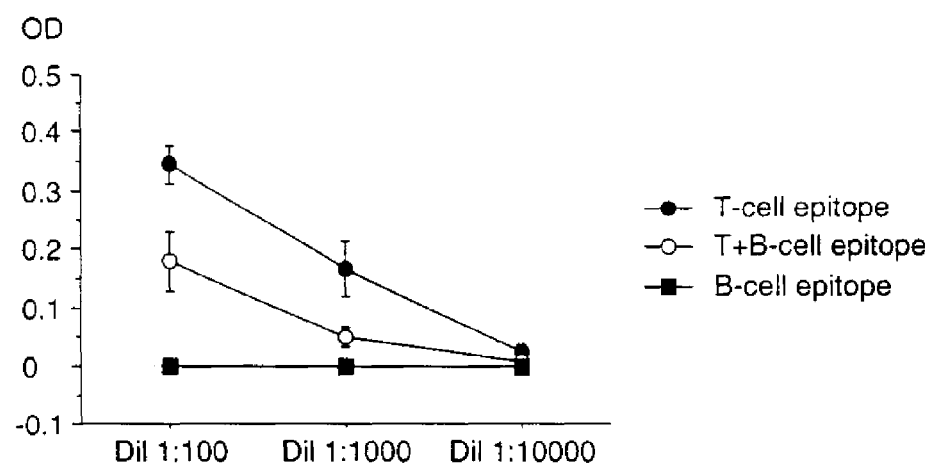
FIG. 24 is a graph plotting optical density against dilutions for [(Gly-Pro-Hyp)$_5$-CII$_{(259-273T)}$-(Gly-Pro-Hyp)$_2$]$_3$-L$_{Ahx}$, [(Gly-Pro-Hyp)$_5$-CII$_{(259-273T)}$-(Gly-Pro-Hyp)$_1$-CII$_{(358-366Hyp)}$-(Gly-Pro-Hyp)$_2$]$_3$-L$_{Ahx}$, and [(Gly-Pro-Hyp)$_5$-CII$_{(358-366Hyp)}$-(Gly-Pro-Hyp)$_2$]$_3$-L$_{Ahx}$ used as antigen in an ELISA assay. Standard deviations between OD values in the individual wells are depicted as bars through the points. In the legend, T-cell epitope refers to [(Gly-Pro-Hyp)$_5$-CII$_{(259-273T)}$-(Gly-Pro-Hyp)$_2$]$_3$-L$_{Ahx}$; B-cell epitope refers to [(Gly-Pro-Hyp)$_5$-CII$_{(358-366Hyp)}$-(Gly-Pro-Hyp)$_2$]$_3$-L$_{Ahx}$; and T+B-cell epitope refers to [(Gly-Pro-Hyp)$_5$-CII$_{(259-273T)}$-(Gly-Pro-Hyp)$_1$-CII$_{(358-366Hyp)}$-(Gly-Pro-Hyp)$_2$]$_3$-L$_{Ahx}$.

The antisera of mice immunized with THP 2 did not react against [(Gly-Pro-Hyp)$_5$-CII$_{(358\text{-}366Hyp)}$-(Gly-Pro-Hyp)$_2$]$_3$-L$_{Ahx}$, the triple helical polypeptide containing the B-cell epitope (FIG. 24). Thus, no immune response was raised against the common parts of the three different triple helical polypeptide complexes. The antisera reacted strongly against [(Gly-Pro-Hyp)$_5$-CII$_{(259\text{-}273T)}$-(Gly-Pro-Hyp)$_2$]$_3$-L$_{Ahx}$, the triple helical polypeptide containing the T-cell epitope (FIG. 24), indicating that THP 2 was immunogenic.

Example 14

Antigen Presentation

Antigen-presentation of polypeptides and triple helical polypeptide complexes was studied using A$^q$-restricted HDQ.9, A$^q$-restricted HRC.2, A$^q$-restricted HCQ.4, and DR4-restricted 1259 T cell hybridomas. Briefly, A$^q$-restricted spleen cells were derived from DBA/1 mice, and DR4-restricted spleen cells were derived from DR4$^+$/_H-2$^-$/_ mice. T cell hybridoma cells (5×10$^4$ cells/well) were incubated with polypeptides and polypeptide complexes (20 µg/mL, dilution 1:5) and 5×10$^5$ spleen cells per well (normal or fixed in 1% paraformaldehyde for 15 min at room temperature) in a volume of 200 µL in 96-well plates for 24 hours. The reactivity of the hybridoma cells toward the polypeptides and triple helical polypeptide complexes, reflected by IL-2 production, was measured by ELISA using europium-labeled streptavidin (WALLAC, Turku).

Figure 25:
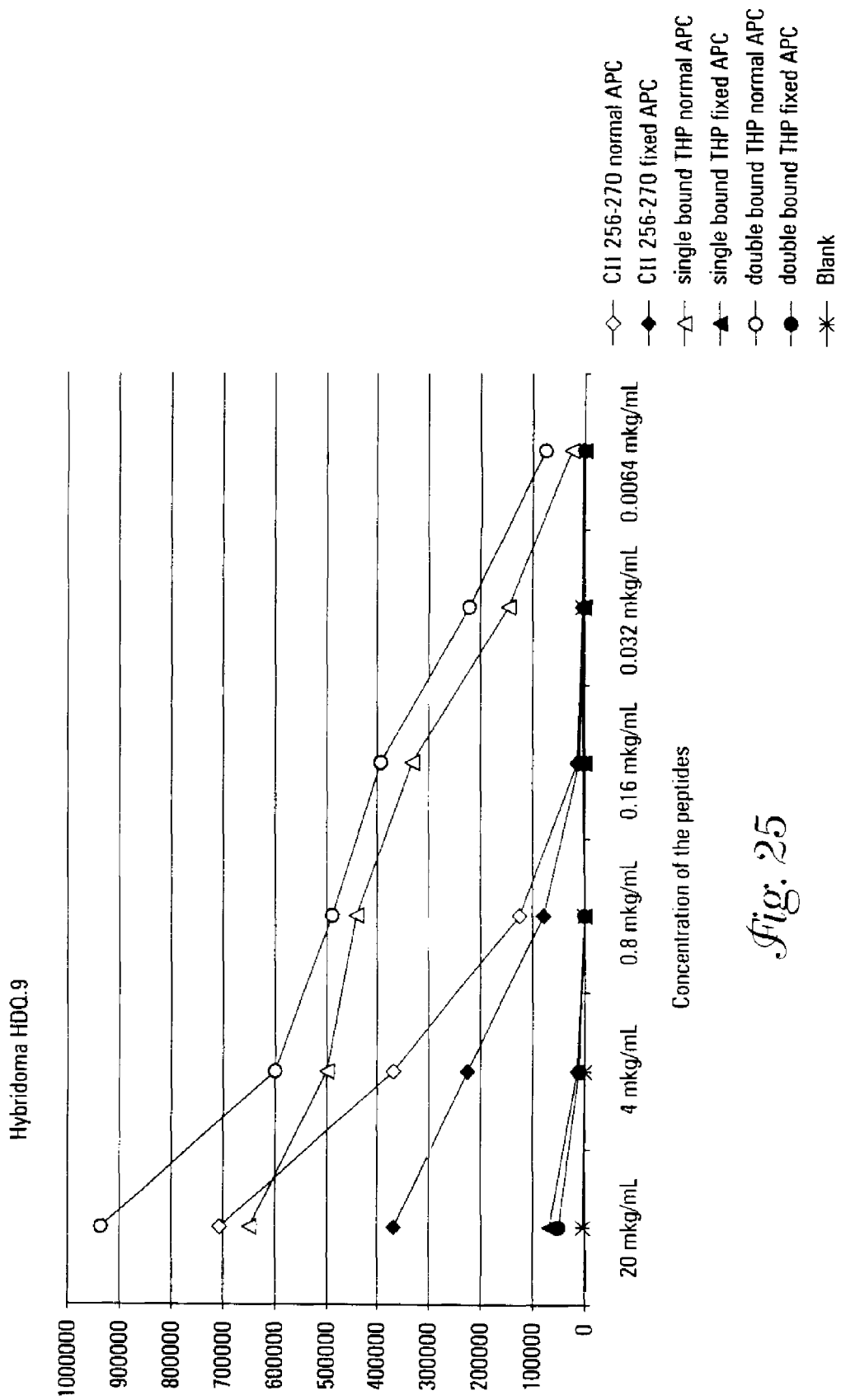
FIG. 25 is a graph plotting IL-2 production as measured by ELISA as a function of polypeptide concentration. $A^q$-restricted HRQ.2 hybridoma cells were incubated with $CII_{(256-270)}$, [(Pro-Hyp-Gly)$_5$-CII$_{(257-258Hyp-273T-274)}$]$_3$-L$_{Ahx}$, and KTA-[Gly-(Gly-Pro-Hyp)$_5$-Gly-CII$_{(257-258Hyp-273T-274)}$]$_3$-L(F)$_{Ahx}$. In the legend, CII 256–270 refers to $CII_{(256-270)}$; single bound THP refers to [(Pro-Hyp-Gly)$_5$-CII$_{(257-258Hyp-273T-274)}$]$_3$-L$_{Ahx}$; double bound THP refers to KTA-[Gly-(Gly-Pro-Hyp)$_5$-Gly-CII$_{(257-258Hyp-273T-274)}$]$_3$-L(F)$_{Ahx}$; and blank refers to media without polypeptide complexes.
Figure 26:
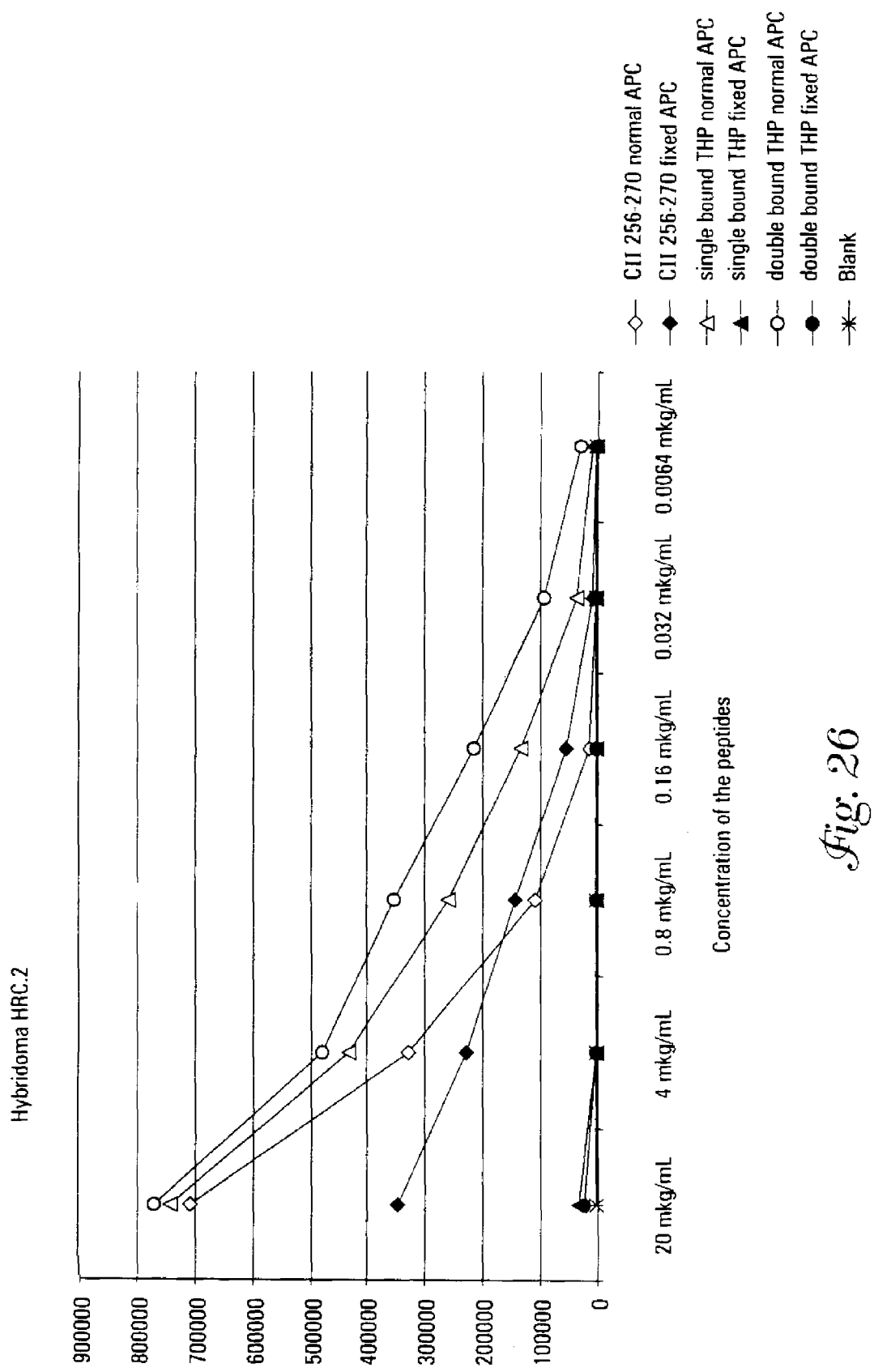
FIG. 26 is a graph plotting IL-2 production as measured by ELISA as a function of polypeptide concentration. $A^q$-restricted HRC.2 hybridoma cells were incubated with $CII_{(256-270)}$, [(Pro-Hyp-Gly)$_5$-CII$_{(257-258Hyp-273T-274)}$]$_3$-L$_{Ahx}$, and KTA-[Gly-(Gly-Pro-Hyp)$_5$-Gly-CII$_{(257-258Hyp-273T-274)}$]$_3$-L(F)$_{Ahx}$. In the legend, CII 256–270 refers to $CII_{(256-270)}$; single bound THP refers to [(Pro-Hyp-Gly)5-CII$_{(257-258Hyp-273T-274)}$]$_3$-L$_{Ahx}$; double bound THP refers to KTA-[Gly-(Gly-Pro-Hyp)$_5$-Gly-CII$_{(257-258Hyp-273T-274)}$]$_3$-L(F)$_{Ahx}$; and blank refers to media without polypeptide complexes.
Figure 27:
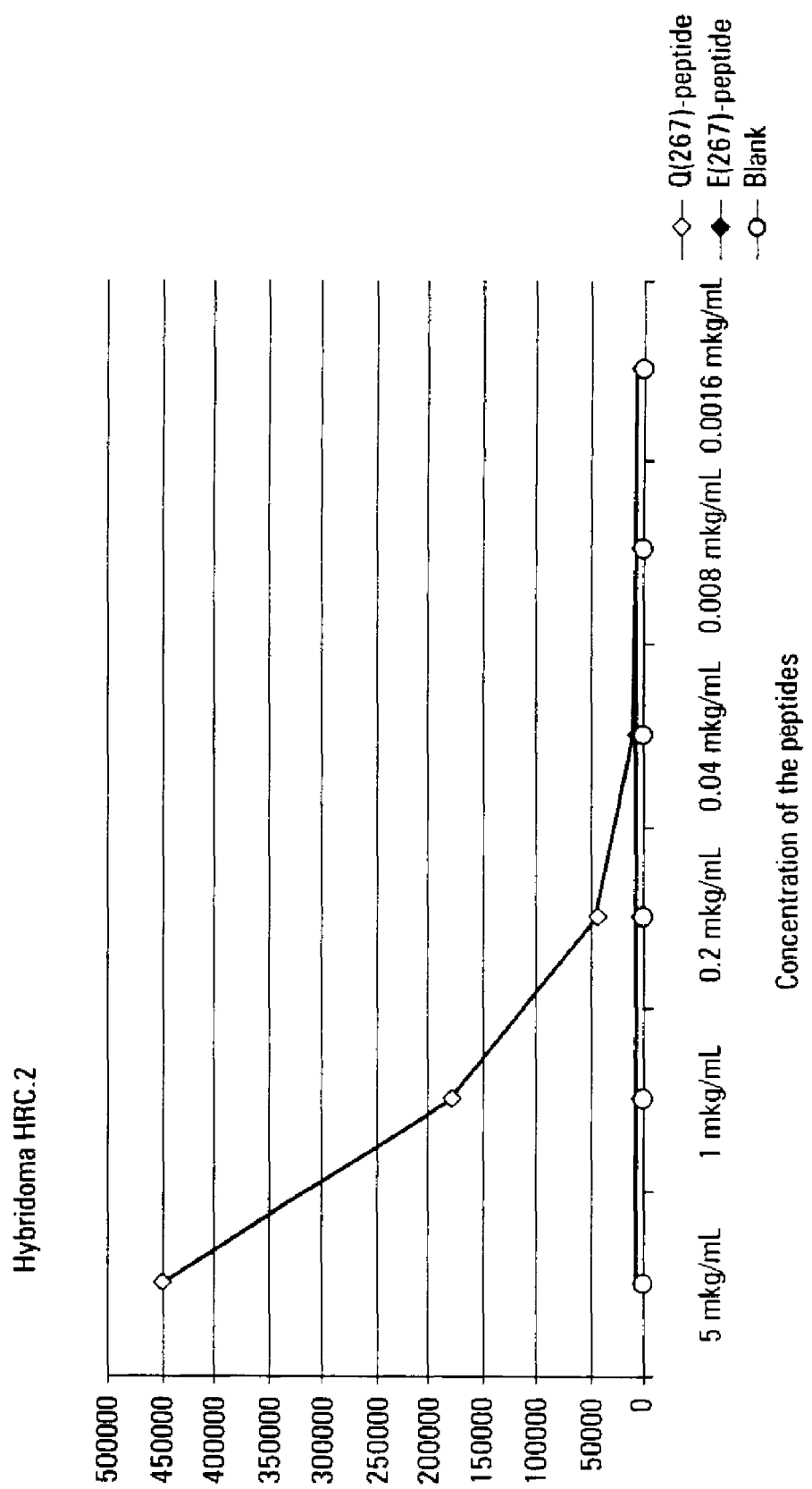
FIG. 27 is a graph plotting IL-2 production as measured by ELISA as a function of polypeptide concentration. $A^q$-restricted HRC.2 hybridoma cells were incubated with $CII_{(259-273Hyp-274)}$ and $CII_{(259-267E-273Hyp-274)}$ polypeptides. In the legend, Q(267)-peptide refers to $CII_{(259-273Hyp-274)}$; E(267)-peptide refers to $CII_{(259-267E-273Hyp-274)}$; and blank refers to media without polypeptide complexes.
Figure 28:
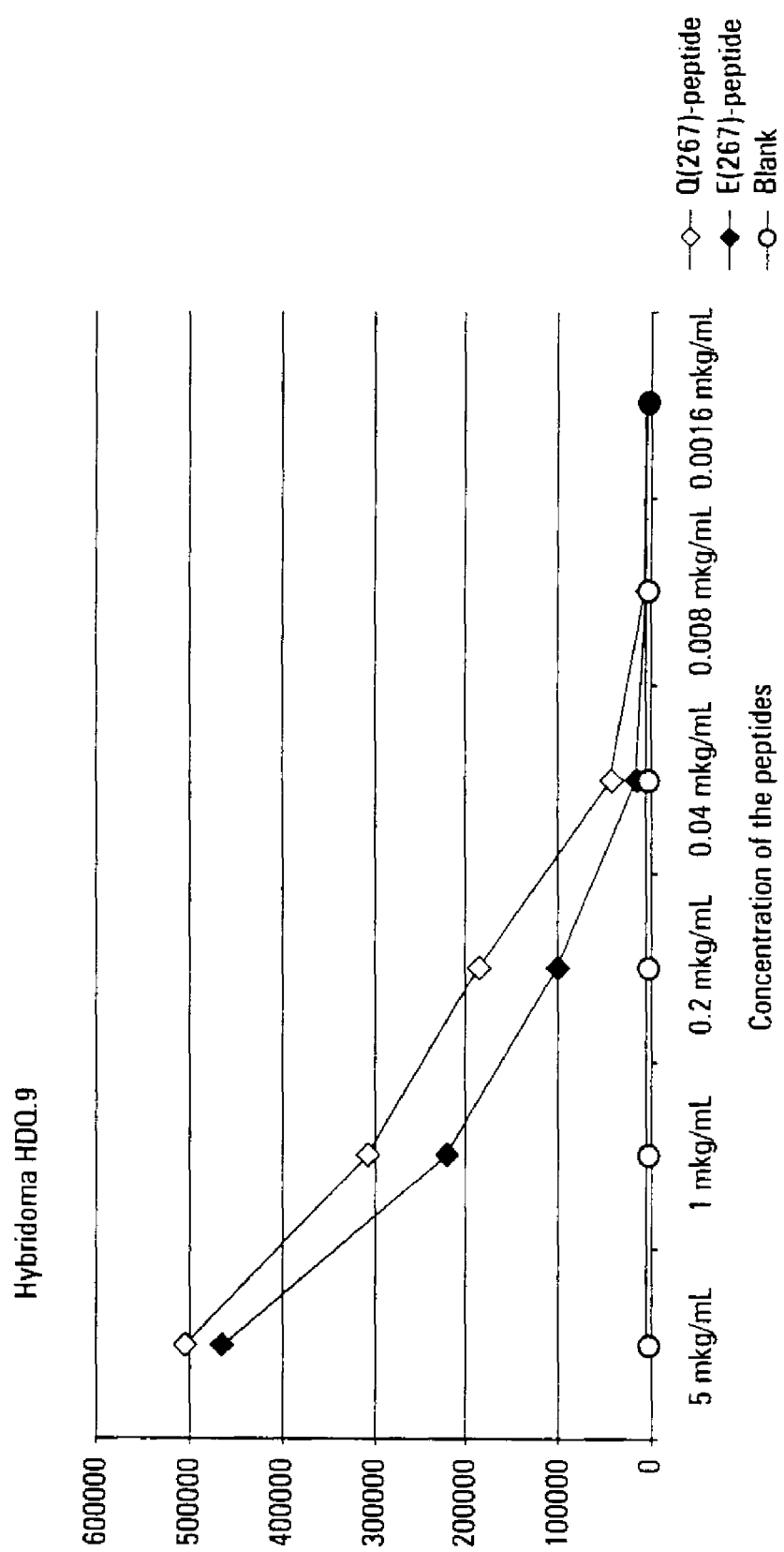
FIG. 28 is a graph plotting IL-2 production as measured by ELISA as a function of polypeptide concentration. $A^q$-restricted HDQ.9 hybridoma cells were incubated with $CII_{(259-273Hyp-274)}$ and $CII_{(259-267E-273Hyp-274)}$ polypeptides. In the legend, Q(267)-peptide refers to $CII_{(259-273Hyp-274)}$; E(267)-peptide refers to $CII_{(259-267E-273Hyp-274)}$; and blank refers to media without polypeptide complexes.
Figure 29:
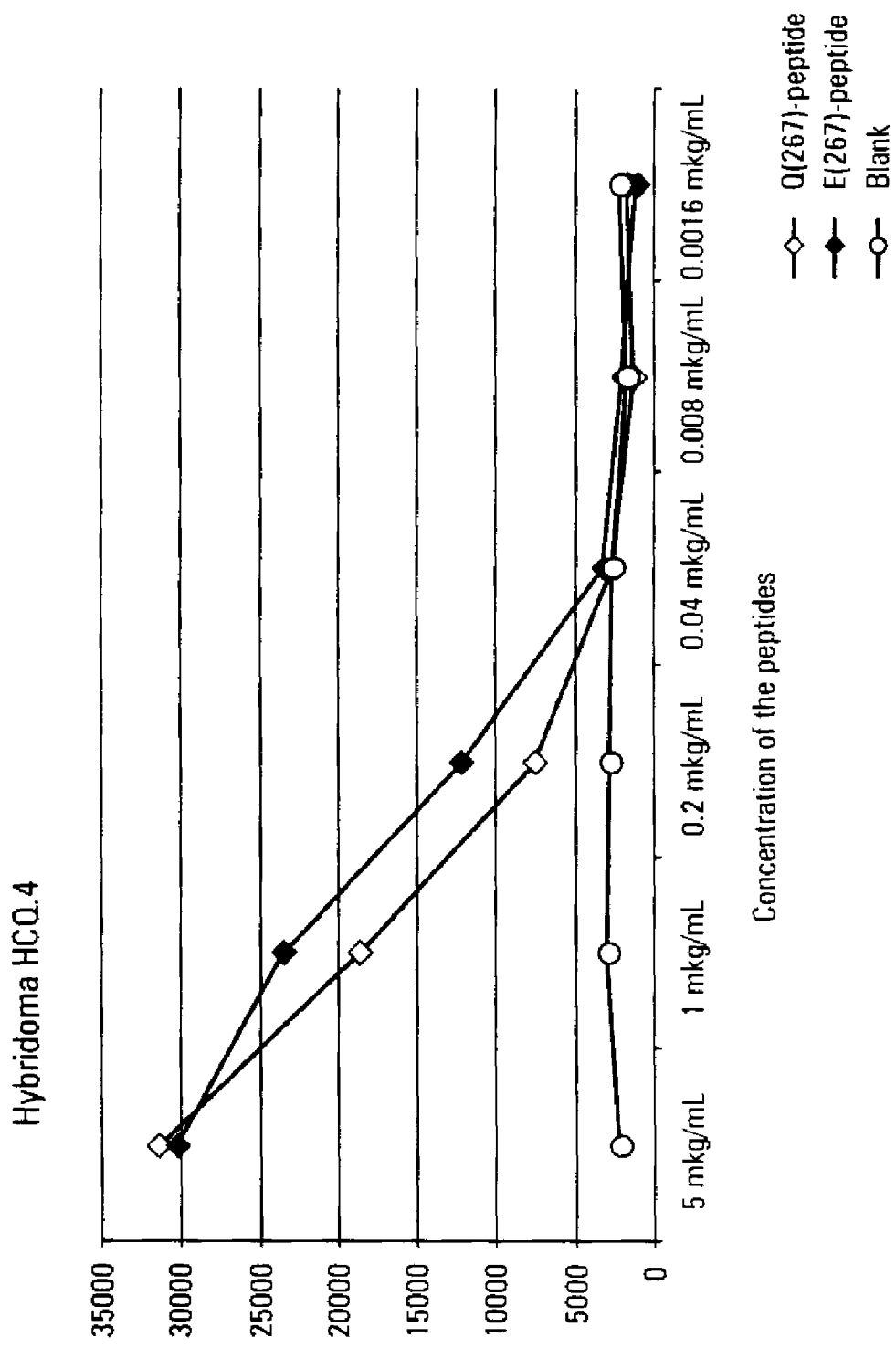
FIG. 29 is a graph plotting IL-2 production as measured by ELISA as a function of polypeptide concentration. $A^q$-restricted HCQ.4 hybridoma cells were incubated with $CII_{(259-273Hyp-274)}$ and $CII_{(259-267E-273Hyp-274)}$ polypeptides. In the legend, Q(267)-peptide refers to $CII_{(259-273Hyp-274)}$; E(267)-peptide refers to $CII_{(259-267E-273Hyp-274)}$; and blank refers to media without polypeptide complexes.
Figure 30:
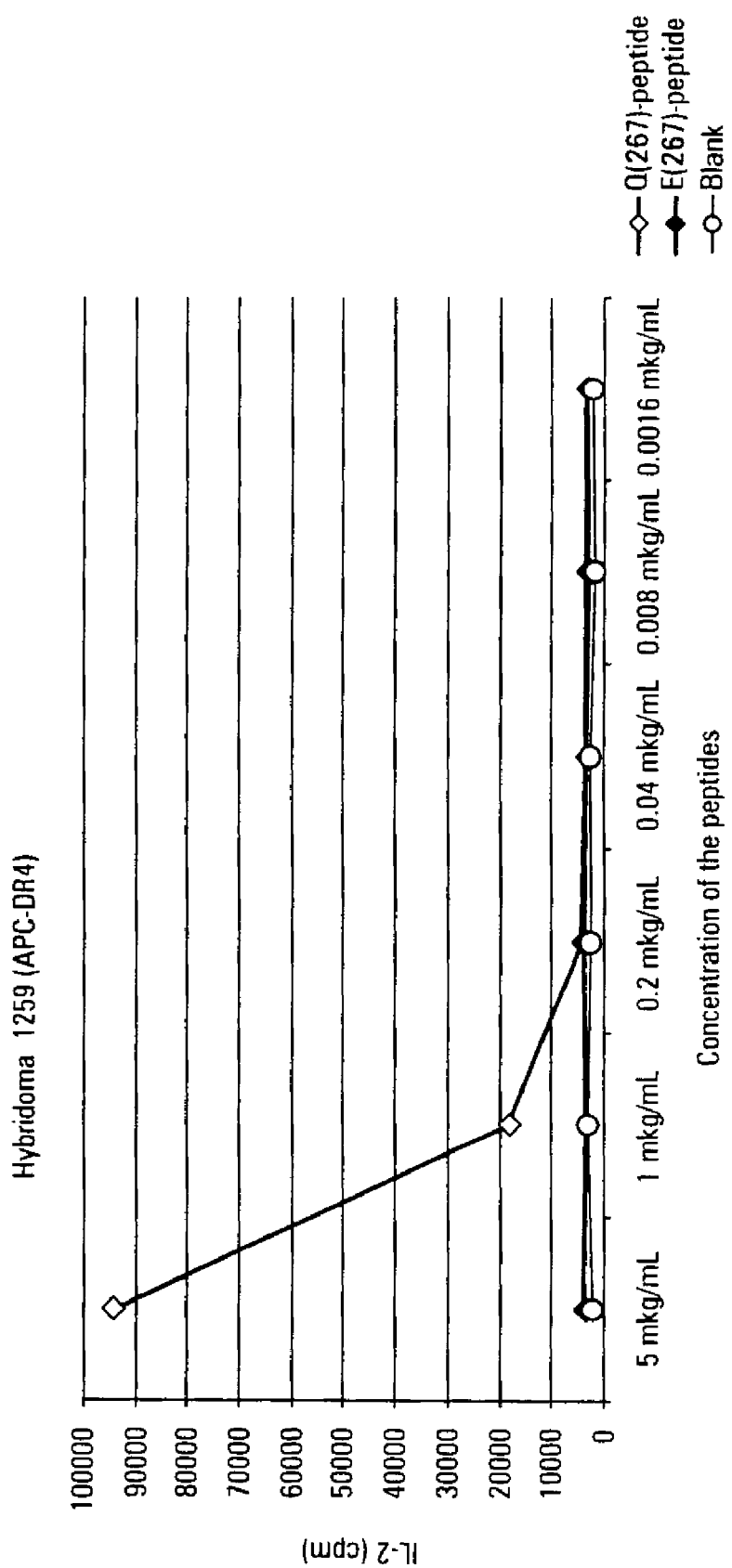
FIG. 30 is a graph plotting IL-2 production as measured by ELISA as a function of polypeptide concentration. DR4-restricted 1259 hybridoma cells were incubated with $CII_{(259-273Hyp-274)}$ and $CII_{(259-267E-273Hyp-274)}$ polypeptides. In the legend, Q(267)-peptide refers to $CII_{(259-273Hyp-274)}$; E(267)-peptide refers to $CII_{(259-267E-273Hyp-274)}$; and blank refers to media without polypeptide complexes.

CII$_{(256\text{-}270)}$-containing polypeptides and triple helical polypeptide complexes CII$_{(256\text{-}270)}$ polypeptides (Gly-Glu-Pro-Gly-Ile-Ala-Gly-Phe-Lys-Gly-Glu-Gln-Gly-Pro-Lys; SEQ ID NO:60) stimulated CII$_{(256\text{-}270)}$/Aq-specific T cell hybridoma cells when presented by formalin-fixed spleen cells. In contrast, neither [(Pro-Hyp-Gly)$_5$-CII$_{(257\text{-}258Hyp\text{-}273T\text{-}274)}$]$_3$-L$_{Ahx}$ (THP 4) nor KTA-[Gly-(Gly-Pro-Hyp)$_5$-Gly-CII$_{(257\text{-}258Hyp\text{-}273T\text{-}274)}$]$_3$-L(F)$_{Ahx}$ (THP 2) stimulated CII$_{(256\text{-}270)}$/Aq-specific T cell hybridoma cells when presented by formalin-fixed spleen cells (FIGS. 25–26). Thus, the CII$_{(256\text{-}270)}$ polypeptide, but not the triple helical polypeptide complexes having interpolypeptide linkages, bound to MHC class II (Aq) molecules on the surface of the formalin-fixed APC. Non-fixed APC, however, were potent stimulators for both the triple helical polypeptide complexes and for the CII$_{(256\text{-}270)}$ polypeptide. In fact, the triple helical polypeptide complexes resulted in 25 to 50 times more IL-2 production than the CII$_{(256\text{-}270)}$ polypeptide. Thus, the triple helical polypeptide complexes appear to be processed in antigen presenting cells and presented to T cells more efficiently than the CII$_{(256\text{-}270)}$ polypeptide, which lacks interpolypeptide linkages.

CII$_{(259\text{-}267E\text{-}273Hyp\text{-}274)}$-containing polypeptides

Transglutaminase (coagulation factor XIII) is present in inflamed and lymphoid infiltrate containing tissues such as the inflamed joints and intestine. Transglutaminase can change Q to E in contexts where Q is positioned in proximity to glycine (G) and P (proline) (e.g., in GQXP motifs). The Q at position 267 in the CII polypeptide resides in such a context and could be changed by transglutaminase to E in some individuals.

To examine the effects of possible changes from Q to E, CII$_{(259\text{-}273Hyp\text{-}274)}$ and CII$_{(259\text{-}267E\text{-}273Hyp\text{-}274)}$ polypeptides were incubated with MHC class II-restricted T hybridoma cells. FIGS. 27–30 show that some, but not other, MHC class II-restricted T hybridomas recognize the CII$_{(259\text{-}267E\text{-}273Hyp\text{-}274)}$ epitope. These results demonstrate that that the CII$_{(259\text{-}267E\text{-}273Hyp\text{-}274)}$ epitope can bind an MHC class II molecule and interact with a T cell receptor. This finding indicates that some individuals' immune systems recognize only wild type CII, while other individuals' immune systems recognize both wild type CII and CII containing a Q to E change at position 276.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting an antibody in a sample from a mammal, wherein said antibody has specificity for a triple polypeptide complex, wherein said triple polypeptide complex comprises three polypeptides, wherein each of said three polypeptides comprises a triple helix formation sequence, wherein each of said three polypeptides comprises at least one interpolypeptide linkage such that each polypeptide is attached to at least one of the other two polypeptides of said three polypeptides, and wherein
   at least one polypeptide of said three polypeptides comprises an amino acid sequence having at least 80% identity to the sequence set forth in SEQ ID NO:30 or 45;
said method comprising:
   (a) contacting said sample with said triple polypeptide complex, and
   (b) determining the presence or absence of said antibody bound to said triple polypeptide complex, wherein the presence of bound antibody indicates that said sample contains said antibody.

2. The method of claim 1, wherein said mammal is a human.

3. The method of claim 1, wherein said sample is serum.

4. The method of claim 1, wherein said antibody is an anti-collagen antibody.

5. The method of claim 1, wherein said antibody is bound to a B-cell.

6. The method of claim 1, wherein said antibody is a circulating antibody.

* * * * *

UNITED STATES PATENT AND TRADEMARK OFFICE
CERTIFICATE OF CORRECTION

PATENT NO. : 7,148,020 B2  Page 1 of 1
APPLICATION NO. : 10/194441
DATED : December 12, 2006
INVENTOR(S) : Rikard Holmdahl et al.

It is certified that error appears in the above-identified patent and that said Letters Patent is hereby corrected as shown below:

Item (75) Inventors, "Jan Ake Engstrom", please delete "Bălinge" and insert --Bälinge-- therefor;

Item (73) Title Page, Assignee, please delete "Molndal" and insert --Mölndal-- therefor;

Item (56) Title Page, References Cited, Other Publications, fourth "Broddefalk et al." reference, please delete "1998" and insert --1999-- therefor;

Item (56) Title Page (Page 2), References Cited, Other Publications, "Tanaka et al." reference, please delete "'998" and insert --1998-- therefor.

Signed and Sealed this

Twentieth Day of November, 2007

JON W. DUDAS
*Director of the United States Patent and Trademark Office*

SEQUENCE LISTING

<160> NUMBER OF SEQ ID NOS: 87

<210> SEQ ID NO 1
<211> LENGTH: 1014
<212> TYPE: PRT
<213> ORGANISM: Homo sapiens

<400> SEQUENCE: 1

```
Gly Pro Met Gly Pro Met Gly Pro Arg Gly Pro Pro Gly Pro Ala Gly
 1               5                  10                  15

Ala Pro Gly Pro Gln Gly Phe Gln Gly Asn Pro Gly Glu Pro Gly Glu
            20                  25                  30

Pro Gly Val Ser Gly Pro Met Gly Pro Arg Gly Pro Pro Gly Pro Pro
        35                  40                  45

Gly Lys Pro Gly Asp Asp Gly Glu Ala Gly Lys Pro Gly Lys Ala Gly
    50                  55                  60

Glu Arg Gly Pro Pro Gly Pro Gln Gly Ala Arg Gly Phe Pro Gly Thr
65                  70                  75                  80

Pro Gly Leu Pro Gly Val Lys Gly His Arg Gly Tyr Pro Gly Leu Asp
                85                  90                  95

Gly Ala Lys Gly Glu Ala Gly Ala Pro Gly Val Lys Gly Glu Ser Gly
            100                 105                 110

Ser Pro Gly Glu Asn Gly Ser Pro Gly Pro Met Gly Pro Arg Gly Leu
        115                 120                 125

Pro Gly Glu Arg Gly Arg Thr Gly Pro Ala Gly Ala Ala Gly Ala Arg
    130                 135                 140

Gly Asn Asp Gly Gln Pro Gly Pro Ala Gly Pro Pro Gly Pro Val Gly
145                 150                 155                 160

Pro Ala Gly Gly Pro Gly Phe Pro Gly Ala Pro Gly Ala Lys Gly Glu
                165                 170                 175

Ala Gly Pro Thr Gly Ala Arg Gly Pro Glu Gly Ala Gln Gly Pro Arg
            180                 185                 190

Gly Glu Pro Gly Thr Pro Gly Ser Pro Gly Pro Ala Gly Ala Ser Gly
        195                 200                 205

Asn Pro Gly Thr Asp Gly Ile Pro Gly Ala Lys Gly Ser Ala Gly Ala
    210                 215                 220

Pro Gly Ile Ala Gly Ala Pro Gly Phe Pro Gly Pro Arg Gly Pro Pro
225                 230                 235                 240

Gly Pro Gln Gly Ala Thr Gly Pro Leu Gly Pro Lys Gly Gln Thr Gly
                245                 250                 255

Glu Pro Gly Ile Ala Gly Phe Lys Gly Glu Gln Gly Pro Lys Gly Glu
            260                 265                 270

Pro Gly Pro Ala Gly Pro Gln Gly Ala Pro Gly Pro Ala Gly Glu Glu
        275                 280                 285

Gly Lys Arg Gly Ala Arg Gly Glu Pro Gly Val Gly Pro Ile Gly
    290                 295                 300

Pro Pro Gly Glu Arg Gly Ala Pro Gly Asn Arg Gly Phe Pro Gly Gln
305                 310                 315                 320

Asp Gly Leu Ala Gly Pro Lys Gly Ala Pro Gly Glu Arg Gly Pro Ser
                325                 330                 335

Gly Leu Ala Gly Pro Lys Gly Ala Asn Gly Asp Pro Gly Arg Pro Gly
            340                 345                 350

Glu Pro Gly Leu Pro Gly Ala Arg Gly Leu Thr Gly Arg Pro Gly Asp
```

```
                355                 360                 365
Ala Gly Pro Gln Gly Lys Val Gly Pro Ser Gly Ala Pro Gly Glu Asp
    370                 375                 380
Gly Arg Pro Gly Pro Gly Pro Gln Gly Ala Arg Gly Gln Pro Gly
385                 390                 395                 400
Val Met Gly Phe Pro Gly Pro Lys Gly Ala Asn Gly Glu Pro Gly Lys
                405                 410                 415
Ala Gly Glu Lys Gly Leu Pro Gly Ala Pro Gly Leu Arg Gly Leu Pro
                420                 425                 430
Gly Lys Asp Gly Glu Thr Gly Ala Ala Gly Pro Pro Gly Pro Ala Gly
            435                 440                 445
Pro Ala Gly Glu Arg Gly Glu Gln Gly Ala Pro Gly Pro Ser Gly Phe
    450                 455                 460
Gln Gly Leu Pro Gly Pro Gly Pro Pro Gly Glu Gly Gly Lys Gln
465                 470                 475                 480
Gly Asp Gln Gly Val Pro Gly Glu Ala Gly Ala Pro Gly Leu Val Gly
                485                 490                 495
Pro Arg Gly Glu Arg Gly Phe Pro Gly Glu Arg Gly Ser Pro Gly Ala
                500                 505                 510
Gln Gly Leu Gln Gly Pro Arg Gly Leu Pro Gly Thr Pro Gly Thr Asp
            515                 520                 525
Gly Pro Lys Gly Ala Ser Gly Pro Ala Gly Pro Pro Gly Ala Gln Gly
        530                 535                 540
Pro Pro Gly Leu Gln Gly Met Pro Gly Glu Arg Gly Ala Ala Gly Ile
545                 550                 555                 560
Ala Gly Pro Lys Gly Asp Arg Gly Asp Val Gly Glu Lys Gly Pro Glu
                565                 570                 575
Gly Ala Pro Gly Lys Asp Gly Gly Arg Gly Leu Thr Gly Pro Ile Gly
                580                 585                 590
Pro Pro Gly Pro Ala Gly Ala Asn Gly Glu Lys Gly Glu Val Gly Pro
            595                 600                 605
Pro Gly Pro Ala Gly Ser Ala Gly Ala Arg Gly Ala Pro Gly Glu Pro
        610                 615                 620
Gly Glu Thr Gly Pro Pro Gly Pro Ala Gly Phe Ala Gly Pro Pro Gly
625                 630                 635                 640
Ala Asp Gly Gln Pro Gly Ala Lys Gly Glu Gln Gly Glu Ala Gly Gln
                645                 650                 655
Lys Gly Asp Ala Gly Ala Pro Gly Pro Gln Gly Ser Gly Ala Pro
            660                 665                 670
Gly Pro Gln Gly Pro Thr Gly Val Thr Gly Pro Lys Gly Ala Arg Gly
        675                 680                 685
Ala Gln Gly Pro Pro Gly Ala Thr Gly Phe Pro Gly Ala Ala Gly Arg
    690                 695                 700
Val Gly Pro Pro Gly Ser Asn Gly Asn Pro Gly Pro Pro Gly Pro Pro
705                 710                 715                 720
Gly Pro Ser Gly Lys Asp Gly Pro Lys Gly Ala Arg Gly Asp Ser Gly
                725                 730                 735
Pro Pro Gly Arg Ala Gly Glu Pro Gly Leu Gln Gly Pro Ala Gly Pro
            740                 745                 750
Pro Gly Glu Lys Gly Glu Pro Gly Asp Asp Gly Pro Ser Gly Ala Glu
        755                 760                 765
Gly Pro Pro Gly Pro Gln Gly Leu Ala Gly Gln Arg Gly Ile Val Gly
    770                 775                 780
```

-continued

Leu Pro Gly Gln Arg Gly Glu Arg Gly Phe Pro Gly Leu Pro Gly Pro
785                 790                 795                 800

Ser Gly Glu Pro Gly Lys Gln Gly Ala Pro Gly Ala Ser Gly Asp Arg
            805                 810                 815

Gly Pro Pro Gly Pro Val Gly Pro Pro Gly Leu Thr Gly Pro Ala Gly
            820                 825                 830

Glu Pro Gly Arg Glu Gly Ser Pro Gly Ala Asp Gly Pro Pro Gly Arg
            835                 840                 845

Asp Gly Ala Ala Gly Val Lys Gly Asp Arg Gly Glu Thr Gly Ala Val
850                 855                 860

Gly Ala Pro Gly Ala Pro Gly Pro Pro Gly Ser Pro Gly Pro Ala Gly
865                 870                 875                 880

Pro Thr Gly Lys Gln Gly Asp Arg Gly Glu Ala Gly Ala Gln Gly Pro
            885                 890                 895

Met Gly Pro Ser Gly Pro Ala Gly Ala Arg Gly Ile Gln Gly Pro Gln
            900                 905                 910

Gly Pro Arg Gly Asp Lys Gly Glu Ala Gly Glu Pro Gly Glu Arg Gly
            915                 920                 925

Leu Lys Gly His Arg Gly Phe Thr Gly Leu Gln Gly Leu Pro Gly Pro
930                 935                 940

Pro Gly Pro Ser Gly Asp Gln Gly Ala Ser Gly Pro Ala Gly Pro Ser
945                 950                 955                 960

Gly Pro Arg Gly Pro Pro Gly Pro Val Gly Pro Ser Gly Lys Asp Gly
            965                 970                 975

Ala Asn Gly Ile Pro Gly Pro Ile Gly Pro Pro Gly Pro Arg Gly Arg
            980                 985                 990

Ser Gly Glu Thr Gly Pro Ala Gly Pro Pro Gly Asn Pro Gly Pro Pro
            995                 1000                1005

Gly Pro Pro Gly Pro Pro
    1010

<210> SEQ ID NO 2
<211> LENGTH: 4464
<212> TYPE: DNA
<213> ORGANISM: Homo sapiens

<400> SEQUENCE: 2
atgattcgcc tcgggctcc ccagtcgctg gtgctgctga cgctgctcgt cgccgctgtc      60
cttcggtgtc agggccagga tgtccaggag gctggcagct gtgtgcagga tgggcagagg     120
tataatgata aggatgtgtg gaagccggag ccctgccgga tctgtgtctg tgacactggg     180
actgtcctct gcgacgacat aatctgtgaa gacgtgaaag actgcctcag ccctgagatc     240
cccttcggag agtgctgccc catctgccca actgacctcg ccactgccag tgggcaacca     300
ggaccaaagg gacagaaagg agaacctgga gacatcaagg atattgtagg acccaaagga     360
cctcctgggc tcagggacc tgcagggaa caaggaccca gagggatcg tggtgacaaa       420 ggtgaaaaag gtgccctgg acctcgtggc agagatggaa acctgggac ccctggaaat      480 cctggcccc ctggtcctcc cggcccccct ggtccccctg tcttggtgg aaactttgct      540 gcccagatgg ctggaggatt tgatgaaaag gctggtggcg cccagttggg agtaatgcaa     600
ggaccaatgg gccccatggg acctcgagga cctccaggcc tgcaggtgc tcctgggcct     660 caaggatttc aaggcaatcc tggtgaacct ggtgaacctg gtgtctctgg tcccatgggt     720
ccccgtggtc ctcctggtcc ccctggaaag cctggtgatg atggtgaagc tggaaaacct     780

-continued

```
ggaaaagctg gtgaaggggg tccgcctggt cctcaggtg ctcgtggttt cccaggaacc    840
ccaggccttc ctggtgtcaa aggtcacaga ggttatccag gcctggacgg tgctaaggga    900
gaggcgggtg ctcctggtgt gaagggtgag agtggttccc cgggtgagaa cggatctccg    960
ggcccaatgg gtcctcgtgg cctgcctggt gaaagaggac ggactggccc tgctggcgct   1020
gcgggtgccc gaggcaacga tggtcagcca ggccccgcag gtcctccggg tcctgtcggt   1080
cctgctggtg gtcctggctt ccctggtgct cctggagcca agggtgaagc cggcccact    1140
ggtgcccgtg gtcctgaagg tgctcaaggt cctcgcggtg aacctggtac tcctgggtcc   1200
cctgggcctg ctggtgcctc cggtaaccct ggaacagatg gaattcctgg agccaaagga   1260
tctgctggtg ctcctggcat tgctggtgct cctggcttcc ctgggccacg ggtcctcct    1320
ggccctcaag gtgcaactgg tcctctgggc ccgaaaggtc agacgggtga acctggtatt   1380
gctggcttca aggtgaaca aggccccaag ggagaacctg ccctgctgg ccccagggga     1440
gcccctggac ccgctggtga agaaggcaag agaggtgccc gtggagagcc tggtggcgtt   1500
gggcccatcg gtccccctgg agaaagaggt gctcccggaa accgcggttt ccaggtcaa    1560
gatggtctgg caggtcccaa gggagcccct ggagagcgag ggcccagtgg tcttgctggc   1620
cccaagggag ccaacggtga ccctggccgt cctggagaac ctggccttcc tggagcccgg   1680
ggtctcactg gccgccctgg tgatgctggt cctcaaggca agttggccc ttctggagcc    1740
cctggtgaag atggtcgtcc tggacctcca ggtcctcagg gggctcgtgg gcagcctggt   1800
gtcatgggtt tccctggccc caaggtgcc aacggtgagc ctggcaaagc tggtgagaag   1860
ggactgcctg gtgctcctgg tctgaggggt cttcctggca agatggtga cacaggtgct    1920
gcaggacccc ctgccctgc tggacctgct ggtgaacgag gcgagcaggg tgctcctggg     1980
ccatctgggt tccagggact tcctggcccc ctggtccccc aggtgaagg tggaaaacca    2040
ggtgaccagg gtgttcccgg tgaagctgga gcccctggcc tcgtgggtcc caggggtgaa   2100
cgaggtttcc caggtgaacg tggctctccc ggtgcccagg gcctccaggg tccccgtggc   2160
ctccccggca ctcctggcac tgatggtccc aaaggtgcat ctggcccagc aggcccccct   2220
ggcgcacagg gcctccagg tcttcaggga atgcctggcg agagggagc agctggtatc     2280
gctgggccca aggcgacag gggtgacgtt ggtgagaaag gccctgaggg agcccctgga    2340
aaggatggtg gacgaggcct gacaggtccc attggccccc ctggccagc tggtgctaac    2400
ggcgagaagg gagaagttgg acctcctggt cctgcaggaa gtgctggtgc tcgtggcgct   2460
ccgggtgaac gtggagagac tggccccccc ggaccagcgg gatttgctgg gcctcctggt   2520
gctgatggcc agcctgggc caaggtgag caaggagagg ccggccagaa aggcgatgct     2580
ggtgcccctg gtcctcaggg cccctctgga gcacctgggc ctcagggtcc tactggagtg   2640
actggtccta aaggagcccg aggtgcccaa ggccccccgg gagccactgg attccctgga    2700
gctgctggcc gcgttggacc cccaggctcc aatggcaacc ctggaccccc tggtccccct   2760
ggtcttctg gaaaagatgg tcccaaaggt gctcgaggag acagcggccc cctggccga    2820
gctggtgaac ccggcctcca aggtcctgct ggacccctg gcgagaaggg agagcctgga    2880
gatgacggtc cctctggtgc cgaaggtcca ccaggtcccc aggtctggc tggtcagaga    2940
ggcatcgtcg gtctgcctgg gcaacgtggt gagagaggat ccctggctt gcctggccca    3000
tcgggtgagc ccggcaagca gggtgctcct ggagcatctg gagacagagg tcctcctggc   3060
cccgtgggtc tccctggcct gacgggtcct gcaggtgaac ccggacgaga gggaagcccc   3120
```

-continued

```
ggtgctgatg cccccctgg cagagatggc gctgctggag tcaagggtga tcgtggtgag   3180
actggtgctg tgggagctcc tggagcccct gggccccctg gctcccctgg cccgctggt    3240
ccaactggca agcaaggaga cagaggagaa gctggtgcac aaggcccat gggaccctca   3300
ggaccagctg gagcccgggg aatccaggt cctcaaggcc ccagaggtga caaaggagag   3360
gctggagagc ctggcgagag aggcctgaag ggacaccgtg gcttcactgg tctgcaggt    3420
ctgcccggcc ctcctggtcc ttctggagac caaggtgctt ctggtcctgc tggtccttct   3480
ggccctagag tcctcctgg ccccgtcggt ccctctggca agatggtgc taatggaatc     3540
cctggcccca ttgggcctcc tggtccccgt ggacgatcag gcgaaaccgg tcctgctggt   3600
cctcctggaa atcctgggcc ccctggtcct ccaggtcccc ctggccctgg catcgacatg   3660
tccgcctttg ctggcttagg cccgagagag aagggccccg accccctgca gtacatgcgg   3720
gccgaccagg cagccggtgg cctgagacag catgacgccg aggtggatgc cacactcaag   3780
tccctcaaca accagattga gagcatccgc agccccgagg gctcccgcaa gaaccctgct   3840
cgcacctgca gagacctgaa actctgccac cctgagtgga gagtggaga ctactggatt   3900
gaccccaacc aaggctgcac cttggacgcc atgaaggttt ctgcaacat ggagactggc    3960
gagacttgcg tctaccccaa tccagcaaac gttcccaaga gaactggtg gagcagcaag   4020
agcaaggaga agaaacacat ctggtttgga gaaaccatca atggtggctt ccatttcagc   4080
tatggagatg acaatctggc tcccaacact gccaacgtcc agatgacctt cctacgcctg   4140
ctgtccacgg aagctcccca gaacatcacc taccactgca agaacagcat tgcctatctg   4200
gacgaagcag ctggcaacct caagaaggcc ctgctcatcc agggctccaa tgacgtggag   4260
atccgggcag agggcaatag caggttcacg tacactgccc tgaaggatgg ctgcacgaaa   4320
cataccggta agtggggcaa gactgttatc gagtaccggt cacagaagac ctcacgcctc   4380
cccatcattg acattgcacc catggacata ggagggcccg agcaggaatt cggtgtggac   4440
ataggggccgg tctgcttctt gtaa                                         4464
```

<210> SEQ ID NO 3
<211> LENGTH: 15
<212> TYPE: PRT
<213> ORGANISM: Homo sapiens

<400> SEQUENCE: 3

Gly Glu Pro Gly Ile Ala Gly Phe Lys Gly Glu Gln Gly Pro Lys
1               5                   10                  15

<210> SEQ ID NO 4
<211> LENGTH: 9
<212> TYPE: PRT
<213> ORGANISM: Homo sapiens

<400> SEQUENCE: 4

Gly Ala Arg Gly Leu Thr Gly Arg Pro
1               5

<210> SEQ ID NO 5
<211> LENGTH: 12
<212> TYPE: PRT
<213> ORGANISM: Homo sapiens

<400> SEQUENCE: 5

Gly Ala Arg Gly Leu Thr Gly Arg Pro Gly Asp Ala
1               5                   10

```
<210> SEQ ID NO 6
<211> LENGTH: 16
<212> TYPE: PRT
<213> ORGANISM: Homo sapiens

<400> SEQUENCE: 6

Gly Ile Ala Gly Phe Lys Gly Glu Gln Gly Pro Lys Gly Glu Pro Gly
 1               5                  10                  15

<210> SEQ ID NO 7
<211> LENGTH: 10
<212> TYPE: PRT
<213> ORGANISM: Homo sapiens

<400> SEQUENCE: 7

Leu Val Gly Pro Arg Gly Glu Arg Phe Pro
 1               5                  10

<210> SEQ ID NO 8
<211> LENGTH: 14
<212> TYPE: PRT
<213> ORGANISM: Homo sapiens

<400> SEQUENCE: 8

Met Pro Gly Glu Arg Gly Ala Ala Gly Ile Ala Gly Pro Lys
 1               5                  10

<210> SEQ ID NO 9
<211> LENGTH: 5
<212> TYPE: PRT
<213> ORGANISM: Homo sapiens

<400> SEQUENCE: 9

His Arg Gly Phe Thr
 1               5

<210> SEQ ID NO 10
<211> LENGTH: 12
<212> TYPE: PRT
<213> ORGANISM: Homo sapiens

<400> SEQUENCE: 10

Arg Gly Ala Gln Gly Pro Pro Gly Ala Thr Gly Phe
 1               5                  10

<210> SEQ ID NO 11
<211> LENGTH: 7
<212> TYPE: PRT
<213> ORGANISM: Homo sapiens

<400> SEQUENCE: 11

Ala Gly Gln Arg Gly Ile Val
 1               5

<210> SEQ ID NO 12
<211> LENGTH: 19
<212> TYPE: PRT
<213> ORGANISM: Homo sapiens

<400> SEQUENCE: 12

Gly Pro Arg Gly Leu Pro Gly Glu Arg Gly Arg Thr Gly Pro Ala Gly
 1               5                  10                  15

Ala Ala Gly
```

<210> SEQ ID NO 13
<211> LENGTH: 13
<212> TYPE: PRT
<213> ORGANISM: Homo sapiens

<400> SEQUENCE: 13

Gly Asn Pro Gly Thr Asp Gly Ile Pro Gly Ala Lys Gly
1               5                   10

<210> SEQ ID NO 14
<211> LENGTH: 11
<212> TYPE: PRT
<213> ORGANISM: Homo sapiens

<400> SEQUENCE: 14

Ala Arg Gly Pro Glu Gly Ala Gln Gly Pro Arg
1               5                   10

<210> SEQ ID NO 15
<211> LENGTH: 14
<212> TYPE: PRT
<213> ORGANISM: Homo sapiens

<400> SEQUENCE: 15

Asp Ala Gly Pro Gln Gly Lys Val Gly Pro Ser Gly Ala Pro
1               5                   10

<210> SEQ ID NO 16
<211> LENGTH: 15
<212> TYPE: PRT
<213> ORGANISM: Homo sapiens

<400> SEQUENCE: 16

Pro Ser Gly Leu Ala Gly Pro Lys Gly Ala Asn Gly Asp Pro Gly
1               5                   10                  15

<210> SEQ ID NO 17
<211> LENGTH: 15
<212> TYPE: PRT
<213> ORGANISM: Homo sapiens

<400> SEQUENCE: 17

Lys Val Gly Pro Ser Gly Ala Pro Gly Glu Asp Gly Arg Pro Gly
1               5                   10                  15

<210> SEQ ID NO 18
<211> LENGTH: 15
<212> TYPE: PRT
<213> ORGANISM: Homo sapiens

<400> SEQUENCE: 18

Phe Pro Gly Pro Lys Gly Ala Asn Gly Glu Pro Gly Lys Ala Gly
1               5                   10                  15

<210> SEQ ID NO 19
<211> LENGTH: 15
<212> TYPE: PRT
<213> ORGANISM: Homo sapiens

<400> SEQUENCE: 19

Pro Pro Gly Pro Ala Gly Ala Asn Gly Glu Lys Gly Glu Val Gly
1               5                   10                  15

<210> SEQ ID NO 20

```
<211> LENGTH: 15
<212> TYPE: PRT
<213> ORGANISM: Homo sapiens

<400> SEQUENCE: 20

Pro Pro Gly Ala Asn Gly Asn Pro Gly Pro Ala Gly Pro Pro Gly
1               5                   10                  15

<210> SEQ ID NO 21
<211> LENGTH: 15
<212> TYPE: PRT
<213> ORGANISM: Homo sapiens

<400> SEQUENCE: 21

Ala Pro Gly Ile Ala Gly Ala Pro Gly Phe Pro Gly Pro Arg Gly
1               5                   10                  15

<210> SEQ ID NO 22
<211> LENGTH: 8
<212> TYPE: PRT
<213> ORGANISM: Homo sapiens

<400> SEQUENCE: 22

Gly His Arg Gly Tyr Pro Gly Leu
1               5

<210> SEQ ID NO 23
<211> LENGTH: 8
<212> TYPE: PRT
<213> ORGANISM: Homo sapiens

<400> SEQUENCE: 23

Gly Glu Arg Gly Phe Pro Gly Leu
1               5

<210> SEQ ID NO 24
<211> LENGTH: 8
<212> TYPE: PRT
<213> ORGANISM: Homo sapiens

<400> SEQUENCE: 24

Gly His Arg Gly Phe Thr Gly Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 9
<223> OTHER INFORMATION: hydroxyproline

<400> SEQUENCE: 25

Gly Ala Arg Gly Leu Thr Gly Arg Xaa
1               5

<210> SEQ ID NO 26
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
```

```
<222> LOCATION: 9
<223> OTHER INFORMATION: hydroxyproline

<400> SEQUENCE: 26

Gly Ala Arg Gly Leu Thr Gly Arg Xaa Gly Asp Ala
 1               5                  10

<210> SEQ ID NO 27
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 15
<223> OTHER INFORMATION: hydroxyproline

<400> SEQUENCE: 27

Gly Ile Ala Gly Phe Lys Gly Glu Gln Gly Pro Lys Gly Glu Xaa Gly
 1               5                  10                  15

<210> SEQ ID NO 28
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 11
<223> OTHER INFORMATION: hydroxyproline

<400> SEQUENCE: 28

Leu Val Gly Pro Arg Gly Glu Arg Gly Phe Xaa
 1               5                  10

<210> SEQ ID NO 29
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 2
<223> OTHER INFORMATION: hydroxyproline

<400> SEQUENCE: 29

Met Xaa Gly Glu Arg Gly Ala Ala Gly Ile Ala Gly Pro Lys
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3,8
<223> OTHER INFORMATION: citrulline modifications of arginine
<220> FEATURE:
<221> NAME/KEY: MOD_RES
<222> LOCATION: 9
<223> OTHER INFORMATION: hydroxyproline

<400> SEQUENCE: 30

Gly Ala Xaa Gly Leu Thr Gly Xaa Xaa Gly Asp Ala
 1               5                  10
```

```
<210> SEQ ID NO 31
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3,8
<223> OTHER INFORMATION: ornithine modifications of arginine
<220> FEATURE:
<221> NAME/KEY: MOD_RES
<222> LOCATION: 9
<223> OTHER INFORMATION: hydroxyproline

<400> SEQUENCE: 31

Gly Ala Xaa Gly Leu Thr Gly Xaa Xaa Gly Asp Ala
 1               5                  10

<210> SEQ ID NO 32
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 6
<223> OTHER INFORMATION: hydroxyproline

<400> SEQUENCE: 32

Gly Pro Arg Gly Leu Xaa Gly Glu Arg Gly Arg Thr Gly Pro Ala Gly
 1               5                  10                  15

Ala Ala Gly

<210> SEQ ID NO 33
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 9
<223> OTHER INFORMATION: hydroxyproline

<400> SEQUENCE: 33

Gly Asn Xaa Gly Thr Asp Gly Ile Xaa Gly Ala Lys Gly
 1               5                  10

<210> SEQ ID NO 34
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 14
<223> OTHER INFORMATION: hydroxyproline

<400> SEQUENCE: 34

Asp Ala Gly Pro Gln Gly Lys Val Gly Pro Ser Gly Ala Xaa
 1               5                  10

<210> SEQ ID NO 35
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 35

Gly Pro Thr Ser Ser Leu
 1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 8
<223> OTHER INFORMATION: hydroxyproline

<400> SEQUENCE: 36

Met Glu Met Gly Gly Leu Arg Xaa
 1               5

<210> SEQ ID NO 37
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 30
<223> OTHER INFORMATION: hydroxyproline

<400> SEQUENCE: 37

Gly Pro Thr Ser Ser Leu Gly Ile Ala Gly Phe Lys Gly Glu Gln Gly
 1               5                  10                  15

Pro Lys Gly Glu Pro Gly Met Glu Met Gly Gly Leu Arg Xaa
            20                  25                  30

<210> SEQ ID NO 38
<211> LENGTH: 9
<212> TYPE: PRT
<213> ORGANISM: Artificial Sequence
<220> FEATURE:
<223> OTHER INFORMATION: Synthetic

<400> SEQUENCE: 38

Gly Pro Arg Gly Pro Arg Gly Pro Arg
 1               5

<210> SEQ ID NO 39
<211> LENGTH: 20
<212> TYPE: PRT
<213> ORGANISM: Artificial Sequence
<220> FEATURE:
<223> OTHER INFORMATION: Synthetic

<400> SEQUENCE: 39

Glu Ser Phe Leu Glu Ser Phe Leu Glu Ser Phe Leu Glu Ser Phe Leu
 1               5                  10                  15

Glu Ser Phe Leu
            20

<210> SEQ ID NO 40
<211> LENGTH: 31
<212> TYPE: PRT
```

-continued

```
<213> ORGANISM: Artificial Sequence
<220> FEATURE:
<223> OTHER INFORMATION: Synthetic

<400> SEQUENCE: 40

Met Met Gly Pro Arg Gly Pro Arg Gly Pro Arg Glu Ser Phe Leu Glu
1               5                   10                  15

Ser Phe Leu Glu Ser Phe Leu Glu Ser Phe Leu Glu Ser Phe Leu
            20                  25                  30

<210> SEQ ID NO 41
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 24, 30, 33
<223> OTHER INFORMATION: hyroxyproline

<400> SEQUENCE: 41

Gly Pro Xaa Gly Pro Xaa Gly Pro Xaa Gly Pro Xaa Gly Pro Xaa Gly
1               5                   10                  15

Ala Arg Gly Leu Thr Gly Arg Xaa Gly Asp Ala Gly Pro Xaa Gly Pro
            20                  25                  30

Xaa

<210> SEQ ID NO 42
<211> LENGTH: 37
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 30, 34, 37
<223> OTHER INFORMATION: hydroxyproline

<400> SEQUENCE: 42

Gly Pro Xaa Gly Pro Xaa Gly Pro Xaa Gly Pro Xaa Gly Pro Xaa Gly
1               5                   10                  15

Ile Ala Gly Phe Lys Gly Glu Gln Gly Pro Lys Gly Glu Xaa Gly Gly
            20                  25                  30

Pro Xaa Gly Pro Xaa
        35

<210> SEQ ID NO 43
<211> LENGTH: 45
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 30, 39, 42, 45
<223> OTHER INFORMATION: hydroxyproline

<400> SEQUENCE: 43

Gly Pro Xaa Gly Pro Xaa Gly Pro Xaa Gly Pro Xaa Gly Pro Xaa Gly
1               5                   10                  15

Ile Ala Gly Phe Lys Gly Glu Gln Gly Pro Lys Gly Glu Xaa Gly Ala
            20                  25                  30

Arg Gly Leu Thr Gly Arg Xaa Gly Pro Xaa Gly Pro Xaa
        35              40                  45
```

```
<210> SEQ ID NO 44
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 17, 32, 35
<223> OTHER INFORMATION: hydroxyproline

<400> SEQUENCE: 44

Gly Pro Xaa Gly Pro Xaa Gly Pro Xaa Gly Pro Xaa Gly Pro Xaa Met
 1               5                  10                  15

Xaa Gly Glu Arg Gly Ala Ala Gly Ile Ala Gly Pro Lys Gly Pro Xaa
                 20                  25                  30

Gly Pro Xaa
         35

<210> SEQ ID NO 45
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 24, 30, 33
<223> OTHER INFORMATION: hydroxyproline
<220> FEATURE:
<221> NAME/KEY: MOD_RES
<222> LOCATION: 18, 23
<223> OTHER INFORMATION: citrulline modifications of arginine

<400> SEQUENCE: 45

Gly Pro Xaa Gly Pro Xaa Gly Pro Xaa Gly Pro Xaa Gly Pro Xaa Gly
 1               5                  10                  15

Ala Xaa Gly Leu Thr Gly Xaa Xaa Gly Asp Ala Gly Pro Xaa Gly Pro
                 20                  25                  30

Xaa

<210> SEQ ID NO 46
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 26, 29, 32
<223> OTHER INFORMATION: hydroxyproline

<400> SEQUENCE: 46

Gly Pro Xaa Gly Pro Xaa Gly Pro Xaa Gly Pro Xaa Gly Pro Xaa Leu
 1               5                  10                  15

Val Gly Pro Arg Gly Glu Arg Gly Phe Xaa Gly Pro Xaa Gly Pro Xaa
                 20                  25                  30

<210> SEQ ID NO 47
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
```

<222> LOCATION: 3, 6, 9, 12, 15, 24, 27, 30
<223> OTHER INFORMATION: hydroxyproline

<400> SEQUENCE: 47

```
Gly Pro Xaa Gly Pro Xaa Gly Pro Xaa Gly Pro Xaa Gly Pro Xaa Gly
1               5                   10                  15

Ala Arg Gly Leu Thr Gly Arg Xaa Gly Pro Xaa Gly Pro Xaa
            20                  25                  30
```

<210> SEQ ID NO 48
<211> LENGTH: 1014
<212> TYPE: PRT
<213> ORGANISM: Mus musculus

<400> SEQUENCE: 48

```
Gly Pro Met Gly Pro Met Gly Pro Arg Gly Pro Gly Pro Ala Gly
1               5                   10                  15

Ala Pro Gly Pro Gln Gly Phe Gln Gly Asn Pro Gly Glu Pro Gly Glu
            20                  25                  30

Pro Gly Val Ser Gly Pro Met Gly Pro Arg Gly Pro Pro Gly Pro Ala
        35                  40                  45

Gly Lys Pro Gly Asp Asp Gly Glu Ala Gly Lys Pro Gly Lys Ser Gly
    50                  55                  60

Glu Arg Gly Leu Pro Gly Pro Gln Gly Ala Arg Gly Phe Pro Gly Thr
65                  70                  75                  80

Pro Gly Leu Pro Gly Val Lys Gly His Arg Gly Tyr Pro Gly Leu Asp
            85                  90                  95

Gly Ala Lys Gly Glu Ala Gly Ala Pro Gly Val Lys Gly Glu Ser Gly
            100                 105                 110

Ser Pro Gly Glu Asn Gly Ser Pro Gly Pro Met Gly Pro Arg Gly Leu
        115                 120                 125

Pro Gly Glu Arg Gly Arg Thr Gly Pro Ala Gly Ala Ala Gly Ala Arg
130                 135                 140

Gly Asn Asp Gly Gln Pro Gly Pro Ala Gly Pro Pro Gly Pro Val Gly
145                 150                 155                 160

Pro Ala Gly Gly Pro Gly Phe Pro Gly Ala Pro Gly Ala Lys Gly Glu
            165                 170                 175

Ala Gly Pro Thr Gly Ala Arg Gly Pro Glu Gly Ala Gln Gly Ser Arg
            180                 185                 190

Gly Glu Pro Gly Asn Pro Gly Ser Pro Gly Pro Ala Gly Ala Ser Gly
        195                 200                 205

Asn Pro Gly Thr Asp Gly Ile Pro Gly Ala Lys Gly Ser Ala Gly Ala
210                 215                 220

Pro Gly Ile Ala Gly Ala Pro Gly Phe Pro Gly Pro Arg Gly Pro Pro
225                 230                 235                 240

Gly Pro Gln Gly Ala Thr Gly Pro Leu Gly Pro Lys Gly Gln Ala Gly
            245                 250                 255

Glu Pro Gly Ile Ala Gly Phe Lys Gly Asp Gln Gly Pro Lys Gly Glu
            260                 265                 270

Thr Gly Pro Ala Gly Pro Gln Gly Ala Pro Gly Pro Ala Gly Glu Glu
        275                 280                 285

Gly Lys Arg Gly Ala Arg Gly Glu Pro Gly Gly Ala Gly Pro Ile Gly
            290                 295                 300

Pro Pro Gly Glu Arg Gly Ala Pro Gly Asn Arg Gly Phe Pro Gly Gln
305                 310                 315                 320
```

-continued

```
Asp Gly Leu Ala Gly Pro Lys Gly Ala Pro Gly Glu Arg Gly Pro Ser
            325                 330                 335
Gly Leu Ala Gly Pro Lys Gly Ala Asn Gly Asp Pro Gly Arg Pro Gly
        340                 345                 350
Glu Pro Gly Leu Pro Gly Ala Arg Gly Leu Thr Gly Arg Pro Gly Asp
            355                 360                 365
Ala Gly Pro Gln Gly Lys Val Gly Pro Ser Gly Ala Pro Gly Glu Asp
        370                 375                 380
Gly Arg Pro Gly Pro Gly Pro Gln Gly Ala Arg Gly Gln Pro Gly
385                 390                 395                 400
Val Met Gly Phe Pro Gly Pro Lys Gly Ala Asn Gly Glu Pro Gly Lys
                405                 410                 415
Ala Gly Glu Lys Gly Leu Ala Gly Ala Pro Gly Leu Arg Gly Leu Pro
            420                 425                 430
Gly Lys Asp Gly Glu Thr Gly Ala Ala Gly Pro Pro Gly Pro Ser Gly
        435                 440                 445
Pro Ala Gly Glu Arg Gly Glu Gln Gly Ala Pro Gly Pro Ser Gly Phe
    450                 455                 460
Gln Gly Leu Pro Gly Pro Gly Pro Pro Gly Glu Gly Gly Lys Gln
465                 470                 475                 480
Gly Asp Gln Gly Ile Pro Gly Glu Ala Gly Ala Pro Gly Leu Val Gly
                485                 490                 495
Pro Arg Gly Glu Arg Gly Phe Pro Gly Glu Arg Gly Ser Pro Gly Ala
            500                 505                 510
Gln Gly Leu Gln Gly Pro Arg Gly Leu Pro Gly Thr Pro Gly Thr Asp
        515                 520                 525
Gly Pro Lys Gly Ala Ala Gly Pro Asp Gly Pro Pro Gly Ala Gln Gly
    530                 535                 540
Pro Pro Gly Leu Gln Gly Met Pro Gly Glu Arg Gly Ala Ala Gly Ile
545                 550                 555                 560
Ala Gly Pro Lys Gly Asp Arg Gly Asp Val Gly Glu Lys Gly Pro Glu
                565                 570                 575
Gly Ala Pro Gly Lys Asp Gly Gly Arg Gly Leu Thr Gly Pro Ile Gly
            580                 585                 590
Pro Pro Gly Pro Ala Gly Ala Asn Gly Glu Lys Gly Glu Val Gly Pro
        595                 600                 605
Pro Gly Pro Ser Gly Ser Thr Gly Ala Arg Gly Ala Pro Gly Glu Pro
    610                 615                 620
Gly Glu Thr Gly Pro Pro Gly Pro Ala Gly Phe Ala Gly Pro Pro Gly
625                 630                 635                 640
Ala Asp Gly Gln Pro Gly Ala Lys Gly Asp Gln Gly Glu Ala Gly Gln
                645                 650                 655
Lys Gly Asp Ala Gly Ala Pro Gly Pro Gln Gly Pro Ser Gly Ala Pro
            660                 665                 670
Gly Pro Gln Gly Pro Thr Gly Val Thr Gly Pro Lys Gly Ala Arg Gly
        675                 680                 685
Ala Gln Gly Pro Pro Gly Ala Thr Gly Phe Pro Gly Ala Ala Gly Arg
    690                 695                 700
Val Gly Pro Pro Gly Ala Asn Gly Asn Pro Gly Pro Ala Gly Pro Pro
705                 710                 715                 720
Gly Pro Ala Gly Lys Asp Gly Pro Lys Gly Val Arg Gly Asp Ser Gly
                725                 730                 735
Pro Pro Gly Arg Ala Gly Asp Pro Gly Leu Gln Gly Pro Ala Gly Ala
```

-continued

```
                        740                 745                 750
        Pro Gly Glu Lys Gly Glu Pro Gly Asp Asp Gly Pro Ser Gly Leu Asp
                    755                 760                 765
        Gly Pro Pro Gly Pro Gln Gly Leu Ala Gly Gln Arg Gly Ile Val Gly
                770                 775                 780
        Leu Pro Gly Gln Arg Gly Glu Arg Gly Phe Pro Gly Leu Pro Gly Pro
        785                 790                 795                 800
        Ser Gly Glu Pro Gly Lys Gln Gly Ala Pro Gly Ala Ser Gly Asp Arg
                        805                 810                 815
        Gly Pro Pro Gly Pro Val Gly Pro Pro Gly Leu Thr Gly Pro Ala Gly
                    820                 825                 830
        Glu Pro Gly Arg Glu Gly Ser Pro Gly Ala Asp Gly Pro Pro Gly Arg
                835                 840                 845
        Asp Gly Ala Ala Gly Val Lys Gly Asp Arg Gly Glu Thr Gly Ala Leu
        850                 855                 860
        Gly Ala Pro Gly Ala Pro Gly Pro Pro Gly Ser Pro Gly Pro Ala Gly
                        865                 870                 875                 880
        Pro Thr Gly Lys Gln Gly Asp Arg Gly Glu Ala Gly Ala Gln Gly Pro
                    885                 890                 895
        Met Gly Pro Ser Gly Pro Ala Gly Ala Arg Gly Ile Ala Gly Pro Gln
                900                 905                 910
        Gly Pro Arg Gly Asp Lys Gly Glu Ser Gly Glu Gln Gly Glu Arg Gly
                    915                 920                 925
        Leu Lys Gly His Arg Gly Phe Thr Gly Leu Gln Gly Leu Pro Gly Pro
                930                 935                 940
        Pro Gly Pro Ser Gly Asp Gln Gly Ala Ser Gly Pro Ala Gly Pro Ser
        945                 950                 955                 960
        Gly Pro Arg Gly Pro Pro Gly Pro Val Gly Pro Ser Gly Lys Asp Gly
                        965                 970                 975
        Ser Asn Gly Ile Pro Gly Pro Ile Gly Pro Pro Gly Pro Arg Gly Arg
                    980                 985                 990
        Ser Gly Glu Thr Gly Pro Val Gly Pro Pro Gly Ser Pro Gly Pro Pro
                995                 1000                1005
        Gly Pro Pro Gly Pro Pro
            1010

<210> SEQ ID NO 49
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 18, 26, 29
<223> OTHER INFORMATION: hydroxyproline

<400> SEQUENCE: 49

Gly Pro Xaa Gly Pro Xaa Gly Pro Xaa Gly Pro Xaa Gly Pro Xaa Gly
  1               5                  10                  15

Pro Xaa His Arg Gly Phe Thr Gly Pro Xaa Gly Pro Xaa
                20                  25

<210> SEQ ID NO 50
<211> LENGTH: 36
<212> TYPE: PRT
<213> ORGANISM: Artificial Sequence
<220> FEATURE:
```

```
<223> OTHER INFORMATION: Synthetic
<220> FEATURE:
<221> NAME/KEY: MOD_RES
<222> LOCATION: 3, 6, 9, 12, 15, 18, 33, 36
<223> OTHER INFORMATION: hydroxyproline

<400> SEQUENCE: 50

Gly Pro Xaa Gly Pro Xaa Gly Pro Xaa Gly Pro Xaa Gly Pro Xaa Gly
 1               5                  10                  15

Pro Xaa Arg Gly Ala Gln Gly Pro Pro Gly Ala Thr Gly Phe Gly Pro
            20                  25                  30

Xaa Gly Pro Xaa
        35

<210> SEQ ID NO 51
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 18, 28, 31
<223> OTHER INFORMATION: hydroxyproline

<400> SEQUENCE: 51

Gly Pro Xaa Gly Pro Xaa Gly Pro Xaa Gly Pro Xaa Gly Pro Xaa Gly
 1               5                  10                  15

Pro Xaa Ala Gly Gln Arg Gly Ile Val Gly Pro Xaa Gly Pro Xaa
            20                  25                  30

<210> SEQ ID NO 52
<211> LENGTH: 43
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 18, 24 40, 43
<223> OTHER INFORMATION: hydroxyproline

<400> SEQUENCE: 52

Gly Pro Xaa Gly Pro Xaa Gly Pro Xaa Gly Pro Xaa Gly Pro Xaa Gly
 1               5                  10                  15

Pro Xaa Gly Pro Arg Gly Leu Xaa Gly Glu Arg Gly Arg Thr Gly Pro
            20                  25                  30

Ala Gly Ala Ala Gly Gly Pro Xaa Gly Pro Xaa
        35                  40

<210> SEQ ID NO 53
<211> LENGTH: 37
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 18, 21, 27, 34, 37
<223> OTHER INFORMATION: hydroxyproline

<400> SEQUENCE: 53

Gly Pro Xaa Gly Pro Xaa Gly Pro Xaa Gly Pro Xaa Gly Pro Xaa Gly
 1               5                  10                  15

Pro Xaa Gly Asn Xaa Gly Thr Asp Gly Ile Xaa Gly Ala Lys Gly Gly
            20                  25                  30
```

Pro Xaa Gly Pro Xaa
        35

<210> SEQ ID NO 54
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 18, 32, 35
<223> OTHER INFORMATION: hydroxyproline

<400> SEQUENCE: 54

Gly Pro Xaa Gly Pro Xaa Gly Pro Xaa Gly Pro Xaa Gly Pro Xaa Gly
 1               5                  10                  15

Pro Xaa Ala Arg Gly Pro Glu Gly Ala Gln Gly Pro Arg Gly Pro Xaa
            20                  25                  30

Gly Pro Xaa
        35

<210> SEQ ID NO 55
<211> LENGTH: 38
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 18, 32, 35, 38
<223> OTHER INFORMATION: hydroxyproline

<400> SEQUENCE: 55

Gly Pro Xaa Gly Pro Xaa Gly Pro Xaa Gly Pro Xaa Gly Pro Xaa Gly
 1               5                  10                  15

Pro Xaa Asp Ala Gly Pro Gln Gly Lys Val Gly Pro Ser Gly Ala Xaa
            20                  25                  30

Gly Pro Xaa Gly Pro Xaa
        35

<210> SEQ ID NO 56
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 18, 27, 33, 36
<223> OTHER INFORMATION: hydroxyproline
<220> FEATURE:
<221> NAME/KEY: MOD_RES
<222> LOCATION: 21, 26
<223> OTHER INFORMATION: ornithine modifications of arginine

<400> SEQUENCE: 56

Gly Pro Xaa Gly Pro Xaa Gly Pro Xaa Gly Pro Xaa Gly Pro Xaa Gly
 1               5                  10                  15

Pro Xaa Gly Ala Xaa Gly Leu Thr Gly Xaa Xaa Gly Asp Ala Gly Pro
            20                  25                  30

Xaa Gly Pro Xaa
        35

<210> SEQ ID NO 57

```
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 2
<223> OTHER INFORMATION: hydroxyproline

<400> SEQUENCE: 57

Glu Xaa Gly Ile Ala Gly Phe Lys Gly Glu Gln Gly Pro Lys Gly Glu
 1               5                  10                  15

Thr Gly

<210> SEQ ID NO 58
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 4, 7, 10, 13, 16, 19
<223> OTHER INFORMATION: hydroxyproline

<400> SEQUENCE: 58

Gly Gly Pro Xaa Gly Pro Xaa Gly Pro Xaa Gly Pro Xaa Gly Pro Xaa
 1               5                  10                  15

Gly Glu Xaa Gly Ile Ala Gly Phe Lys Gly Glu Gln Gly Pro Lys Gly
                20                  25                  30

Glu Thr Gly
         35

<210> SEQ ID NO 59
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 2, 5, 8, 11, 14, 17
<223> OTHER INFORMATION: hydroxyproline

<400> SEQUENCE: 59

Pro Xaa Gly Pro Xaa Gly Pro Xaa Gly Pro Xaa Gly Pro Xaa Gly Glu
 1               5                  10                  15

Xaa Gly Ile Ala Gly Phe Lys Gly Glu Gln Gly Pro Lys Gly Glu Thr
                20                  25                  30

Gly

<210> SEQ ID NO 60
<211> LENGTH: 15
<212> TYPE: PRT
<213> ORGANISM: Homo sapiens

<400> SEQUENCE: 60

Gly Glu Pro Gly Ile Ala Gly Phe Lys Gly Glu Gln Gly Pro Lys
 1               5                  10                  15

<210> SEQ ID NO 61
<211> LENGTH: 36
<212> TYPE: PRT
<213> ORGANISM: Artificial Sequence
<220> FEATURE:
```

-continued

```
<223> OTHER INFORMATION: Synthetic
<220> FEATURE:
<221> NAME/KEY: MOD_RES
<222> LOCATION: 3, 6, 9, 12, 15, 18, 27, 33, 36
<223> OTHER INFORMATION: hydroxyproline

<400> SEQUENCE: 61

Gly Pro Xaa Gly Pro Xaa Gly Pro Xaa Gly Pro Xaa Gly Pro Xaa Gly
1               5                   10                  15

Pro Xaa Gly Ala Arg Gly Leu Thr Gly Arg Xaa Gly Asp Ala Gly Pro
            20                  25                  30

Xaa Gly Pro Xaa
        35

<210> SEQ ID NO 62
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 18, 33, 37, 40
<223> OTHER INFORMATION: hydroxyproline

<400> SEQUENCE: 62

Gly Pro Xaa Gly Pro Xaa Gly Pro Xaa Gly Pro Xaa Gly Pro Xaa Gly
1               5                   10                  15

Pro Xaa Gly Ile Ala Gly Phe Lys Gly Glu Gln Gly Pro Lys Gly Glu
            20                  25                  30

Xaa Gly Gly Pro Xaa Gly Pro Xaa
        35                  40

<210> SEQ ID NO 63
<211> LENGTH: 48
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 18, 33, 42, 45, 48
<223> OTHER INFORMATION: hydroxyproline

<400> SEQUENCE: 63

Gly Pro Xaa Gly Pro Xaa Gly Pro Xaa Gly Pro Xaa Gly Pro Xaa Gly
1               5                   10                  15

Pro Xaa Gly Ile Ala Gly Phe Lys Gly Glu Gln Gly Pro Lys Gly Glu
            20                  25                  30

Xaa Gly Ala Arg Gly Leu Thr Gly Arg Xaa Gly Pro Xaa Gly Pro Xaa
        35                  40                  45

<210> SEQ ID NO 64
<211> LENGTH: 38
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 18, 20, 35, 38
<223> OTHER INFORMATION: hydroxyproline

<400> SEQUENCE: 64

Gly Pro Xaa Gly Pro Xaa Gly Pro Xaa Gly Pro Xaa Gly Pro Xaa Gly
1               5                   10                  15
```

```
Pro Xaa Met Xaa Gly Glu Arg Gly Ala Ala Gly Ile Ala Gly Pro Lys
        20                  25                  30

Gly Pro Xaa Gly Pro Xaa
            35

<210> SEQ ID NO 65
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 18, 27, 33, 36
<223> OTHER INFORMATION: hydroxyproline
<220> FEATURE:
<221> NAME/KEY: MOD_RES
<222> LOCATION: 21, 26
<223> OTHER INFORMATION: citrulline modifications of arginine

<400> SEQUENCE: 65

Gly Pro Xaa Gly Pro Xaa Gly Pro Xaa Gly Pro Xaa Gly Pro Xaa Gly
 1               5                  10                  15

Pro Xaa Gly Ala Xaa Gly Leu Thr Gly Xaa Xaa Gly Asp Ala Gly Pro
        20                  25                  30

Xaa Gly Pro Xaa
        35

<210> SEQ ID NO 66
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 18, 29, 32, 35
<223> OTHER INFORMATION: hydroxyproline

<400> SEQUENCE: 66

Gly Pro Xaa Gly Pro Xaa Gly Pro Xaa Gly Pro Xaa Gly Pro Xaa Gly
 1               5                  10                  15

Pro Xaa Leu Val Gly Pro Arg Gly Glu Arg Gly Phe Xaa Gly Pro Xaa
        20                  25                  30

Gly Pro Xaa
        35

<210> SEQ ID NO 67
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 18, 27, 30, 33
<223> OTHER INFORMATION: hydroxyproline

<400> SEQUENCE: 67

Gly Pro Xaa Gly Pro Xaa Gly Pro Xaa Gly Pro Xaa Gly Pro Xaa Gly
 1               5                  10                  15

Pro Xaa Gly Ala Arg Gly Leu Thr Gly Arg Xaa Gly Pro Xaa Gly Pro
        20                  25                  30

Xaa
```

```
<210> SEQ ID NO 68
<211> LENGTH: 26
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 23, 26
<223> OTHER INFORMATION: hydroxyproline

<400> SEQUENCE: 68
```

Gly Pro Xaa Gly Pro Xaa Gly Pro Xaa Gly Pro Xaa Gly Pro Xaa His
1               5                   10                  15

Arg Gly Phe Thr Gly Pro Xaa Gly Pro Xaa
            20                  25

```
<210> SEQ ID NO 69
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 30, 33
<223> OTHER INFORMATION: hydroxyproline

<400> SEQUENCE: 69
```

Gly Pro Xaa Gly Pro Xaa Gly Pro Xaa Gly Pro Xaa Gly Pro Xaa Arg
1               5                   10                  15

Gly Ala Gln Gly Pro Pro Gly Ala Thr Gly Phe Gly Pro Xaa Gly Pro
            20                  25                  30

Xaa

```
<210> SEQ ID NO 70
<211> LENGTH: 28
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 25, 28
<223> OTHER INFORMATION: hydroxyproline

<400> SEQUENCE: 70
```

Gly Pro Xaa Gly Pro Xaa Gly Pro Xaa Gly Pro Xaa Gly Pro Xaa Ala
1               5                   10                  15

Gly Gln Arg Gly Ile Val Gly Pro Xaa Gly Pro Xaa
            20                  25

```
<210> SEQ ID NO 71
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 21, 37, 40
<223> OTHER INFORMATION: hydroxyproline

<400> SEQUENCE: 71
```

Gly Pro Xaa Gly Pro Xaa Gly Pro Xaa Gly Pro Xaa Gly Pro Xaa Gly
1               5                   10                  15

```
Pro Arg Gly Leu Xaa Gly Glu Arg Gly Arg Thr Gly Pro Ala Gly Ala
            20                  25                  30

Ala Gly Gly Pro Xaa Gly Pro Xaa
        35                  40

<210> SEQ ID NO 72
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 18, 24, 31, 34
<223> OTHER INFORMATION: hydroxyproline

<400> SEQUENCE: 72

Gly Pro Xaa Gly Pro Xaa Gly Pro Xaa Gly Pro Xaa Gly Pro Xaa Gly
1               5                   10                  15

Asn Xaa Gly Thr Asp Gly Ile Xaa Gly Ala Lys Gly Pro Xaa Gly
            20                  25                  30

Pro Xaa

<210> SEQ ID NO 73
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 29, 32
<223> OTHER INFORMATION: hydroxyproline

<400> SEQUENCE: 73

Gly Pro Xaa Gly Pro Xaa Gly Pro Xaa Gly Pro Xaa Gly Pro Xaa Ala
1               5                   10                  15

Arg Gly Pro Glu Gly Ala Gln Gly Pro Arg Gly Pro Xaa Gly Pro Xaa
            20                  25                  30

<210> SEQ ID NO 74
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 29, 32, 35
<223> OTHER INFORMATION: hydroxyproline

<400> SEQUENCE: 74

Gly Pro Xaa Gly Pro Xaa Gly Pro Xaa Gly Pro Xaa Gly Pro Xaa Asp
1               5                   10                  15

Ala Gly Pro Gln Gly Lys Val Gly Pro Ser Gly Ala Xaa Gly Pro Xaa
            20                  25                  30

Gly Pro Xaa
        35

<210> SEQ ID NO 75
<211> LENGTH: 33
<212> TYPE: PRT
<213> ORGANISM: Artificial Sequence
<220> FEATURE:
<223> OTHER INFORMATION: Synthetic
<220> FEATURE:
```

```
<221> NAME/KEY: MOD_RES
<222> LOCATION: 3, 6, 9, 12, 15, 24, 30, 33
<223> OTHER INFORMATION: hydroxyproline
<220> FEATURE:
<221> NAME/KEY: MOD_RES
<222> LOCATION: 18, 23
<223> OTHER INFORMATION: ornithine modifications of arginine

<400> SEQUENCE: 75

Gly Pro Xaa Gly Pro Xaa Gly Pro Xaa Gly Pro Xaa Gly Pro Xaa Gly
 1               5                   10                  15

Ala Xaa Gly Leu Thr Gly Xaa Xaa Gly Asp Ala Gly Pro Xaa Gly Pro
            20                  25                  30

Xaa

<210> SEQ ID NO 76
<211> LENGTH: 900
<212> TYPE: PRT
<213> ORGANISM: Artificial Sequence
<220> FEATURE:
<223> OTHER INFORMATION: Exemplary motif
<220> FEATURE:
<221> NAME/KEY: VARIANT
<222> LOCATION: (1)...(300)
<223> OTHER INFORMATION: Xaa = hydroxyproline
<220> FEATURE:
<221> NAME/KEY: VARIANT
<222> LOCATION: (301)...(600)
<223> OTHER INFORMATION: Xaa = any amino acid
<220> FEATURE:
<221> NAME/KEY: VARIANT
<222> LOCATION: (601)...(900)
<223> OTHER INFORMATION: Xaa = hydroxyproline

<400> SEQUENCE: 76

Gly Pro Xaa Gly Pro Xaa Gly Pro Xaa Gly Pro Xaa Gly Pro Xaa Gly
 1               5                   10                  15

Pro Xaa Gly Pro Xaa Gly Pro Xaa Gly Pro Xaa Gly Pro Xaa Gly Pro
            20                  25                  30

Xaa Gly Pro Xaa Gly Pro Xaa Gly Pro Xaa Gly Pro Xaa Gly Pro Xaa
            35                  40                  45

Gly Pro Xaa Gly Pro Xaa Gly Pro Xaa Gly Pro Xaa Gly Pro Xaa Gly
 50                  55                  60

Pro Xaa Gly Pro Xaa Gly Pro Xaa Gly Pro Xaa Gly Pro Xaa Gly Pro
 65                  70                  75                  80

Xaa Gly Pro Xaa Gly Pro Xaa Gly Pro Xaa Gly Pro Xaa Gly Pro Xaa
            85                  90                  95

Gly Pro Xaa Gly Pro Xaa Gly Pro Xaa Gly Pro Xaa Gly Pro Xaa Gly
            100                 105                 110

Pro Xaa Gly Pro Xaa Gly Pro Xaa Gly Pro Xaa Gly Pro Xaa Gly Pro
            115                 120                 125

Xaa Gly Pro Xaa Gly Pro Xaa Gly Pro Xaa Gly Pro Xaa Gly Pro Xaa
            130                 135                 140

Gly Pro Xaa Gly Pro Xaa Gly Pro Xaa Gly Pro Xaa Gly Pro Xaa Gly
145                 150                 155                 160

Pro Xaa Gly Pro Xaa Gly Pro Xaa Gly Pro Xaa Gly Pro Xaa Gly Pro
                165                 170                 175

Xaa Gly Pro Xaa Gly Pro Xaa Gly Pro Xaa Gly Pro Xaa Gly Pro Xaa
            180                 185                 190

Gly Pro Xaa Gly Pro Xaa Gly Pro Xaa Gly Pro Xaa Gly Pro Xaa Gly
            195                 200                 205
```

Pro Xaa Gly Pro Xaa Gly Pro Xaa Gly Pro Xaa Gly Pro
    210                 215                 220

Xaa Gly Pro Xaa Gly Pro Xaa Gly Pro Xaa Gly Pro Xaa
225                 230                 235                 240

Gly Pro Xaa Gly Pro Xaa Gly Pro Xaa Gly Pro Xaa Gly
            245                 250                 255

Pro Xaa Gly Pro Xaa Gly Pro Xaa Gly Pro Xaa Gly Pro
        260                 265                 270

Xaa Gly Pro Xaa Gly Pro Xaa Gly Pro Xaa Gly Pro Xaa
            275                 280                 285

Gly Pro Xaa Gly Pro Xaa Gly Pro Xaa Gly Xaa Xaa Gly
    290                 295                 300

Xaa Xaa Gly Xaa Xaa Gly Xaa Xaa Gly Xaa Xaa Gly Xaa
305                 310                 315                 320

Xaa Gly Xaa Xaa Gly Xaa Xaa Gly Xaa Xaa Gly Xaa Xaa
            325                 330                 335

Gly Xaa Xaa Gly Xaa Xaa Gly Xaa Xaa Gly Xaa Xaa Gly
    340                 345                 350

Xaa Xaa Gly Xaa Xaa Gly Xaa Xaa Gly Xaa Xaa Gly Xaa
            355                 360                 365

Xaa Gly Xaa Xaa Gly Xaa Xaa Gly Xaa Xaa Gly Xaa Xaa
    370                 375                 380

Gly Xaa Xaa Gly Xaa Xaa Gly Xaa Xaa Gly Xaa Xaa Gly
385                 390                 395                 400

Xaa Xaa Gly Xaa Xaa Gly Xaa Xaa Gly Xaa Xaa Gly Xaa
            405                 410                 415

Xaa Gly Xaa Xaa Gly Xaa Xaa Gly Xaa Xaa Gly Xaa Xaa
    420                 425                 430

Gly Xaa Xaa Gly Xaa Xaa Gly Xaa Xaa Gly Xaa Xaa Gly
        435                 440                 445

Xaa Xaa Gly Xaa Xaa Gly Xaa Xaa Gly Xaa Xaa Gly Xaa
450                 455                 460

Xaa Gly Xaa Xaa Gly Xaa Xaa Gly Xaa Xaa Gly Xaa Xaa
465                 470                 475                 480

Gly Xaa Xaa Gly Xaa Xaa Gly Xaa Xaa Gly Xaa Xaa Gly
            485                 490                 495

Xaa Xaa Gly Xaa Xaa Gly Xaa Xaa Gly Xaa Xaa Gly Xaa
        500                 505                 510

Xaa Gly Xaa Xaa Gly Xaa Xaa Gly Xaa Xaa Gly Xaa Xaa
    515                 520                 525

Gly Xaa Xaa Gly Xaa Xaa Gly Xaa Xaa Gly Xaa Xaa Gly
    530                 535                 540

Xaa Xaa Gly Xaa Xaa Gly Xaa Xaa Gly Xaa Xaa Gly Xaa
545                 550                 555                 560

Xaa Gly Xaa Xaa Gly Xaa Xaa Gly Xaa Xaa Gly Xaa Xaa
            565                 570                 575

Gly Xaa Xaa Gly Xaa Xaa Gly Xaa Xaa Gly Xaa Xaa Gly
        580                 585                 590

Xaa Xaa Gly Xaa Xaa Gly Xaa Xaa Gly Pro Gly Pro Xaa Gly Pro
        595                 600                 605

Xaa Gly Pro Xaa Gly Pro Xaa Gly Pro Xaa Gly Pro Xaa
    610                 615                 620

Gly Pro Xaa Gly Pro Xaa Gly Pro Xaa Gly Pro Xaa Gly

```
                625                 630                 635                 640

Pro Xaa Gly Pro Xaa Gly Pro Xaa Gly Pro Xaa Gly Pro Xaa Gly Pro
                645                 650                 655

Xaa Gly Pro Xaa Gly Pro Xaa Gly Pro Xaa Gly Pro Xaa Gly Pro Xaa
                660                 665                 670

Gly Pro Xaa Gly Pro Xaa Gly Pro Xaa Gly Pro Xaa Gly Pro Xaa Gly
                675                 680                 685

Pro Xaa Gly Pro Xaa Gly Pro Xaa Gly Pro Xaa Gly Pro Xaa Gly Pro
                690                 695                 700

Xaa Gly Pro Xaa Gly Pro Xaa Gly Pro Xaa Gly Pro Xaa Gly Pro Xaa
705                 710                 715                 720

Gly Pro Xaa Gly Pro Xaa Gly Pro Xaa Gly Pro Xaa Gly Pro Xaa Gly
                725                 730                 735

Pro Xaa Gly Pro Xaa Gly Pro Xaa Gly Pro Xaa Gly Pro Xaa Gly Pro
                740                 745                 750

Xaa Gly Pro Xaa Gly Pro Xaa Gly Pro Xaa Gly Pro Xaa Gly Pro Xaa
                755                 760                 765

Gly Pro Xaa Gly Pro Xaa Gly Pro Xaa Gly Pro Xaa Gly Pro Xaa Gly
770                 775                 780

Pro Xaa Gly Pro Xaa Gly Pro Xaa Gly Pro Xaa Gly Pro Xaa Gly Pro
785                 790                 795                 800

Xaa Gly Pro Xaa Gly Pro Xaa Gly Pro Xaa Gly Pro Xaa Gly Pro Xaa
                805                 810                 815

Gly Pro Xaa Gly Pro Xaa Gly Pro Xaa Gly Pro Xaa Gly Pro Xaa Gly
                820                 825                 830

Pro Xaa Gly Pro Xaa Gly Pro Xaa Gly Pro Xaa Gly Pro Xaa Gly Pro
                835                 840                 845

Xaa Gly Pro Xaa Gly Pro Xaa Gly Pro Xaa Gly Pro Xaa Gly Pro Xaa
                850                 855                 860

Gly Pro Xaa Gly Pro Xaa Gly Pro Xaa Gly Pro Xaa Gly Pro Xaa Gly
865                 870                 875                 880

Pro Xaa Gly Pro Xaa Gly Pro Xaa Gly Pro Xaa Gly Pro Xaa Gly Pro
                885                 890                 895

Xaa Gly Pro Xaa
            900

<210> SEQ ID NO 77
<211> LENGTH: 37
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 34, 37
<223> OTHER INFORMATION: hydroxyproline

<400> SEQUENCE: 77

Gly Pro Xaa Gly Pro Xaa Gly Pro Xaa Gly Pro Xaa Gly Pro Xaa Gly
 1               5                  10                  15

Ile Ala Gly Phe Lys Gly Glu Gln Gly Pro Lys Gly Glu Pro Gly Gly
                20                  25                  30

Pro Xaa Gly Pro Xaa
            35

<210> SEQ ID NO 78
<211> LENGTH: 36
```

```
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 33, 36
<223> OTHER INFORMATION: hydroxyproline

<400> SEQUENCE: 78

Gly Pro Xaa Gly Pro Xaa Gly Pro Xaa Gly Pro Xaa Gly Pro Xaa Gly
 1               5                  10                  15

Ile Ala Gly Phe Lys Gly Glu Gln Gly Pro Lys Gly Glu Thr Gly Pro
            20                  25                  30

Xaa Gly Pro Xaa
        35

<210> SEQ ID NO 79
<211> LENGTH: 48
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 33, 42, 45, 48
<223> OTHER INFORMATION: hydroxyproline

<400> SEQUENCE: 79

Gly Pro Xaa Gly Pro Xaa Gly Pro Xaa Gly Pro Xaa Gly Pro Xaa Gly
 1               5                  10                  15

Ile Ala Gly Phe Lys Gly Glu Gln Gly Pro Lys Gly Glu Thr Gly Pro
            20                  25                  30

Xaa Gly Ala Arg Gly Leu Thr Gly Arg Xaa Gly Pro Xaa Gly Pro Xaa
        35                  40                  45

<210> SEQ ID NO 80
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 2, 5, 8, 11, 14, 17
<223> OTHER INFORMATION: hydroxyproline

<400> SEQUENCE: 80

Pro Xaa Gly Pro Xaa Gly Pro Xaa Gly Pro Xaa Gly Pro Xaa Gly Glu
 1               5                  10                  15

Xaa Gly Ile Ala Gly Phe Lys Gly Glu Gln Gly Pro Lys Gly Glu Thr
            20                  25                  30

Gly

<210> SEQ ID NO 81
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 4, 7, 10, 13, 16, 19
<223> OTHER INFORMATION: hydroxyproline

<400> SEQUENCE: 81
```

```
Gly Gly Pro Xaa Gly Pro Xaa Gly Pro Xaa Gly Pro Xaa Gly Pro Xaa
1               5                   10                  15

Gly Glu Xaa Gly Ile Ala Gly Phe Lys Gly Glu Gln Gly Pro Lys Gly
            20                  25                  30

Glu Thr Gly
        35
```

<210> SEQ ID NO 82
<211> LENGTH: 4
<212> TYPE: PRT
<213> ORGANISM: Artificial Sequence
<220> FEATURE:
<223> OTHER INFORMATION: Linker

<400> SEQUENCE: 82

```
Lys Lys Tyr Gly
1
```

<210> SEQ ID NO 83
<211> LENGTH: 24
<212> TYPE: PRT
<213> ORGANISM: Artificial Sequence
<220> FEATURE:
<223> OTHER INFORMATION: Exemplary motif

<400> SEQUENCE: 83

```
Gly Pro Arg Gly Pro Arg Gly Pro Arg Gly Pro Arg Gly Pro Arg Gly
1               5                   10                  15

Pro Arg Gly Pro Arg Gly Pro Arg
            20
```

<210> SEQ ID NO 84
<211> LENGTH: 40
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 3, 6, 9, 12, 15, 18, 37, 40
<223> OTHER INFORMATION: hydroxyproline

<400> SEQUENCE: 84

```
Gly Pro Xaa Gly Pro Xaa Gly Pro Xaa Gly Pro Xaa Gly Pro Xaa Gly
1               5                   10                  15

Pro Xaa Gly Ile Ala Gly Phe Lys Gly Glu Gln Gly Pro Lys Gly Glu
            20                  25                  30

Pro Gly Gly Pro Xaa Gly Pro Xaa
        35                  40
```

<210> SEQ ID NO 85
<211> LENGTH: 5
<212> TYPE: PRT
<213> ORGANISM: Artificial Sequence
<220> FEATURE:
<223> OTHER INFORMATION: Synthetic

<400> SEQUENCE: 85

```
Lys Lys Phe Tyr Gly
1               5
```

<210> SEQ ID NO 86
<211> LENGTH: 41
<212> TYPE: PRT
<213> ORGANISM: Artificial Sequence

```
<220> FEATURE:
<223> OTHER INFORMATION: Synthetic
<220> FEATURE:
<221> NAME/KEY: MOD_RES
<222> LOCATION: 4, 7, 10, 13, 16, 19, 38, 41
<223> OTHER INFORMATION: hydroxyproline

<400> SEQUENCE: 86

Gly Gly Pro Xaa Gly Pro Xaa Gly Pro Xaa Gly Pro Xaa Gly Pro Xaa
 1               5                  10                  15

Gly Pro Xaa Gly Ile Ala Gly Phe Lys Gly Glu Gln Gly Pro Lys Gly
            20                  25                  30

Glu Pro Gly Gly Pro Xaa Gly Pro Xaa
        35                  40

<210> SEQ ID NO 87
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: 2, 5, 8, 11, 14, 17
<223> OTHER INFORMATION: hydroxyproline

<400> SEQUENCE: 87

Pro Xaa Gly Pro Xaa Gly Pro Xaa Gly Pro Xaa Gly Pro Xaa Gly Glu
 1               5                  10                  15

Xaa Gly Ile Ala Gly Phe Lys Gly Glu Gln Gly Pro Lys Gly Glu Thr
            20                  25                  30

Gly
```